(12) United States Patent
Geneste et al.

(10) Patent No.: US 7,279,468 B2
(45) Date of Patent: Oct. 9, 2007

(54) INTEGRIN LIGANDS

(75) Inventors: Herve Geneste, Neuhofen (DE);
Andreas Kling, Mannheim (DE); Udo Lange, Mannheim (DE); Werner Seitz, Plankstadt (DE); Claudia Isabella Graef, Mannheim (DE); Thomas Subkoski, Ladenburg (DE); Wilfried Hornberger, Neustadt (DE); Arnulf Lauterbach, Ludwigshafen (DE)

(73) Assignee: Abbott GmbH & Co. KG, Wiesbadem (DE)

( * ) Notice: Subject to any disclaimer, the term of this patent is extended or adjusted under 35 U.S.C. 154(b) by 301 days.

(21) Appl. No.: 10/311,369

(22) PCT Filed: Jun. 15, 2001

(86) PCT No.: PCT/EP01/06779

§ 371 (c)(1),
(2), (4) Date: Sep. 8, 2003

(87) PCT Pub. No.: WO01/96312

PCT Pub. Date: Dec. 20, 2001

(65) Prior Publication Data

US 2004/0063934 A1 Apr. 1, 2004

(30) Foreign Application Priority Data

Jun. 14, 2000 (DE) .............................. 100 28 575

(51) Int. Cl.
*A01N 43/00* (2006.01)
*A61K 31/55* (2006.01)
*C07D 513/00* (2006.01)
*C07D 487/00* (2006.01)

(52) U.S. Cl. ........................ 514/212.07; 514/217.03; 514/217.02; 540/523; 540/524; 540/531

(58) Field of Classification Search ........... 514/212.06, 514/212.07, 231.01; 540/521, 522, 523, 540/593
See application file for complete search history.

(56) References Cited

U.S. PATENT DOCUMENTS 5,565,449 A 10/1996 Blackburn et al.
6,514,964 B1 * 2/2003 Chen et al. ............. 514/212.06

FOREIGN PATENT DOCUMENTS

| DE | 19653645 | 6/1998 |
|---|---|---|
| EP | 540334 | 5/1993 |
| EP | 908764 | 4/1999 |
| WO | WO93.08174 | 4/1993 |
| WO | WO96/06087 | 2/1996 |
| WO | WO96/26190 | 8/1996 |
| WO | WO97/24122 | 7/1997 |
| WO | WO97/24124 | 7/1997 |
| WO | WO98/02432 | 1/1998 |
| WO | WO98/14192 | 4/1998 |
| WO | WO99/05107 | 2/1999 |
| WO | WO99/06049 | 2/1999 |
| WO | WO99/11626 | 3/1999 |
| WO | WO 01/10847 | 2/2001 |
| WO | WO 01/23357 | 4/2001 |

OTHER PUBLICATIONS

Basic and Clinical Pharmacology, 7th Edition, 1998, Bertram G. Katzung, pp. 881-884.*
Miller et al, "Discovery of Orally Active Nonpeptide Vitronectin Receptor Antagonists Based on a 2-Benzazepine Gly-Asp Mimetic" Journal of Medicinal Chemstry, vol. 43, pp. 22-26 (2000).*
Badger et al, "Disease-Modifying Activity of SB 273005, an Orally Active Nonpeptide αvβ3 (Vltronectin Receptor) Antagonist, in Rat Adjuvant-Induced Arthritis" Arthritis & Rheumatism, vol. 44(1), pp. 128-137 (2001).*
Lark et al, "Antagonism of the Osteoclast Vitronectin Receptor with an Orally Active Nonpeptide Inhibitor Prevents Cancellous Bone Loss in the Ovarectomized Rat" Journal of Bone and Mineral Research, vol. 16(2), pp. 319-327 (2001).*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
E. Ruoslahi et al. Cell 1986, 44, 517-518.
E. Ruoslathi et al., Science 1987, 238, 491-497.
L. Piali, J. Cell Biol. 1995, 130, 451-460.
C.D. Buckley et al., J. Cell Science 1996, 109, 437-445.
M.L. Kireeva et al., J. Biol. Chem. 1998, 273, 3090-3096.
M. Aumailley et al., FEBS Letts. 1991, 291, 50-54.
J.W. Smith et al., J. Biol. Chem. 1990, 265, 12267-12271.
M. Pfaff et al., J. Biol. Chem. 1994, 269, 20233-20238.
D.A. Cheresh et al., J. Biol. Chem. 1987, 262, 17703-17711.
K.C. Nicolaou et al., Bioorg. Med. Chem. 1998, 6, 1185-1208.

* cited by examiner

*Primary Examiner*—Zachary C Tucker
(74) *Attorney, Agent, or Firm*—Wood, Phillips, Katz, Clark & Mortimer

(57) ABSTRACT

The invention relates to novel compounds which bind to integrin receptors, their use as ligands of integrin receptors, in particular as ligands of the $\alpha_v\beta_3$ integrin receptor, their use, and pharmaceutical preparations comprising these compounds.

16 Claims, No Drawings

INTEGRIN LIGANDS

The present invention relates to novel compounds which bind to integrin receptors, their use as ligands of integrin receptors, in particular as ligands of the $\alpha_v\beta_3$ integrin receptor, their use, and pharmaceutical preparations comprising these compounds.

Integrins are cell surface glycoprotein receptors which mediate interactions between identical and different cells as well as between cells and extracellular matrix proteins. They are involved in physiological processes, such as embryogenesis, hemostasis, wound healing, immune response and formation/maintenance of the tissue architecture.

Disturbances in the gene expression of cell adhesion molecules and functional disorders of the receptors can contribute to the pathogenesis of many disorders, such as tumors, thromboembolic events, cardiovascular disorders, lung diseases, disorders of the CNS, the kidney, the gastrointestinal tract or inflammations.

Integrins are heterodimers of an $\alpha$- and a $\beta$-transmembrane subunit in each case, which are noncovalently bonded. Up to now, 16 different $\alpha$- and 8 different $\beta$-subunits and 22 different combinations have been identified.

Integrin $\alpha_v\beta_3$, also called the vitronectin receptor, mediates adhesion to a multiplicity of ligands-plasma proteins, extracellular matrix proteins, cell surface proteins, of which the majority contain the amino acid sequence RGD (Cell, 1986, 44, 517-518; Science 1987, 238, 491-497), such as vitronectin, fibrinogen, fibronectin, von Willebrand factor, thrombospondin, osteopontin, laminin, collagen, thrombin, tenascin, MMP-2, bone sialoprotein II, various viral, fungal, parasitic and bacterial proteins, natural integrin antagonists such as disintegrins, neurotoxins—mambin—and blood fluke proteins—decorsin, ornatin—and also some non-RGD ligands, such as Cyr-61 and PECAM-1 (L. Piali, J. Cell Biol. 1995, 130, 451-460; Buckley, J. Cell Science 1996, 109, 437-445, J. Biol. Chem. 1998, 273, 3090-3096).

A number of integrin receptors show cross-reactivity with ligands' which contain the RGD motif. Thus integrin $\alpha_{IIb}\beta_3$, also called the platelet fibrinogen receptor, recognizes fibronectin, vitronectin, thrombospondin, von Willebrand factor and fibrinogen.

Integrin $\alpha_v\beta_3$ is expressed, inter alia, from endothelial cells, blood platelets, monocytes/macrophages, smooth muscle cells, some B cells, fibroblasts, osteoclasts and various tumor cells, such as melanoma, glioblastoma, lung, breast, prostate and bladder carcinomas, osteosarcomas or neuroblastomas.

Increased expression is observed under various pathological conditions, such as in the prothrombotic state, in vascular injury, tumor growth or metastasis or reperfusion and on activated cells, in particular on endothelial cells, smooth muscle cells or macrophages.

An involvement of integrin $\alpha_v\beta_3$ has been demonstrated, inter alia, in the following syndromes:

cardiovascular disorders such as atherosclerosis, restenosis after vascular injury, and angioplasty (neointima formation, smooth muscle cell migration and proliferation) (J. Vasc. Surg. 1994, 19, 125-134; Circulation 1994, 90, 2203-2206), acute kidney failure (Kidney Int. 1994, 46, 1050-1058; Proc. Natl. Acad. Sci. 1993, 90, 5700-5704; Kidney Int. 1995, 48, 1375-1385), angiogenesis-associated microangiopathies such as diabetic retinopathy or rheumatoid arthritis (Ann. Rev. Physiol 1987, 49, 453-464; Int. Ophthalmol. 1987, 11, 41-50; Cell 1994, 79, 1157-1164; J. Biol. Chem. 1992, 267, 10931-10934), arterial thrombosis, stroke (phase II studies with ReoPro, Centocor Inc., 8th annual European Stroke Meeting), carcinomatous disorders, such as in tumor metastasis or in tumor growth (tumor-induced angiogenesis) (Cell 1991, 64, 327-336; Nature 1989, 339, 58-61; Science 1995, 270, 1500-1502), osteoporosis (bone resorption after proliferation, chemotaxis and adhesion of osteoclasts to bone matrix) (FASEB J. 1993, 7, 1475-1482; Exp. Cell Res. 1991, 195, 368-375, Cell 1991, 64, 327-336), high blood pressure (Am. J. Physiol. 1998, 275, H1449-H1454), psoriasis (Am. J. Pathol. 1995, 147, 1661-1667), hyperparathyroidism, Paget's disease (J. Clin. Endocrinol. Metab. 1996, 81, 1810-1820), malignant hypercalcemia (Cancer Res. 1998, 58, 1930-1935), metastatic osteolytic lesions (Am. J. Pathol. 1997, 150, 1383-1393), pathogen protein (e.g. HIV-1 tat)-induced processes (e.g. angiogenesis, Kaposi's sarcoma) (Blood 1999, 94, 663-672)

inflammation (J. Allergy Clin. Immunol. 1998, 102, 376-381), cardiac insufficiency, CHF, and also in antiviral, antiparasitic, antifungal or antibacterial therapy and prophylaxis (adhesion and internalization) (J. Infect. Dis. 1999, 180, 156-166; J. Virology 1995, 69, 2664-2666; Cell 1993, 73, 309-319).

On account of its key role, pharmaceutical preparations which contain low-molecular weight integrin $\alpha_v\beta_3$ ligands are of high therapeutic or diagnostic benefit, inter alia, in the indications mentioned.

Advantageous $\alpha_v\beta_3$ integrin receptor ligands bind to the integrin $\alpha_v\beta_3$ receptor with an increased affinity.

In contrast to integrin $\alpha_v\beta_3$, particularly advantageous $\alpha_v\beta_3$ integrin receptor ligands additionally have an increased selectivity and are less active with respect to the integrin $\alpha_{IIb}\beta_3$ by at least a factor of 10, preferably at least a factor of 100.

For a multiplicity of compounds, such as anti-$\alpha_v\beta_3$ monoclonal antibodies, peptides which contain the RGD binding sequence, natural, RGD-containing proteins (e.g. disintegrins) and low-molecular weight compounds, an integrin $\alpha_v\beta_3$ antagonistic action has been shown and a positive in vivo effect demonstrated (FEBS Letts 1991, 291, 50-54; J. Biol. Chem. 1990, 265, 12267-12271; J. Biol. Chem. 1994, 269, 20233-20238; J. Cell Biol 1993, 51, 206-218; J. Biol. Chem. 1987, 262, 17703-17711; Bioorg. Med. Chem. 1998, 6, 1185-1208).

Antagonists of the $\alpha_v\beta_3$ integrin receptor bas d on a bicyclic structural element are described in DE 19653645, WO 9906049, WO 9905107, WO 9814192, WO 9724124, WO 9724122 and WO 9626190.

EP 540 334 describes bicyclic antagonists of the $\alpha_{IIb}\beta_3$ integrin receptor.

U.S. Pat. No. 5,565,449 describes bicyclic gp$_{IIb}\beta_3$ receptor antagonists.

WO 9802432 A1 describes compounds having a bicyclic molecular structure which can be used as active compounds against incontinence; WO 9606087 discloses bicyclic platelet and bone resorption inhibitors.

Further, photographic processing aids having a cyclic molecular structure are described in EP 908764.

It is an object of the present invention to make available novel integrin receptor ligands having advantageous properties.

Accordingly, we have found that this object is achieved by compounds of the formula I $$B\text{-}G\text{-}L \qquad \qquad I$$

where B, G and L have the following meanings:
L is a structural element of the formula $I_L$ $$-\text{U-T} \qquad \qquad I_L$$

where
T is a group COOH, a radical hydrolyzable to COOH or a radical bioisosteric to COOH and
—U— is $-(X_L)_a-(CR_L^1R_L^2)_b-$, $-CR_L^1=CR_L^2-$, ethynylene or $=CR_L^1-$, where
a is 0 or 1,
b is 0, 1 or 2,
$X_L$ is $CR_L^3R_L^4$, $NR_L^5$, oxygen or sulfur,
$R_L^1$, $R_L^2$, $R_L^3$, $R_L^4$
independently of one another are hydrogen, -T, —OH, —$NR_L^6R_L^7$, —CO—$NH_2$, a halogen radical, a branched or unbranched, optionally substituted $C_1$-$C_6$-alkyl, $C_2$-$C_6$-alkenyl, $C_2$-$C_6$-alkynyl, $C_3$-$C_7$-cycloalkyl, —CO—NH($C_1$-$C_6$-alkyl), —CO—N($C_1$-$C_6$-alkyl)$_2$ or $C_1$-$C_4$-alkoxy radical, an optionally substituted radical $C_1$-$C_2$-alkylene-T, $C_2$-alkenylene-T or $C_2$-alkynylene-T, an optionally substituted aryl or arylalkyl radical or in each case independently of one another are two radicals $R_L^1$ and $R_L^2$ or $R_L^3$ and $R_L^4$ or optionally $R_L^1$ and $R_L^3$ together are an optionally substituted 3- to 7-membered saturated or unsaturated carbocycle or heterocycle, which can contain up to three identical or different heteroatoms O, N, S, $R_L^5$, $R_L^6$, $R_L^7$
independently of one another are hydrogen, a branched or unbranched, optionally substituted $C_1$-$C_6$-alkyl, $C_3$-$C_7$-cycloalkyl, CO—O—$C_1$-$C_6$-alkyl, $SO_2$—$C_1$-$C_6$-alkyl or CO—$C_1$-$C_6$-alkyl radical or an optionally substituted CO—O-alkylenearyl, $SO_2$-aryl, CO-aryl, $SO_2$-alkylenearyl or CO-alkylenearyl radical, G is a structural element of the formula $I_G$

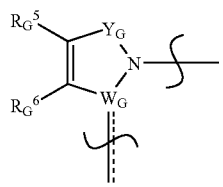

$I_G$ where
the structural element B is bonded via the ring nitrogen and the structural element L is bonded to the structural element G via $W_G$,
$Y_G$ is CO, CS, C=$NR_G^2$ or $CR_G^3R_G^4$,
$R_G^2$ is hydrogen, a hydroxyl group, a branched or unbranched, optionally substituted $C_1$-$C_6$-alkyl, $C_1$-$C_4$-alkoxy, $C_3$-$C_7$-cycloalkyl or —O—$C_3$-$C_7$-cycloalkyl radical or an optionally substituted aryl, —O-aryl, arylalkyl or —O-alkylenearyl radical, $R_G^3$, $R_G^4$
independently of one another are hydrogen or a branched or unbranched, optionally substituted $C_1$-$C_6$-alkyl, $C_2$-$C_6$-alkenyl, $C_2$-$C_6$-alkynyl or $C_1$-$C_4$-alkoxy radical or both radicals $R_G^3$ and $R_G^4$ together are a cyclic acetal —O—$CH_2$—$CH_2$—O— or —O—$CH_2$—O— or both radicals $R_G^3$ and $R_G^4$ together are an optionally substituted $C_3$-$C_7$-cycloalkyl radical, $R_G^5$ and $R_G^6$
independently of one another are hydrogen, a branched or unbranched, optionally substituted $C_1$-$C_6$-alkyl or $C_1$-$C_4$-alkoxy radical, an optionally substituted aryl or arylalkyl radical or both radicals $R_G^5$ and $R_G^6$ together are an optionally substituted, fused, unsaturated or aromatic 3- to 10-membered carbocycle or heterocycle, which can contain up to three different or identical heteroatoms O, N, S, where in this fused, unsaturated or aromatic 3- to 10-membered carbocycle or heterocycle, as substituents, independently of one another up to four substituents from the group consisting of hydroxyl, halogen or a branched or unbranched, optionally halogen-substituted $C_1$-$C_4$-alkoxy, $C_1$-$C_4$-thioalkyl or $C_1$-$C_4$-alkyl radical or an optionally halogen-substituted aryl, hetaryl or $C_3$-$C_7$-cycloalkyl radical or an optionally halogen-substituted radical —$SO_2$—$C_1$-$C_4$-alkyl, —SO—$C_1$-$C_4$-alkyl, —$SO_2$—$C_1$-$C_4$-alkylenearyl, —SO—$C_1$-$C_4$-alkylenearyl, —$SO_2$-aryl or —SO-aryl are selected, $W_G$ is a structural element selected from the group of structural elements of the formulae $I_{WG}^1$ to $I_{WG}^4$,

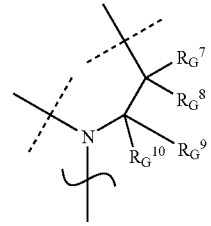

$I_{WG}^1$

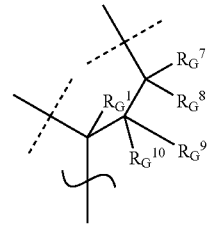

$I_{WG}^2$

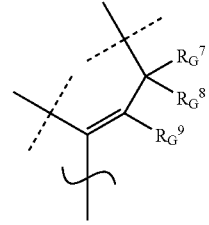

$I_{WG}^3$

-continued

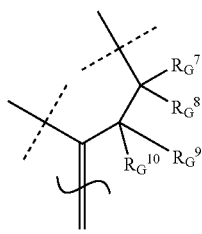

I_{WG}^4

$R_G^1$ is hydrogen, halogen, a hydroxyl group or a branched or unbranched, optionally substituted $C_1$-$C_6$-alkyl or $C_1$-$C_4$-alkoxy radical, $R_G^7$, $R_G^8$, $R_G^9$ $R_G^{10}$ independently of one another are hydrogen, a hydroxyl group, —CN, halogen, a branched or unbranched, optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-$C_3$-$C_7$-heterocycloalkyl or $C_1$-$C_4$-alkylene-$C_3$-$C_7$-heterocycloalkenyl radical, a branched or unbranched, optionally substituted radical $C_1$-$C_4$-alkylene-$OR_G^{11}$, $C_1$-$C_4$-alkylene-CO—$OR_G^{11}$, $C_1$-$C_4$-alkylene-O—CO—$R_G^{11}$, $C_1$-$C_4$-alkylene-CO-$R_G^{11}$, $C_1$-$C_4$-alkylene-$SO_2$—$NR_G^{12}R_G^{13}$, $C_1$-$C_4$-alkylene-CO—$NR_G^{12}R_G^{13}$, $C_1$-$C_4$-alkylene-O—CO—$NR_G^{12}R_G^{13}$, $C^1$-$C_4$-alkylene-$NR_G^{12}R_G^{13}$ or $C_1$-$C_4$-alkylene-$SR_G^{11}$, $C_1$-$C_4$-alkylene-SO—$R_G^{11}$, a radical —S-$R_G^{11}$, —O-$R_G^{11}$, —SO-$R_G^{11}$, —$SO_2$—$R_G^{11}$, —CO—$OR_G^{11}$, —O—CO-$R_G^{11}$, —O—CO—$NR_G^{12}R_G^{13}$, —$SO_2$—$NR_G^{12}G^{13}$, —CO—$NR_G^{12}R_G^{13}$, —$NR_G^{12}R_G^{13}$ or CO-$R_G^{11}$, an optionally substituted $C_3$-$C_7$-cycloalkyl, aryl, hetaryl, arylalkyl or hetarylalkyl radical or in each case independently of one another two radicals $R_G^7$ and $R_G^9$ or $R_G^9$ and $R_G^{10}$ or $R_G^7$ and $R^{G8}$ or $R_G^9$ and $R_G^{10}$ together are an optionally substituted, saturated or unsaturated, nonaromatic, 3- to 7-membered carbocycle or heterocycle which can contain up to 3 heteroatoms selected from the group O, N, S and up to two double bonds, $R_G^{11}$ is hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bis-alkylaminoalkylene or acylaminoalkylen radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, $R_G^{12}$, $R_G^{13}$ independently of one another are hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bis-alkylaminoalkylene or acylaminoalkylene radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G^{11}$, —CO—$OR_G^{11}$, —CO—$NR_G^{11}R_G^{11*}$ or —CO-$R_G^{11}$ or both radicals $R_G^{12}$ and $R_G^{13}$ together form a 5-to 7-membered nitrogen-containing carbocycle and $R_G^{11}$ is a radical $R_G^{11}$ which is independent of $R_G^{11}$ B is a structural element containing at least one atom which, under physiological conditions, as a hydrogen acceptor can form hydrogen bridges, where at least one hydrogen acceptor atom has a distance of 4 to 15 atom bonds to structural element G along the shortest possible route along the structural element skeleton, and the physiologically tolerable salts, prodrugs and the enantiomerically pure or diastereomerically pure and tautomeric forms.

In the structural element L, T is understood as meaning a group COOH, a radical hydrolyzable to COOH or a radical bioisosteric to COOH.

A radical hydrolyzable to COOH is understood as meaning a radical which changes into a group COOH after hydrolysis.

A group which may be mentioned by way of example as a radical hydrolyzable to COOH is

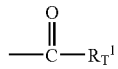

in which $R_T^1$ has the following meanings:

a) OM, where M can be a metal cation, such as an alkali metal cation, such as lithium, sodium, potassium, the equivalent of an alkaline earth metal cation, such as calcium, magnesium and barium, or an environmentally tolerable organic ammonium ion such as primary, secondary, tertiary or quaternary $C_1$-$C_4$-alkylammonium or ammonium ion, such as ONa, OK or OLi, b) a branched or unbranched, optionally halogen-substituted $C_1$-$C_8$-alkoxy radical, such as methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy, pentoxy, hexoxy, heptoxy, octoxy, difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, c) a branched or unbranched, optionally halogen-substituted $C_1$-$C_4$-alkylthio radical such as methylthio, ethylthio, propylthio, 1-methylethylthio, butylthio, 1-methylpropylthio, 2-methylpropylthio or 1,1-dimethylethylthio radical, d) an optionally substituted —O-alkylenearyl radical, such as —O-benzyl, e) $R_T^1$ is further a radical —$(O)_m$—$N(R^{18})(R^{19})$, in which m is 0 or 1 and $R^{18}$ and $R^{19}$, which can be identical or different, have the following meanings:

hydrogen, a branched or unbranched, optionally substituted $C_1$-$C_6$-alkyl radical, such as methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl or the corresponding substituted radicals, preferably methyl, ethyl, propyl, butyl or i-butyl, $C_2$-$C_6$-alkenyl radical, such as vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl or the corresponding substituted radicals, $C_2$-$C_6$-alkynyl radical, such as ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl or 1-methyl-2-butynyl or the corresponding substituted radicals, $C_3$-$C_8$-cycloalkyl, such as cyclopropyl, cyclobutyl, cyclopentyl, cyclohexyl and cycloheptyl, cyclooctyl or the corresponding substituted radicals, or a phenyl radical, optionally mono- or polysubstituted, for example mono- to trisubstituted, by halogen, nitro, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio such as 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl, or $R^{18}$ and $R^{19}$ together form an optionally substituted, e.g. $C_1$-$C_4$-alkyl-substituted, $C_4$-$C_7$-alkylene chain closed to give a cycle, which can contain a heteroatom selected from the group consisting of oxygen, sulfur and nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_2)_3$—, —NH—$(CH_2)_3$—, —$CH_2$—NH—$(CH_2)_2$—, —$CH_2$—CH=CH—$CH_2$—, —CH=CH—$(CH_2)_3$—, —CO—$(CH_2)_2$—CO— or —CO—$(CH_2)_3$—CO—.

A radical bioisosteric to COOH is understood as meaning radicals which can replace the function of a group COOH in active compounds by equivalent bond donor/acceptor capabilities or by equivalent charge distribution.

Radicals which may be mentioned by way of example as radicals bioisosteric to —COOH are those such as described in "The Practice of Medicinal Chemistry, Editor: C.G. Wermuth, Academic Press 1996, pages 125 and 216, in particular the radicals —P=O(OH)$_2$, —SO$_3$H, tetrazole or acylsulfonamides.

Preferred radicals T are —COOH, —CO—O—$C_1$-$C_8$-alkyl or —CO—O—benzyl.

The radical —U— in the structural element L is a spacer selected from the group —$(X_L)_a$—$(CR_L^1R_L^2)_b$—, —$CR_L^1$=$CR_L^2$—, ethynylene or 40=$CR_L^1$—. In the case of the radical =$CR_L^1$—, the structural element L is linked to the structural element G via a double bond.

$X_L$ is a radical $CR_L^3R_L^4$, $NR_L^5$, oxygen or sulfur.

Preferred radicals —U— are the radicals —$CR_L^1$=$CR_L^2$—, ethynylene or $(X_L)_a$—$(CR_L^1R_L^2)_b$—, wher $X_L$ is preferably $CR_L^3R_L^4$ (a=0 or 1) or oxygen (a=1).

Particularly preferred radicals —U— are the radicals —$(X_L)_a$—$(CR_L^1R_L^2)_b$—, where $X_L$ is preferably $CR_L^3R_L^4$ (a=0 or 1) or oxygen (a=1).

Under $R_L^1$, $R_L^2$, $R_L^3$ or $R_L^4$ in structural element L, a halogen radical is understood as meaning, for example, F, Cl, Br or I, preferably F.

Under $R_L^1$, $R_L^2$, $R_L^3$ or $R_L^4$ in structural element L, a branched or unbranched $C_1$-$C_6$-alkyl radical is understood as meaning, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably branched or unbranched $C_1$-$C_4$-alkyl radicals such as methyl, ethyl, propyl, 1-methylethyl, butyl, 1-methylpropyl, 2-methylpropyl or 1,1-dimethylethyl, particularly preferably methyl.

Under $R_L^1$, $R_L^2$, $R_L^3$ or $R_L^4$ in structural element L, a branched or unbranched $C_2$-$C_6$-alkenyl radical is understood as meaning, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

Under $R_L^1$, $R_L^2$, $R_L^3$ or $R_L^4$ in structural element L, a branched or unbranched $C_2$-$C_6$-alkynyl radical is understood as meaning, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3- butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, 1-methyl-2-propynyl or 1-methyl-2-butynyl.

Under $R_L^1$, $R_L^2$, $R_L^3$ or $R_L^4$ in structural element L, a branched or unbranched $C_3$-$C_7$-cycloalkyl radical is understood as meaning, for example, cyclopropyl, cyclobutyl, cyclopentyl, cyclohexyl or cycloheptyl.

Under $R_L^1$, $R_L^2$, $R_L^3$ or $R_L^4$ in structural element L, a branched or unbranched $C_1$-$C_4$-alkoxy radical is understood as meaning, for example, methoxy, ethoxy, propoxy, 1-methylethoxy, butoxy, 1-methylpropoxy, 2-methylpropoxy or 1,1-dimethylethoxy.

The radicals —CO—NH($C_1$-$C_6$-alkyl), —CO—N($C_1$-$C_6$-alkyl)$_2$ are secondary or tertiary amides and are composed of the amide bond and the corresponding $C_1$-$C_6$-alkyl radicals such as described above for $R_L^1$, $R_L^2$, $R_L^3$ or $R_L^4$.

The radicals $R_L^1$, $R_L^2$, $R_L^3$ or $R_L^4$ can furthermore be a radical
$C_1$-$C_2$-alkylene-T, such as methylene-T or ethylene-T, C2-alkenylene-T, such as ethenylene-T or $C_2$-alkynylene-T, such as ethynylene-T,
an aryl radical, such as phenyl, 1-naphthyl or 2-naphthyl or
an arylalkyl radical, such as benzyl or ethylenephenyl (homobenzyl),
where the radicals can optionally be substituted.

Furthermore, two radicals $R_L^1$ and $R_L^2$ or $R_L^3$ and $R_L^4$ or optionally $R_L^1$ and $R_L^3$ can in each case independently of one another together be an optionally substituted 3- to 7-membered saturated or unsaturated carbocycle or heterocycle, which can contain up to three different or identical heteroatoms O, N, S.

All radicals for $R_L^1$, $R_L^2$, $R_L^3$ or $R_L^4$ can be optionally substituted. For the radicals $R_L^1$, $R_L^2$, $R_L^3$ or $R_L^4$ and all further substituted radicals of the description below, suitable substituents, if the substituents are not specified in greater detail, are independently of one another up to 5 substituents, for example selected from the following group:
—NO$_2$, —NH$_2$, —OH, —CN, —COOH, —O—CH$_2$—COOH, halogen, a branched or unbranched, optionally substituted $C_1$-$C_4$-alkyl radical, such as methyl, CF$_3$, $C_2F_5$ or CH$_2$F, —CO—O—$C_1$-$C_4$-alkyl, $C_3$-$C_6$-cycloalkyl, $C_1$-$C_4$-alkoxy, $C_1$-$C_4$-thioalkyl, —NH—CO—O—$C_1$-$C_4$-alkyl, —O—CH$_2$—COO—$C_1$-$C_4$-alkyl, —NH—CO—$C_1$-$C_4$-alkyl, —CO—NH—$C_1$-$C_4$-alkyl, —NH—SO$_2$—$C_1$-$C_4$-alkyl, —SO$_2$—NH—$C_1$-$C_4$-alkyl, —N($C_1$-$C_4$-alkyl)$_2$, —NH—$C_1$-$C_4$-alkyl, or —SO$_2$—$C_1$-$C_4$-alkyl radical, such as —SO$_2$—CF$_3$, an optionally substituted —NH—CO-aryl, —CO—NH-aryl, —NH—CO—O-aryl, —NH—CO—O-alkylenearyl, —NH—SO$_2$-aryl, —SO$_2$—NH-aryl, —CO—NH-benzyl, —NH—SO$_2$-benzyl or —SO$_2$—NH-benzyl radical, an optionally substituted radical —SO$_2$—NR$^5{}^2$R$^5{}^3$ or —CO—NR$^5{}^2$RS$^3$ where the radicals R$^2$ and R$^3$ independently of one another can have the meaning $R_L^5$ as below or both radicals R$^2$ and R$^3$ together can be a 3- to 6-membered, optionally substituted, saturated, unsaturated or aromatic heterocycle which, in addition to the ring nitrogen, can contain up to three further different or identical heteroatoms O, N, S, and optionally two radicals substituted on this heterocycle can together be a fused, saturated, unsaturated or aromatic carbocycle or heterocycle which can contain up to three different or identical heteroatoms O, N, S and the cycle can be optionally substituted or a further, optionally substituted cycle can be fused to this cycle.

If not specified in greater detail, in all terminally bonded, substituted hetaryl radicals of the description, two substituents can form a fused 5- to 7-membered, unsaturated or aromatic carbocycle.

Preferred radicals $R_L^1$, $R_L^2$, $R_L^3$ or $R_L^4$ are independently of one another hydrogen, halogen, a branched or unbranched, optionally substituted $C_1$-$C_4$-alkyl, $C_1$-$C_4$-alkoxy or $C_3$-$C_7$-cycloalkyl radical or the radical —NR$_L^6$R$_L^7$.

Particularly preferred radicals $R_L^1$, $R_L^2$, $R_L^3$ or $R_L^4$ are independently of one another hydrogen, fluorine or a branched or unbranched, optionally substituted $C_1$-$C_4$-alkyl radical, preferably methyl.

The radicals $R_L^5$, $R_L^6$, $R_L^7$ in structural element L are independently of one another hydrogen, a branched or unbranched, optionally substituted
$C_1$-$C_6$-alkyl radical, for example as described above for $R_L^1$,
$C_3$-$C_7$-cycloalkyl radical, for example as described above for $R_L^1$,
CO—O—$C_1$-$C_6$-alkyl, SO$_2$—$C_1$-$C_6$-alkyl or CO—$C_1$-$C_6$-alkyl radical, which is composed of the group CO—O, SO$_2$ or CO and, for example, of the $C_1$-$C_6$-alkyl radicals described above for $R_L^1$,
or an optionally substituted CO—O-alkylenearyl, SO$_2$-aryl, SO$_2$-alkylenearyl or CO-alkylenearyl radical, which is composed of the group CO—O, SO$_2$ or CO and, for example, of the aryl or arylalkyl radicals described above for $R_L^1$.

Preferred radicals for $R_L^6$ in structural element L are hydrogen, a branched or unbranched, optionally substituted $C_1$-$C_4$-alkyl, CO—O—$C_1$-$C_4$-alkyl, CO—$C_1$-$C_4$-alkyl or SO$_2$—$C_1$-$C_4$-alkyl radical or an optionally substituted CO—O-benzyl, SO$_2$-aryl, SO$_2$-alkylenearyl or CO-aryl radical.

Preferred radicals for $R_L^7$ in structural element L are hydrogen or a branched or unbranched, optionally substituted $C_1$-$C_4$-alkyl radical.

Preferred structural elements L are composed of the preferred radicals of the structural element.

Particularly preferred structural elements L are composed of the particularly preferred radicals of the structural element.

G is a structural element of the formula $I_G$

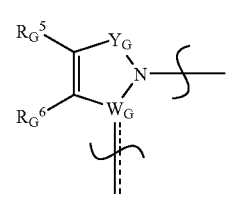

where the incorporation of the structural element G can take place in both orientations. Preferably, the incorporation of the structural element G into the compounds of the formula I can take place such that the structural element B is bonded via the ring nitrogen and the structural element L is bonded via $W_G$ to the structural element G, optionally via a double bond.

$Y_G$ in structural element G is CO, CS, C=NR$_G^2$ or CR$_G^3$R$_G^4$, preferably CO, C=NR$_G^2$ or CR$_G^3$R$_G^4$, particularly preferably CO or CR$_G^3$R$_G^4$.

$R_G^2$ in structural element G is hydrogen, a hydroxyl group, a branched or unbranched, optionally substituted $C_1$-$C_6$-alkyl, $C_1$-$C_4$-alkoxy or $C_3$-$C_7$-cycloalkyl radical, for example as described above for $R_L^1$ in each case, an optionally substituted —O—$C_3$-$C_7$-cycloalkyl radical, which is composed of an ether group and, for example, of the $C_3$-$C_7$-cycloalkyl radical described above for $R_L^1$, an optionally substituted aryl or arylalkyl radical, for example as described above for $R_L^1$ in each case or an optionally substituted —O-aryl or —O-alkylenearyl radical, which is composed of a group —O— and, for example, of the aryl or arylalkyl radicals described above for $R_L^1$.

Preferred radicals $R_G^2$ in structural element G are hydrogen, hydroxyl or a branched or unbranched, optionally substituted $C_1$-$C_6$-alkyl radical, in particular methyl or $C_1$-$C_4$-alkoxy radical, in particular methoxy.

Branched or unbranched, optionally substituted $C_1$-$C_6$-alkyl, $C_2$-$C_6$-alkenyl, $C_2$-$C_6$-alkynyl or $C_1$-$C_4$-alkoxy radicals for $R_G^3$ or $R_G^4$ in structural element G independently of one another are understood as meaning, for example, the corresponding radicals in each case described above for $R_L^1$.

Further, both radicals $R_G^3$ and $R_G^4$ can together form a cyclic acetal, such as —O—$CH_2$—$CH_2$—O— or —O—$CH_2$—O—.

Furthermore, both radicals $R_G^3$ and $R_G^4$ can together form an optionally substituted $C_3$-$C_7$-cycloalkyl radical.

Preferred radicals for $R_G^3$ or $R_G^4$ are independently of one another hydrogen, $C_1$-$C_6$-alkyl or $C_1$-$C_4$-alkoxy, and both radicals $R_G^3$ and $R_G^4$ together form a cyclic acetal, such as —O—$CH_2$—$CH_2$—O— or —O—$CH_2$—O—. Particularly preferred radicals $R_G^3$ or $R_G^4$ are independently of one another hydrogen and both radicals $R_G^3$ and $R_G^4$ together form a cyclic acetal, in particular —O—$CH_2$—$CH_2$—O— or —O—$CH_2$—O—.

Branched or unbranched, optionally substituted $C_1$-$C_6$-alkyl or $C_1$-$C_4$-alkoxy radicals and optionally substituted aryl or arylalkyl radicals for $R_G^5$ and $R_G^6$ in structural element G independently of one another are, for example, the corresponding radicals in each case described above for $R_L^1$.

Further, both radicals $R_G^5$ and $R_G^6$ can together form an optionally substituted, fused, unsaturated or aromatic 3- to 10-membered carbocycle or heterocycle, which can contain up to three different or identical heteroatoms O, N, S, where in this fused, unsaturated or aromatic 3- to 10-membered carbocycle or heterocycle, as substituents, independently of one another up to four substituents from the group hydroxyl, halogen, such as F or Cl or a branched or unbranched, optionally halogen-substituted $C_1$-$C_4$-alkoxy radical, such as methoxy, $C_1$-$C_4$-thioalkyl or $C_1$-$C_4$-alkyl radical, such as methyl, ethyl, propyl or butyl, or an optionally halogen-substituted aryl radical, such as phenyl, hetaryl, such as described below for $RG^7$, or $C_3$-$C_7$-cycloalkyl radical, such as described below for $R_G^7$, or an optionally halogen-substituted radical —$SO_2$—$C_1$-$C_4$-alkyl, —SO—$C_1$-$C_4$-alkyl, —$SO_2$—$C_1$-$C_4$-alkylenearyl, —SO—$C_1$-$C_4$-alkylenearyl, —$SO_2$-aryl or —SO-aryl are selected.

Preferred substituents are halogen, a $C_1$-$C_4$-alkyl radical, $C_1$-$C_4$-alkoxy radical or aryl radical.

Particularly preferred substituents are a $C_1$-$C_4$-alkyl radical, in particular methyl or ethyl, a $C_1$-$C_4$-alkoxy radical, in particular methoxy, or F or Cl.

Preferred radicals for $R_G^5$ and $R_G^6$ are independently of one another hydrogen, an optionally substituted $C_1$-$C_6$-alkyl radical, in particular methyl and ethyl, an optionally substituted aryl radical, in particular optionally substituted phenyl or an optionally substituted arylalkyl radical, in particular an optionally substituted benzyl radical, and in each case both radicals $R_G^5$ and $R_G^6$ together can be an optionally substituted, fused, unsaturated or aromatic 3- to 10-membered carbocycle or heterocycle which can contain up to three different or identical heteroatoms O, N, S.

In particularly preferred radicals for $R_G^5$ and $R_G^6$, both radicals $R_G^5$ and $R_G^6$ together form an optionally substituted, fused, unsaturated or aromatic 3- to 6-membered carbocycle or heterocycle, for example selected from one of the following doubly bonded structural formulae:

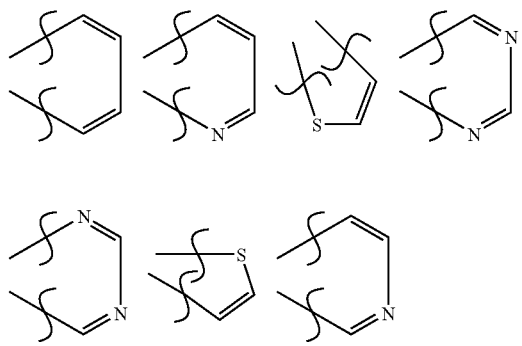

in particular selected from one of the following, doubly bonded structural formulae:

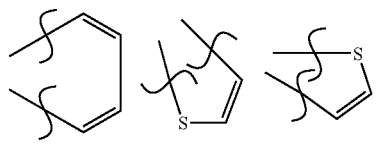

$W_G$ is a structural element selected from the group of structural elements of the formulae $I_{WG}^1$ to $I_{WG}^4$, where the dashed lines intersect the atomic bonds within the structural element G and the carbon atom substituted by $R_G^7$ and $R_G^8$ is bonded to $Y_G$.

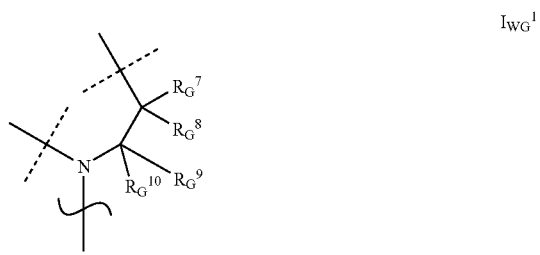

$I_{WG}^1$

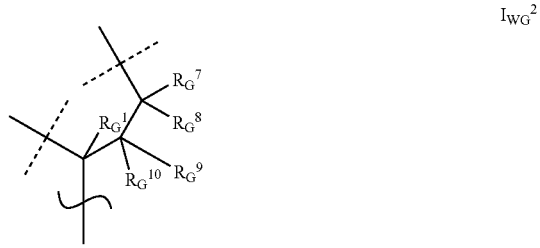

$I_{WG}^2$

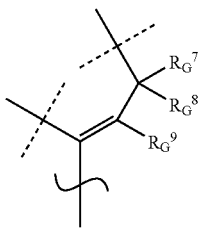

$I_{WG}^3$

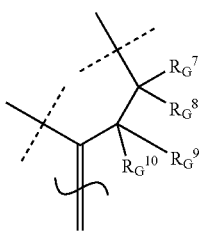

$I_{WG}^4$

In a preferred embodiment, $W_G$ is a structural element selected from the group of structural elements of the formulae $I_{WG}^1$, $I_{WG}^2$ and $I_{WG}^4$, in particular the structural element of the formula $IWG^2$.

$R_G^1$ in structural element $W_G$ is hydrogen, halogen, such as Cl, F, Br or I, a hydroxyl group or a branched or unbranched, optionally substituted $C_1$-$C_6$-alkyl radical, preferably $C_1$-$C_4$-alkyl or $C_1$-$C_4$-alkoxy radical such as in each case described above for $R_L^1$.

Preferred radicals for $R_G^1$ are hydrogen, hydroxyl and optionally substituted $C_1$-$C_4$-alkyl or $C_1$-$C_4$-alkoxy radicals.

Particularly preferred radicals for $R_G^1$ are hydrogen and carboxyl-substituted $C_1$-$C_4$-alkyl or $C_1$-$C_4$-alkoxy radicals, in particular the radicals —$CH_2COOH$ or —O—$CH_2COOH$.

$R_G^7$, $R_G^8$, $R_G^9$ and $R_G^{10}$ in structural element G are independently of one another hydrogen, a hydroxyl group, CN, halogen, such as F, Cl, Br, I, a branched or unbranched, optionally substituted $C_1$-$C_6$-alkyl radical, such as optionally substituted methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, $C_2$-$C_6$-alkenyl radical, such as optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, $C_2$-$C_6$-alkynyl radical, such as optionally substituted ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, an optionally substituted $C_3$-$C_7$-cycloalkyl radical, such as optionally substituted cyclopropyl, cyclobutyl, cyclopentyl, cyclohexyl or cycloheptyl, $C_3$-$C_7$-heterocycloalkyl radical, such as optionally substituted aziridinyl, diaziridinyl, oxiranyl, oxaziridinyl, oxetanyl, thiiranyl, thietanyl, pyrrolidinyl, piperazinyl, morpholinyl, piperidinyl, tetrahydrofuranyl, tetrahydropyranyl, 1,4-dioxanyl, hexahydroazepinyl, oxepanyl, 1,2-oxathiolanyl or oxazolidinyl, $C_3$-$C_7$-heterocycloalkenyl radical, such as optionally substituted azirinyl, diazirinyl, thiirenyl, thietyl, pyrrolinyls, oxazolinyls, azepinyl, oxepinyl, α-pyranyl, β-pyranyl, γ-pyranyl, dihydropyranyls, 2,5-dihydropyrrolinyl or 4,5-dihydrooxazolyl, a branched or unbranched, optionally substituted $C_1$-$C_4$-alkylene-$C_3$-$C_7$-cycloalkyl radical, which is composed, for example, of branched or unbranched $C_1$-$C_4$-alkylene radicals such as methylene, ethylene, propylene, n-butylene, isobutylene or t-butylene and, for example, the abovementioned $C_3$-$C_7$-cycloalkyl radicals, a branched or unbranched optionally substituted $C_1$-$C_4$-alkylene-$C_3$-$C_7$-heterocycloalkyl or $C_1$-$C_4$-alkylene-$C_3$-$C_7$-heterocycloalkenyl radical, which is composed of optionally substituted $C_1$-$C_4$-alkylene radicals, such as methylene, ethylene, propylene, n-butylene, isobutylene or t-butylene and, for example, the above-mentioned $C_3$-$C_7$-heterocycloalkyl or $C_3$-$C_7$-heterocycloalkenyl radicals, the radicals being preferred which in the cyclic moiety contain one or two heteroatoms selected from the group consisting of N, O and S and up to two double bonds, a branched or unbranched, optionally substituted radical $C_1$-$C_4$-alkylene-O-$R_G^{11}$, $C_1$-$C_4$-alkylene-CO-O$R_G^{11}$, $C_1$-$C_4$-alkylene-O—CO-$R_G^{11}$, $C_1$-$C_4$-alkylene-CO-$R_G^{11}$, $C_1$-$C_4$-alkylene-$SO_2$—N$R_G^{12}R_G^{13}$, $C_1$-$C_4$-alkylene-CO—N$R_G^{12}$, $R_G^3$, $C_1$-$C_4$-alkylene-O—CO—N$R_G^{12}R_G^{13}$, $C_1$-$C_4$-alkylene-N$R_G^{12}R_G^{13}$, $C_1$-$C_4$-alkylene-S$R_G^{11}$ or $C_1$-$C_4$-alkylene-SO—$R_G^{11}$ which is composed of branched or unbranched, optionally substituted $C_1$-$C_4$-alkylene radicals, such as methylene, ethylene, propylene, n-butylene, isobutylene or t-butylene, the corresponding groups —O—, —CO—, —S—, —N and the terminal radicals $R_G^{11}$, $R_G^{12}$ and $R_G^{13}$ described below, an optionally substituted aryl radical, preferably optionally substituted phenyl, 1-naphthyl or 2-naphthyl, arylalkyl radical, preferably optionally substituted benzyl or ethylenephenyl(homobenzyl), hetaryl radical, preferably optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their fused derivatives such as indazolyl, indolyl, benzothiophenyl, benzofuranyl, indolinyl, benzimidazolyl, benzothiazolyl, benzoxazolyl, quinolinyl or isoquinolinyl, hetarylalkyl radical, preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, —$CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, 10-$CH_2$—$CH_2$-2-thiazolyl, —$CH_2$—$CH_2$-4-thiazolyl or —$CH_2$—$CH_2$-5-thiazolyl or a radical —$S—R^{11}$, —$O—R_G^{11}$, —$SO-R_G^{11}$, —$SO_2—R_G^{11}$, —$CO—OR_G^{11}$, —$O—CO-R_G^{11}$, —$O—CO—NR_G^{12}R_G^{13}$, —$SO_2—NR_G^{12}R_G^{13}$, —$CO—NR_G^{12}R_G^{13}$, —$NR_G^{12}R_G^{13}$, $CO—R_G^{11}$.

Further, two radicals $R_G^7$ and $R_G^9$ or $R_G^8$ and $R_G^{10}$ or $R_G^7$ and $R_G^8$ or $R_G^9$ and $R_G^{10}$ can in each case independently of one another together form an optionally substituted, saturated or unsaturated, nonaromatic, 3- to 7-membered carbocycle or heterocycle which can contain up to 3 heteroatoms selected from the group consisting of O, N, S and up to two double bonds.

Preferred radicals for $R_G^7$, $R_G^8$, $R_G^9$ and $R_G^{10}$ in the structural element G are independently of one another hydrogen, halogen, in particular a branched or unbranched, optionally substituted $C_1$-$C_6$-alkyl, or $C_2$-$C_6$-alkynyl radical, a branched or unbranched, optionally substituted radical $C_1$-$C_4$-alkylene-$OR_G^{11}$, $C_1$-$C_4$-alkylene-$CO—OR_G^{11}$, $C_1$-$C_4$-alkylene-O—$CO-R_G^{11}$, $C_1$-$C_4$-alkylene-$CO—NR_G^{12}R_G^{13}$, $C_1$-$C_4$-alkylene-O—$CO—NR_G^{12}R_G^{13}$, a radical —$O-R_G^{11}$, —$CO—OR_G^{11}$, —$O—CO—R_G^{11}$, —$O—CO—NR_G^{12}R_G^{13}$, —$CO—NR_G^{12}R_G^{13}$, —$NR_G^{12}R_G^{13}$ or $CO—R_G^{11}$, an optionally substituted aryl, hetaryl or arylalkyl radical, as described above in each case.

Particularly preferred radicals for $R_G^7$ $R_G^8$, $R_G^9$ and $R_G^{10}$ in the structural element G are independently of one another hydrogen, F, a radical —$CO—OR_G^{11}$, —$CO—NR_G^{12}R_G^{13}$, or an optionally substituted aryl radical, as described above in each case.

A branched or unbranched, optionally substituted $C_1$-$C_8$-alkyl radical for $R_G^{11}$, $R_G^{12}$ and $R_G^{13}$ is understood as meaning independently of one another, for example, the $C_1$-$C_6$-alkyl radicals mentioned above for $R_G^1$, plus the radicals heptyl and octyl.

Preferred substituents of the branched or unbranched, optionally substituted $C_1$-$C_8$-alkyl radicals for $R_G^{11}$, $R_G^{12}$ and $R_G^{13}$ independently of one another are the radicals halogen, hydroxyl, $C_1$-$C_4$-alkoxy, —CN, —COOH and —CO—O—$C_1$-$C_4$-alkyl.

A branched or unbranched, optionally substituted $C_2$-$C_6$-alkenyl, $C_2$-$C_6$-alkynyl or $C_1$-$C_4$-alkylene-$C_3$-$C_7$-cycloalkyl radical, an optionally substituted $C_3$-$C_7$-cycloalkyl, aryl, arylalkyl, hetaryl or hetarylalkyl radical for $R_G^{11}$, $R_G^{12}$ and $R_G^{13}$ independently of one another is understood as meaning, for example, the corresponding radicals mentioned above for $R_G^1$.

Preferred branched or unbranched, optionally substituted —$C_1$-$C_5$-alkylene-$C_1$-$C_4$-alkoxy radicals for $R_G^{11}$, $R_G^{12}$ and $R_G^{13}$ are independently of one another methoxymethylene, ethoxymethylene, t-butoxymethylene, methoxyethylene or ethoxyethylene.

Preferred branched or unbranched, optionally substituted mono- and bisalkylaminoalkylene or acylaminoalkylene radicals for $R_G^{11}$, $R_G^{12}$ and $R_G^{13}$ are independently of one another branched or unbranched, optionally substituted radicals —$C_1$-$C_4$-alkylene-$NH(C_1$-$C_4$-alkyl), —$C_1$-$C_4$-alkylene-$N(C_1$-$C_4$-alkyl$)_2$ or —$C_1$-$C_4$-alkylene-NH—CO—$C_1$-$C_4$-alkyl.

Preferred optionally substituted heterocycloalkyl, heterocycloalkenyl, $C_1$-$C_4$-alkyleneheterocycloalkyl or $C_1$-$C_4$-alkyleneheterocycloalkenyl radicals for $R_G^{11}$, $R_G^{12}$ and $R_G^{13}$ are independently of one another the $C_3$-$C_7$-heterocycloalkyl, $C_3$-$C_7$-heterocycloalkenyl, $C_1$-$C_4$-alkylene-$C_3$-$C_7$-heterocycloalkyl or $C_1$-$C_4$-alkylene-$C_3$-$C_7$-heterocycloalkenyl radicals described above for $R_G^1$.

Particularly preferred, optionally substituted heterocycloalkyl, heterocycloalkenyl, $C_1$-$C_4$-alkyleneheterocycloalkyl or $C_1$-$C_4$-alkyleneheterocycloalkenyl radicals for $R_G^{11}$, $R_G^{12}$ and $R_G^{13}$ are independently of one another the $C_3$-$C_7$-heterocycloalkyl, $C_3$-$C_7$-heterocycloalkenyl, $C_1$-$C_4$-alkylene-$C_3$-$C_7$-heterocycloalkyl or $C_1$-$C_4$-alkylene-$C_3$-$C_7$-heterocycloalkenyl radicals described above for $R_G^1$, one or two heteroatoms being selected from the group consisting of N, O and S and up to two double bonds being contained in the cyclic moiety.

Further, $R_G^{12}$ and $R_G^{13}$ can independently of one another be a radical —$SO_2—R_G^{11}$, —$CO—O-R_G^{11}$, —$CO—NR^{G11}R_G^{11*}$ or —$CO-R_G^{11}$, $R_G^{11*}$ being a radical $R_G^{11}$ which is independent of $R_G^{11}$.

Furthermore, both radicals $R_G^{12}$ and $R_G^{13}$ can together form a 5- to 7-membered, preferably saturated nitrogen-containing carbocycle, in the sense of a cyclic amine structure, such as N-pyrrolidinyl, N-piperidinyl, N-hexahydroazepinyl, N-morpholinyl or N-piperazinyl, where in the case of heterocycles which carry free amine protons, such as N-piperazinyl, the free amine protons can be replaced by customary amine protective groups, such as methyl, benzyl, Boc (tert-butoxycarbonyl), Z (benzyloxycarbonyl), tosyl, —$SO_2$—$C_1$-$C_4$-alkyl, —$SO_2$-phenyl or —$SO_2$-benzyl.

Particularly preferred radicals for $R_G^{11}$ are hydrogen or an optionally substituted $C_1$-$C_4$-alkyl or aryl radical.

Particularly preferred radicals for $R_G^{12}$ and $R_G^{13}$ are independently of one another hydrogen or an optionally substituted $C_1$-$C_4$-alkyl radical.

Preferred structural elements G are composed of at least one preferred radical of the structural element G, while the remaining radicals are widely variable.

Particularly preferred structural elements G are composed of the preferred radicals of the structural element G.

Very particularly preferred structural elements G are composed of the particularly preferred radicals of the structural element G.

Structural element B is understood as meaning a structural element comprising at least one atom which under physiological conditions can form hydrogen bridges as a hydrogen acceptor, at least one hydrogen acceptor atom having a distance of 4 to 15 atom bonds to structural element G along the shortest possible route along the structural element skeleton. The arrangement of the structural skeleton of structural element B is widely variable.

Suitable atoms which under physiological conditions can form hydrogen bridges as hydrogen acceptors are, for example, atoms having Lewis base properties, such as the heteroatoms nitrogen, oxygen or sulfur.

Physiological conditions is understood as meaning a pH which prevails at the site in a body at which the ligands interact with the receptors. In the present case, the physiological conditions have a pH of, for example, 5 to 9.

In a preferred embodiment, structural element B is a structural element of the formula $I_B$ $$A-E- \qquad I_B$$

where A and E have the following meanings:

A is a structural element selected from the group:
- a 4- to 8-membered monocyclic saturated, unsaturated or aromatic hydrocarbon which can contain up to 4 heteroatoms selected from the group O, N and S, where, in each case independently of one another, the ring nitrogen optionally contained or the carbons can be substituted, with the proviso that at least one heteroatom selected from the group O, N and S contained in the structural element A,
or
- a 9- to 14-membered polycyclic, saturated, unsaturated or aromatic hydrocarbon which can contain up to 6 heteroatoms selected from the group N, O and S, where, in each case independently of one another, the ring nitrogen optionally contained or the carbons can be substituted, with the proviso that at least one heteroatom selected from the group O, N and S is contained in the structural element A,
- a radical

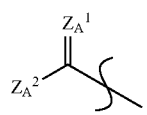

where
$Z_A^1$ is oxygen, sulfur or optionally substituted nitrogen and
$Z_A^2$ is optionally substituted nitrogen, oxygen or sulfur,
or a radical

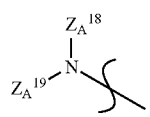

where
$R_A^{18}$, $R_A^{19}$
independently of one another are hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bis-alkylaminoalkylene or acylaminoalkylene radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical $-SO_2-R_G^{11}$, $-CO-OR_G^{11}$, $-CO-NR^{11}R_G^{11*}$ or $-CO-R_G^{11}$
and
E is a spacer structural element which covalentily bonds the structural element A to the structural element G, where the number of atom bonds along the shortest possible route along the structural element skeleton E is 3 to 14.

In a particularly preferred embodiment, the structural element A is a structural element selected from the group of structural elements of the formulae $I_A^1$ to $I_A^{18}$,

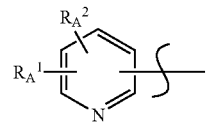 $I_A^1$

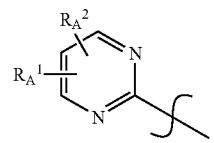 $I_A^2$

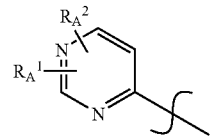 $I_A^3$

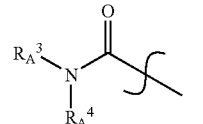 $I_A^4$

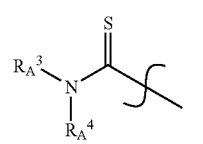 $I_A^5$

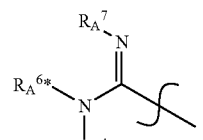 $I_A^6$

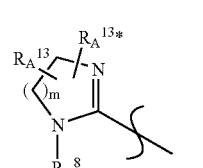 $I_A^7$

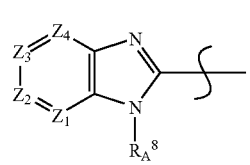 $I_A^8$

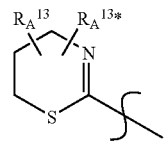 $I_A^9$

-continued

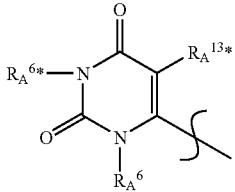
$I_A^{10}$

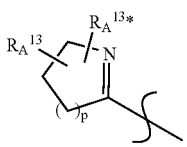
$I_A^{11}$

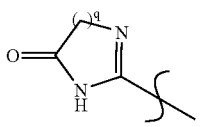
$I_A^{12}$

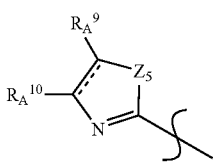
$I_A^{13}$

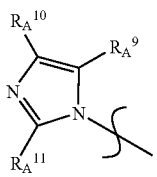
$I_A^{14}$

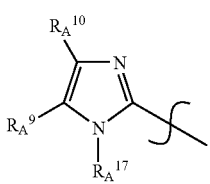
$I_A^{15}$

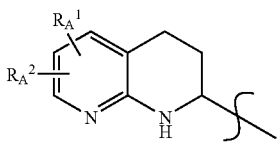
$I_A^{16}$

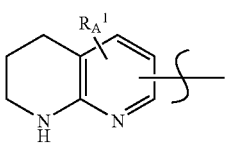
$I_A^{17}$

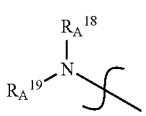
$I_A^{18}$ where
m,p,q
independently of one another are 1, 2 or 3, $R_A^1$, $R_A^2$
independently of one another are hydrogen, CN, halogen, a branched or unbranched, optionally substituted $C_1$-$C_{1-6}$-alkyl or CO—$C_1$-$C_6$-alkyl radical or an optionally substituted aryl, arylalkyl, hetaryl, hetarylalkyl or $C_3$-$C_7$-cycloalkyl radical or a radical CO—O-$R_A^{14}$, O-$R_A^{14}$, S-$R_A^{14}$, $NR_A^{15}R_A^{16}$, CO—$NR_A^{15}R_A^{16}$ or $SO_2NR_A^{15}R_A^{16}$ or both radicals $R_A^1$ and $R_A^2$ together are a fused, optionally substituted, 5- or 6-membered, unsaturated or aromatic carbocycle or heterocycle which can contain up to three heteroatoms selected from the group O, N, and S, $R_A^{13}$, $R_A^{13*}$
independently of one another are hydrogen, CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO—O-$R_A^{14}$, O-$R_A^{14}$, S-$R_A^{14}$, $NR_A^{15}R_A^{16}$, $SO^2$—$NR_A^{15}R_A^{16}$ or CO—$NR_A^{15}R_A^{16}$, where
$R_A^{14}$ is hydrogen, a branched or unbranched, optionally substituted $C_1$-$C_6$-alkyl, alkylene-$C_1$-$C_4$-alkoxy, $C_2$-$C_6$-alkenyl, $C_2$-$C_6$-alkynyl or $C_1$-$C_6$-alkylene-$C_3$-$C_7$-cycloalkyl radical or an optionally substituted $C_3$-$C_7$-cycloalkyl, aryl, arylalkyl, hetaryl or hetarylalkyl radical, $R_A^{15}$, $R_A^{16}$,
independently of one another are hydrogen, a branched or unbranched, optionally substituted $C_1$-$C_6$-alkyl, CO—$C_1$-$C_6$-alkyl, $SO_2$—$C_1$-$C_6$-alkyl, COO—$C_1$-$C_6$-alkyl, CO—NH—$C_1$-$C_6$-alkyl, arylalkyl, COO-alkylenearyl, $SO_2$-alkylenearyl, CO—NH-alkylenearyl, CO—NH-alkylenehetaryl or hetarylalkyl radical or an optionally substituted $C_3$-$C_7$-cycloalkyl, aryl, CO-aryl, CO—NH-aryl, $SO_2$-aryl, hetaryl, CO—NH-hetaryl or CO-hetaryl radical, $R_A^3$, $R_A^4$
independently of one another are hydrogen, —$(CH_2)_n$—$(X_A)_j$—$R_A^{12}$, or both radicals together are a 3- to 8-membered, saturated, unsaturated or aromatic N-heterocycle which can additionally contain two further, identical or different heteroatoms O, N or S, where the cycle is optionally substituted or a further, optionally substituted, saturated, unsaturated or aromatic cycle can be fused to this cycle, where
n is 0, 1, 2 or 3,
j is 0 or 1,
$X_A$ is —CO—, —CO—N($R_X^1$)—, —N($R_X^1$)-CO—, —N($R_X^1$)—CO—N($R_X^{1*}$)—, —N($R_X^1$)—CO—O—, —O—, —S—, —$SO_2$—, —$SO_2$—N($R_X^1$)—, —$SO_2$—O—, —CO—O—, —O—CO—, —O—CO—N($R_X^1$)—, —N($R_X^1$)— or —N($R_X^1$)—$SO_2$—, $R_A^{12}$ is hydrogen, a branched or unbranched, optionally substituted $C_1$-$C_6$-alkyl radical, an optionally $C_1$-$C_4$-alkyl- or aryl-substituted $C_2$-$C_6$-alkynyl or $C_2$-$C_6$-alkenyl radical or a 3- to 6-membered, saturated or unsaturated heterocycle, substituted by up to three identical or different radicals, which can contain up to three different or identical heteroatoms O, N, S, a $C_3$-$C_7$-cycloalkyl, aryl or hetaryl radical, where two radicals together can be a fused, saturated, unsaturated or aromatic carbocycle or heterocycle which can contain up to three different or identical heteroatoms O, N, S and the cycle can optionally be substituted or a further, optionally substituted, saturated, unsaturated or aromatic cycle can be fused to this cycle, or the radical $R_A^{12}$, together with $R_X^1$ or $R_X^{1*}$ forms a saturated or unsaturated $C_3$-$C_7$-heterocycle which can optionally contain up to two further heteroatoms selected from the group O, S and N, $R_X^1$, $R_X^{1*}$
independently of one another are hydrogen, a branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl, CO—$C_1$-$C_6$-alkyl, CO—O—$C_1$-$C_6$-alkyl or $SO_2$—$C_1$-$C_6$-alkyl radical or an optionally substituted $C_3$-$C_7$-cycloalkyl, aryl, arylalkyl, CO—O-alkylenearyl, CO-alkylenearyl, CO-aryl, $SO_2$-aryl, hetaryl, CO-hetaryl or $SO_2$-alkylenearyl radical, $R_A^6$, $R_A^{6*}$
are hydrogen, a branched or unbranched, optionally substituted $C_1$-$C_4$-alkyl, —CO—O—$C_1$-$C_4$-alkyl, arylalkyl, —CO—O-alkylenearyl, —CO—O-allyl, —CO—$C_1$-$C_4$-alkyl, —CO-alkylenearyl, $C_3$-$C_7$-cycloalkyl or —CO-allyl radical or in structural element $I_A^7$ both radicals $R_A^6$ and $R_A^{6*}$ together are an optionally substituted, saturated, unsaturated or aromatic heterocycle which, in addition to the ring nitrogen, can contain up to two further different or identical heteroatoms O, N, S, $R_A^7$ is hydrogen, —OH, —CN, —CONH$_2$, a branched or unbranched, optionally substituted $C_1$-$C_4$-alkyl, $C_1$-$C_4$-alkoxy, $C_3$-$C_7$-cycloalkyl or —O—CO—$C_1$-$C_4$-alkyl radical, or an optionally substituted arylalkyl, —O-alkylenearyl, —O—CO-aryl, —O—CO-alkylenearyl or —O—CO-allyl radical, or both radicals $R_A^6$ and $R_A^7$ together are an optionally substituted, unsaturated or aromatic heterocycle which, in addition to the ring nitrogen, can contain up to two further different or identical heteroatoms O, N, S, $R_A^8$ is hydrogen, a branched or unbranched, optionally substituted $C_1$-$C_4$-alkyl, CO—$C_1$-$C_4$-alkyl, $SO_2$—$C_1$-$C_4$-alkyl or CO—O—$C_1$-$C_4$-alkyl radical or an optionally substituted aryl, CO-aryl, $SO_2$-aryl, CO—O-aryl, CO-alkylenearyl, $SO_2$-alkylenearyl, CO—O-alkylenearyl or alkylenearyl radical, $R_A^9$, $R_A^{10}$
independently of one another are hydrogen, —CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO-O-$R_A^{14}$, O-$R_A^{14}$, S-$R_A^{14}$, $NR_A^{15}R_A^{16}$, $SO_2$—$NR_A^{15}R_A^{16}$ or CO—$NR_A^{15}R_A^{16}$, or both radicals $R_A^9$ and $R_A^{10}$ together in structural element $I_A^{14}$ are a 5- to 7-membered saturated, unsaturated or aromatic carbocycle or heterocycle which can contain up to three different or identical heteroatoms O, N, S and is optionally substituted by up to three identical or different radicals, $R_A^{11}$ is hydrogen, —CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO-o-$R_A^{14}$, O-$R_A^{14}$, S-$R_A^{14}$, $NR_A^{15}R_A^{16}$, $SO_2$—$NR_A^{15}R_A^{16}$ or CO—$NR_A^{15}R_A^{16}$, $R_A^{17}$ is hydrogen or, in structural element $I_A^{16}$, both radicals $R_A^9$ and $R_A^{17}$ together are a 5- to 7-membered saturated, unsaturated or aromatic heterocycle which, in addition to the ring nitrogen, can contain up to three different or identical heteroatoms O, N, S and is optionally substituted by up to three identical or different radicals, $R_A^{18}$, $R_A^{19}$
independently of one another are hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bisalkylaminoalkylene or acylaminoalkylene radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G^{11}$, —CO—$ORG^{11}$, —CO—$NR_G^{11}R_G^{11*}$ or —CO-$R_G^{11}$ which is independent of $R_G^{11}$ $Z^1$, $Z^2$, $Z^3$, $Z^4$,
independently of one another are nitrogen, C—H, C-halogen or a branched or unbranched, optionally substituted C—$C_1$-$C_4$-alkyl or C—$C_1$-$C_4$-alkoxy radical, $Z^5$ is $NR_A^8$, oxygen or sulfur.

In a further very particularly preferred embodiment, the structural element A is a structural element of the formula $I^{41}$ $I_A^4$, $I_A^7$, $I_A^8$ or $I_A^9$.

A branched or unbranched, optionally substituted $C_1$-$C_6$-alkyl radical for $R_A^1$ or $R_A^2$ independently of one another is understood as meaning, for example, the corresponding radicals described above for $R_G^1$, preferably methyl or trifluoromethyl.

For $R_A^1$ or $R_A^2$ in the structural elements $I_A^1$, $I_A^2$, $I_A^3$ and $I_A^{17}$ the branched or unbranched, optionally substituted radical CO—$C_1$-$C_6$-alkyl is composed, for example, of the group CO and the branched or unbranched, optionally substituted $C_1$-$C_6$-alkyl radicals described above for $R_A^1$ or $R_A^2$.

Optionally substituted hetaryl, hetarylalkyl, aryl, arylalkyl or $C_3$-$C_7$-cycloalkyl radicals for $R_A^1$ or $R_A^2$ independently of one another are understood as meaning, for example, the corresponding radicals described above for $R_G^7$.

For $R_A^1$ or $R_A^2$, the optionally substituted radicals CO—O—$R_A^{14}$, O—$R_A^{14}$, S—$R_A^{14}$, $NR_A^{15}R_A^{16}$, CO—$NR^{415}R_A^{16}$ or $SO_2NR_A^{15}R_A^{16}$ are composed, for example, of the groups CO—O, O, S, N, CO—N or $SO_2$—N and the radicals $R_A^{14}$, $R_A^{15}$ or $R_A^{16}$ described in greater detail below.

Further, both radicals $R_A^1$ and $R_A^2$ can together form a fused, optionally substituted, 5- or 6-membered, unsaturated or aromatic carbocycle or heterocycle which can contain up to three heteroatoms selected from the group consisting of O, N and S.

$R_A^{13}$ and $R_A^{13*}$ are independently of one another hydrogen, CN,
halogen, such as fluorine, chlorine, bromine or iodine,
a branched or unbranched, optionally substituted $C_1$-$C_6$-alkyl radical, such as described above for $R_G^1$, preferably methyl or trifluoromethyl or
an optionally substituted aryl, arylalkyl, hetaryl or $C_3$-$C_7$-cycloalkyl radical or a radical CO—O—$R_A^{14}$, O—$R_A^{14}$, S-$R_A^{14}$, $NR_A^{15}R_A^{16}$, $SO_2NR_A^{15}R_A^{16}$ or CO—$NR_A^{15}R_A^{16}$ as in each case described above for $R_A^1$.

Preferred radicals for $R_A^{13}$ and $R_A^{13*}$ are the radicals hydrogen, F, Cl, a branched or unbranched, optionally substituted $C_1$-$C_6$-alkyl radical, optionally substituted aryl or arylalkyl or a radical CO—O—$R_A^{14}$, O—$R_A^{14}$, $NR_A^{15}R_A^{16}$, $SO_2$—$NR_A^{15}R_A^{16}$ or CO—$NR_A^{15}R_A^{16}$.

A branched or unbranched, optionally substituted $C_1$-$C_6$-alkyl, $C_3$-$C_7$-cycloalkyl, alkylenecycloalkyl, alkylene-$C_1$-$C_4$-alkoxy, $C_2$-$C_6$-alkenyl or $C_2$-$C_6$-alkynyl radical for $R_A^{14}$ in structural element A is understood as meaning, for example, the corresponding radicals described above for $R_G^7$.

Optionally substituted aryl, arylalkyl, hetaryl or alkylhetaryl radicals for $R_A^{14}$ in structural element A are understood as meaning, for example, the corresponding radicals described above for $R_G^7$.

Preferred radicals for $R_A^{14}$ are hydrogen, a branched or unbranched, optionally substituted $C_1$-$C_6$-alkyl radical and optionally substituted benzyl.

A branched or unbranched, optionally substituted $C_1$-$C_6$-alkyl or arylalkyl radical or an optionally substituted $C_3$-$C_7$-cycloalkyl, aryl, hetaryl or hetarylalkyl radical for $R_A^{15}$ or $R^{416}$ independently of one another is understood as meaning, for example, the corresponding radicals described above for $R_A^{14}$.

The branched or unbranched, optionally substituted CO—$C_1$-$C_6$-alkyl, $SO_2$—$C_1$-$C_6$-alkyl, COO-$C_1$-$C_6$-alkyl, CO—NH—$C_1$-$C_6$-alkyl, COO-alkylenearyl, CO—NH-alkylenearyl, CO—NH-alkylenehetaryl or $SO_2$-alkylenearyl radicals or the optionally substituted CO-aryl, $SO_2$-aryl, CO—NH-aryl, CO—NH-hetaryl or CO-hetaryl radicals for $R_A^{15}$ or $R_A^{16}$ are composed, for example, of the corresponding groups —CO—, —$SO_2$—, —CO—O—, —CO—NH— and the corresponding branched or unbranched, optionally substituted $C_1$-$C_6$-alkyl, hetarylalkyl or arylalkyl radicals or the corresponding optionally substituted aryl or hetaryl radicals described above.

A radical —$(CH_2)_n$—$(X_A)_j$—$R_A^{12}$ for $R_A^3$ or $R_A^4$ independently of one another is understood as meaning a radical which is composed of the corresponding radicals —$(CH_2)_n$—, $(XA)_j$ and $R_A^{12}$. Here, n can be: 0, 1, 2 or 3 and j can be: 0 or 1.

$X_A$ is a doubly bonded radical selected from the group consisting of —CO—, —CO—N($R_X^1$)—, —N($R_X^1$)—CO—, —N(($R_X^1$))—CO—N(($R_X^1$)*)—, —N($R_X^1$)—CO—O—, —O—, —S—, —$SO_2$—, —$SO_2$—N($R_X^1$)—, —$SO_2$—O—, —CO—O—, —O—CO—, —O—CO—N(($R_X^1$))—, —N($R_X^1$)— or —N(($R_X^1$))—$SO_2$—.

$R_A^{12}$ is hydrogen, a branched or unbranched, optionally substituted $C_1$-$C_6$-alkyl radical, as described above for $R_G^7$, a $C_2$-$C_6$-alkynyl or $C_2$-$C_6$-alkenyl radical optionally substituted by $C_1$-$C_4$-alkyl or aryl, or a 3- to 6-membered, saturated or unsaturated heterocycle which is substituted by up to three identical or different radicals and can contain up to three different or identical heteroatoms O, N, S, such as optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4-thiadiazolyl), 2-(1,3,4)-oxadiazolyl, 3-isoxazolyl, 4-isoxazolyl, 5-isoxazolyl, triazinyl.

Further, $R_A^{12}$ and $R_X^1$ or $R_X^{1*}$ can together form a saturated or unsaturated $C_3$-$C_7$-heterocycle which can optionally contain up to two further heteroatoms selected from the group consisting of O, S and N.

Preferably, the radical $R_A^{12}$ together with the radical $R_X^1$ or $R_X^{1*}$ forms a cyclic amine as the $C_3$-$C_7$-heterocycle in the case where the radicals are bonded to the same nitrogen atom, such as N-pyrrolidinyl, N-piperidinyl, N-hexahydroazepinyl, N-morpholinyl or N-piperazinyl, where in heterocycles which carry free amine protons, such as N-piperazinyl, the free amine protons can be replaced by customary amine protective groups, such as methyl, benzyl, Boc (tert-butoxycarbonyl), Z (benzyloxycarbonyl), tosyl, —$SO_2$—$C_1$-$C_4$-alkyl, —$SO_2$-phenyl or —$SO_2$-benzyl.

A branched or unbranched, optionally substituted $C_1$-$C_6$-alkyl, $C_2$-$C_{12}$-alkynyl, preferably $C_2$-$C_6$-alkynyl or $C_2$-$C_6$-alkenyl radical, an optionally substituted $C_3$-$C_7$-cycloalkyl, aryl, arylalkyl or hetaryl radical for $R_X^1$ and $R_X^{1*}$ independently of one another is understood as meaning, for example, the corresponding radicals described above for $R_G^7$.

Preferred branched or unbranched, optionally substituted $C_1$-$C_6$-alkoxyalkyl for $R_X^1$ and $R_X^{1*}$ are independently of one another methoxymethylene, ethoxymethylene, t-butoxymethylene, methoxyethylene or ethoxyethylene.

Preferred branched or unbranched, optionally substituted radicals CO—$C_1$-$C_6$-alkyl, CO—O—$C_1$-$C_6$-alkyl, $SO_2$—$C_1$-$C_6$-alkyl, CO—O-alkylenearyl, CO-alkylenearyl, CO-aryl, $SO_2$-aryl, CO-hetaryl or $SO_2$-alkylenearyl are preferably composed of the $C_1$-$C_6$-alkyl, arylalkyl, aryl or hetaryl radicals and the radicals —CO—, —O—, —$SO_2$— described above.

Preferred radicals for $R_X^1$ and $R_X^{1*}$ are independently of one another hydrogen, methyl, cyclopropyl, allyl and propargyl.

$R_A^3$ and $R_A^4$ can further together form a 3- to 8-membered saturated, unsaturated or aromatic N heterocycle which can additionally contain two further, identical or different heteroatoms O, N or S, where the cycle can be optionally substituted or a further, optionally substituted, saturated, unsaturated or aromatic cycle can be fused to this cycle, $R_A^5$ is a branched or unbranched, optionally substituted $C_1$-$C_6$-alkyl, arylalkyl, $C_1$-$C_4$-alkyl-$C_3$-$C_7$-cycloalkyl or $C_3$-$C_7$-cycloalkyl radical or an optionally substituted aryl, hetaryl, heterocycloalkyl or heterocycloalkenyl radical, such as described above for $R_G^7$.

$R_A^6$ and $R_A^{6*}$ are independently of one another hydrogen, a branched or unbranched, optionally substituted $C_1$-$C_4$-alkyl radical, such as optionally substituted methyl, ethyl, propyl, 1-methylethyl, butyl, 1-methylpropyl, 2-methylpropyl or 1,1-dimethylethyl, —CO—O—$C_1$-$C_4$-alkyl or —CO—$C_1$-$C_4$-alkyl radical such as composed of the group —CO—O— or —CO— and the $C_1$-$C_4$-alkyl radicals described above, arylalkyl radical, as described above for $R_G^7$, —CO—O-alkylenearyl or —CO-alkylenearyl radical such as composed of the group —CO—O— or —CO— and the arylalkyl radicals described above, —CO—O-allyl or —CO-allyl radical, or $C_3$-$C_7$-cycloalkyl radical, such as described above for $R_G^7$.

Further, both radicals $R_A^6$ and $R_A^{6*}$ in structural element $I_A^7$ can together form an optionally substituted, saturated, unsaturated or aromatic heterocycle which, in addition to the ring nitrogen, can contain up to two further different or identical heteroatoms O, N, S.

$R_A^7$ is hydrogen, —OH, —CN, —$CONH_2$, a branched or unbranched, optionally substituted $C_1$-$C_4$-alkyl radical, for example as described above for $R_A^6$, $C_1$-$C_4$-alkoxy, arylalkyl or $C_3$-$C_7$-cycloalkyl radical, for example as described above for $R_L^{14}$, a branched or unbranched, optionally substituted —O—CO—$C_1$-$C_4$-alkyl radical, which is composed of the group —O—CO— and, for example, of the $C_1$-$C_4$-alkyl radicals mentioned above or an optionally substituted —O-alkylenearyl, —O—CO-aryl, —O—CO-alkylenearyl or —O—CO-allyl radical which is composed of the groups —O— or —O—CO— and, for example, of the corresponding radicals described above for $R_G^7$.

Further, both radicals $R_A^6$ and $R_A^7$ can together form an optionally substituted unsaturated or aromatic heterocycle which, in addition to the ring nitrogen, can contain up to two further different or identical heteroatoms O, N, S.

For $R_A^8$ in structural element A, a branched or unbranched, optionally substituted $C_1$-$C_4$-alkyl radical or an optionally substituted aryl or arylalkyl radical is understood as meaning, for example, the corresponding radicals described above for $R_A^{15}$, where the radicals CO—$C_1$-$C_4$-alkyl, $SO_2$—$C_1$-$C_4$-alkyl, CO—O—$C_1$-$C_4$-alkyl, CO-aryl, $SO_2$-aryl, CO—O-aryl, CO-alkylenearyl, $SO_2$-alkylenearyl or CO—O-alkylenearyl are composed analogously to the other composed radicals of the group consisting of CO, $SO_2$ and COO and, for example, of the corresponding $C_1$-$C_4$-alkyl, aryl or arylalkyl radicals described above for $R_A^{15}$, and these radicals can be optionally substituted.

In each case, for $R_A^9$ or $R_A^{10}$, a branched or unbranched, optionally substituted $C_1$-$C_6$-alkyl radical or an optionally substituted aryl, arylalkyl, hetaryl or $C_3$-$C_7$-cycloalkyl radical independently of one another is understood as meaning, for example, the corresponding radicals described above for $R_A^{14}$, preferably methyl or trifluoromethyl.

In each case, for $R_A^9$ or $R_A^{10}$, a radical CO—O—$R_A^{14}$, O—$R_A^{14}$, S-$R_A^{14}$, $SO_2$—$NR_A^{15}R_A^{16}$, $NR_A^{15}R_A^{16}$ or CO—$NR_A^{15}R_A^{16}$ independently of one another is understood as meaning, for example, the corresponding radicals described above for $R_A^{13}$.

Further, both radicals $R_A^9$ and $R_A^{10}$ together in structural element $I_A^{14}$ can form a 5- to 7-membered saturated, unsaturated or aromatic carbocycle or heterocycle, which can contain up to three different or identical heteroatoms O, N, S and is optionally substituted by up to three identical or different radicals.

Substituents in this case are in particular understood as meaning halogen, CN, a branched or unbranched, optionally substituted $C_1$-$C_4$-alkyl radical, such as methyl or trifluoromethyl or the radicals O—$R_A^{14}$, S-$R_A^{14}$, $NR_A^{15}R_A^{16}$, CO—$NR_A^{15}R_A^{16}$ or —(($R_A^8$)HN)C=$NR_A^7$.

A branched or unbranched, optionally substituted $C_1$-$C_6$-alkyl radical or an optionally substituted aryl, arylalkyl, hetaryl, $C_3$-$C_7$-cycloalkyl radical or a radical CO—O—$R_A^{14}$, O—$R_A^{14}$, S—$R_A^{14}$, $NR_A^{15}R_A^{16}$, $SO_2$—$NR_A^{15}R_A^{16}$ or CO—$NR_A^{15}R_A^{16}$ for $R_A^{11}$ is understood, for example, as meaning the corresponding radicals described above for $R_A^9$.

Further, in structural element $I_A^{16}$, both radicals $R_A^9$ and $R_A^{17}$ together can form a 5- to 7-membered saturated, unsaturated or aromatic heterocycle which, in addition to the ring nitrogen, can contain up to three different or identical heteroatoms O, N, S and is optionally substituted by up to three id ntical or different radicals.

A branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bisalkylaminoalkylene or acylaminoalkylene radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G^{11}$, —CO—$OR_G^{11}$, —CO—$NR_G^{11}R_G^{11*}$ or —CO-$R_G^1$ for $R_A^{18}$ and $R_A^{19}$ independently of one another is understood as meaning, for example, the radicals described above for $R_G^{12}$, preferably hydrogen or a branched or unbranched, optionally substituted $C_1$-$C_8$-alkyl radical.

$Z^1$, $Z^2$, $Z^3$, $Z^4$ are independently of one another nitrogen, C—H, C-halogen, such as C—F, C—Cl, C—Br or C—I or a branched or unbranched, optionally substituted C—$C_1$-$C_4$-alkyl radical which is composed of a carbon radical and, for example, a $C_1$-$C_4$-alkyl radical described above for $R_A^6$ or a branched or unbranched optionally substituted C—$C_1$-$C_4$-alkoxy radical which is composed of a carbon radical and, for example, a $C_1$-$C_4$-alkoxy radical described above for $R_A^7$.

$Z^5$ is oxygen, sulfur or a radical $NR_A^8$.

Preferred structural elements A are composed of at least one preferred radical of the radicals belonging to the structural element A, while the remaining radicals are widely variable.

Particularly preferred structural elements A are composed of the preferred radicals of the structural element A.

In a preferred embodiment, the spacer structural element E is understood as meaning a structural element that consists of a branched or unbranched aliphatic $C_2$-$C_{30}$-hydrocarbon radical which is optionally substituted and contains heteroatoms and/or of a 4-to 20-membered aliphatic or aromatic mono- or polycyclic hydrocarbon radical which is optionally substituted and contains heteroatoms.

In a further preferred embodiment, the spacer structural element E is composed of two to four substructural elements, selected from the group consisting of $E^1$ and $E^2$, where the sequence of linkage of the substructural elements is arbitrary and $E^1$ and $E^2$ have the following meanings:

$E^1$ is a substructural element of the formula $I_{E1}$

and $E^2$ is a substructural element of the formula $I_{E2}$

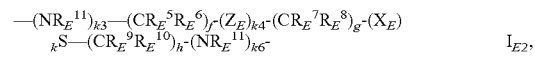

where c, d, f, g, h
   independently of one another are 0, 1 or 2, k1, k2, k3, k4, k5, k6
   independently of one another are 0 or 1, XE, QE
   independently of one another are an optionally substituted 4- to 11-membered mono- or polycyclic, aliphatic or aromatic hydrocarbon which can contain up to 6 double bonds and up to 6 identical or different heteroatoms selected from the group N, O and S, where the ring carbons and/or the ring nitrogens can optionally be substituted, YE, ZE
   independently of one another are CO, CO—$NR_E^{12}$, $NR_E^{12}$-CO, sulfur, SO, $SO_2$, $SO_2$—$NR_E^{12}$, $NR_E^{12}$—$SO_2$, CS, CS—$NR_E^{12}$, $NR_E^{12}$—CS, CS—O, O—CS, CO—O, O—CO, oxygen, ethynylene, $CR_E^{13}$-O—$CR_E^{14}$, C(=$CR_E^{13}R_E^{14}$), $CR_E^{13}$=$CR_E^{14}$, —$CR_E^{13}$($CR_E^{15}$)—$CHR_E^{14}$- or —$CHR_E^{13}$-$CR_E^{14}$($OR_E^{15}$)-, $R_E^1$, $R_E^2$, $R_E^3$, $R_E^4$, $R_E^5$, $R_E^6$, $R_E^7$, $R_E^8$, $R_E^9$, $R_E^{10}$
   independently of one another are hydrogen, halogen, a hydroxyl group, a branched or unbranched, optionally substituted $C_1$-$C_6$-alkyl, $C_2$-$C_6$-alkenyl, $C_2$-$C_6$-alkynyl or alkylenecycloalkyl radical, a radical —$(CH_2)_x$—$(W_E)_z$-$R_E^{17}$, an optionally substituted $C_3$-$C_7$-cycloalkyl, aryl, arylalkyl, hetaryl or hetarylalkyl radical or independently of one another in each case two radicals $R_E^1$ and $R_E^2$ or $R_E^3$ and $R_E^4$ or $R_E^5$ and $R_E^6$ or $R_E^7$ and $R_E^8$ or $R_E^9$ and $R_E^{10}$ together are a 3- to 7-membered, optionally substituted, saturated or unsaturated carbocycle or heterocycle which can contain up to three heteroatoms selected from the group O, N and S, x is 0, 1, 2, 3 or 4, z is 0 or 1, $W_E$ is —CO—, —CO—N($R_W^2$)—, —N($R_W^2$)—CO—, —N($R_W^2$)—CO—N($R_W^{2*}$)—, —N($R_W^2$)—CO—O—, —O—, —S—, —SO$_2$—, —SO$_2$—N($R_W^2$)—, —SO$_2$—O—, —CO—O—, —O—CO—, —O—CO—N($R_W^2$)—, —N($R_W^2$)— or —N($R_W^2$)—SO$_2$—, $R_W^2$, $R_W^{2*}$ independently of one another are hydrogen, a branched or unbranched, optionally substituted $C_1$-$C_6$-alkyl, $C_2$-$C_6$-alkenyl, $C_2$-$C_8$-alkynyl, CO—$C_1$-$C_6$-alkyl, CO—O—$C_1$-$C_6$-alkyl or SO$_2$—$C_1$-$C_6$-alkyl radical or an optionally substituted hetaryl, hetarylalkyl, arylalkyl, $C_3$-$C_7$-cycloalkyl, CO—O-alkylenearyl, CO-alkylenearyl, CO-aryl, SO$_2$-aryl, CO-hetaryl or SO$_2$-alkylenearyl radical, $R_E^{17}$ is hydrogen, a hydroxyl group, CN, halogen, a branched or unbranched, optionally substituted $C_1$-$C_6$-alkyl radical, an optionally substituted $C_3$-$C_7$-cycloalkyl, aryl, hetaryl or arylalkyl radical, a $C_2$-$C_6$-alkynyl or $C_2$-$C_6$-alkenyl radical optionally substituted by $C_1$-$C_4$alkyl or aryl, an optionally substituted $C_6$-$C_{12}$-bicycloalkyl, $C_1$-$C_6$-alkylene-$C_6$-$C_{12}$-bicycloalkyl, $C_7$-$C_{20}$-tricycloalkyl or $C_1$-$C_6$-alkylene-$C_7$-$C_{20}$-tricycloalkyl radical, or a 3- to 8-membered, saturated or unsaturated heterocycle substituted by up to three identical or different radicals, which can contain up to three different or identical heteroatoms O, N, S, where two radicals together can be a fused, saturated, unsaturated or aromatic carbocycle or heterocycle which can contain up to three different or identical heteroatoms O, N, S and the cycle can optionally be substituted or a further, optionally substituted, saturated, unsaturated or aromatic cycle can be fused to this cycle, or the radical $R_E^{17}$ forms, together with $R_W^2$ or $R_W^{2*}$ a saturated or unsaturated $C_3$-$C_7$-heterocycle which can optionally contain up to two further heteroatoms selected from the group O, S and N, $R_E^{11}$, $R_E^{11*}$ independently of one another are hydrogen, a branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl, CO—$C_1$-$C_6$-alkyl, CO—O—$C_1$-$C_6$-alkyl, CO—NH—$C_1$-$C_6$-alkoxyalkyl, CO—NH—$C_1$-$C_6$-alkyl or SO$_2$—$C_1$-$C_6$-alkyl radical or an optionally substituted hetaryl, arylalkyl, $C_3$-$C_7$-cycloalkyl, CO—O-alkylenearyl, CO—NH-alkylenearyl, CO-alkylenearyl, CO-aryl, CO—NH-aryl, SO$_2$-aryl, CO-hetaryl, SO$_2$-alkylenearyl, SO$_2$-hetaryl or SO$_2$-alkylenehetaryl radical, $R_E^{12}$ is hydrogen, a branched or unbranched, optionally substituted $C_1$-$C_6$-alkyl, $C_2$-$C_6$-alkenyl, $C_2$-$C_8$-alkynyl radical, an optionally substituted $C_3$-$C_7$-cycloalkyl, hetaryl, arylalkyl or hetarylalkyl radical or a radical CO—$R_E^{16}$, COOR$_E^{16}$ or SO$_2$—$R_E^{16}$, $R_E^{13}$, $R_E^{14}$ independently of one another are hydrogen, a hydroxyl group, a branched or unbranched, optionally substituted $C_1$-$C_6$-alkyl, $C_1$-$C_4$-alkoxy, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, $R_E^{15}$ is hydrogen, a branched or unbranched, optionally substituted $C_1$-$C_6$-alkyl, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, $R_E^{16}$ is hydrogen, a hydroxyl group, a branched or unbranched, optionally substituted $C_1$-$C_6$-alkyl, $C_2$-$C_6$-alkenyl, $C_2$-$C_6$-alkynyl or $C_1$-$C_5$-alkylene-$C_1$-$C_4$-alkoxy radical, or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkylene-$C_3$-$C_7$-heterocycloalkyl, $C_1$-$C_4$-alkylene-$C_3$-$C_7$-heterocycloalkenyl or hetarylalkyl radical.

The coefficient c is preferably 0 or 1, the coefficient d is preferably 1 or 2, the coefficients f, g, h independently of one another are preferably 0 or 1 and $K^6$ is preferably 0.

An optionally substituted 4- to 11-membered mono- or polycyclic aliphatic or aromatic hydrocarbon which can contain up to 6 double bonds and up to 6 identical or different heteroatoms selected from the group consisting of N, O, S, where the ring carbons or ring nitrogens can optionally be substituted, for $Q_E$ and $X_E$ independently of one another is preferably understood as meaning optionally substituted arylene, such as optionally substituted phenylene or naphthylene, or optionally substituted hetarylene such as the radicals

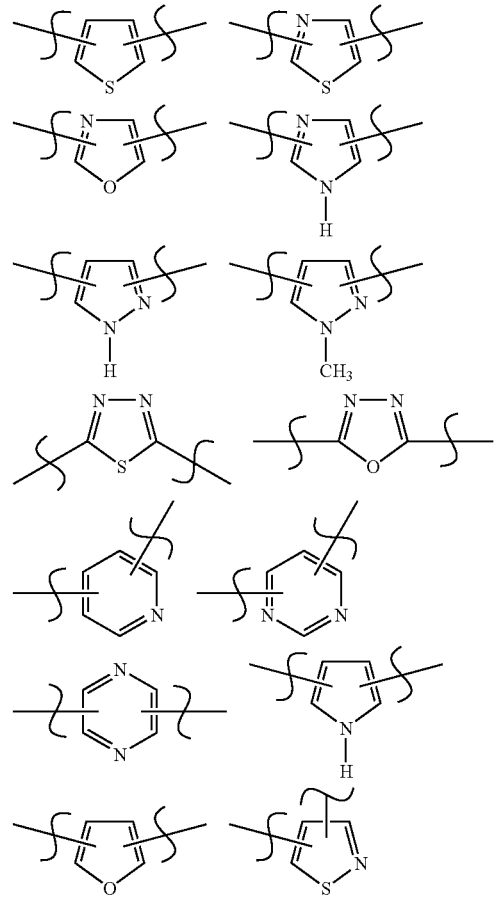

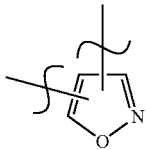

and their substituted or fused derivatives, or radicals of the formulae $I_E^1$ to $I_E^{11}$, $I_E^1$
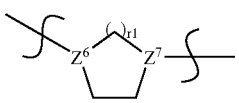

$I_E^2$
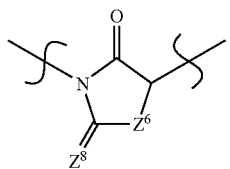

$I_E^3$
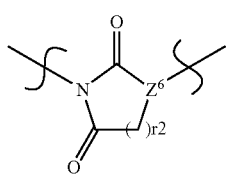

$I_E^4$
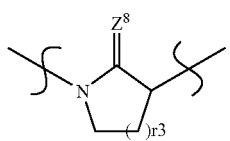

$I_E^5$
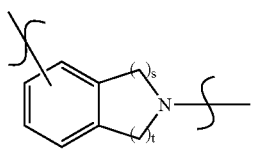

$I_E^6$
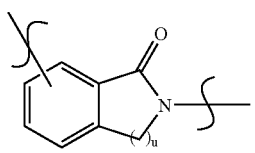

$I_E^7$
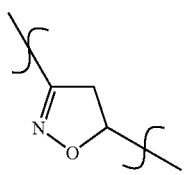

$I_E^8$
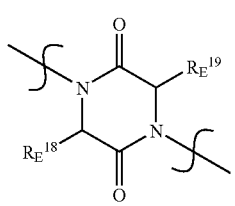

$I_E^9$
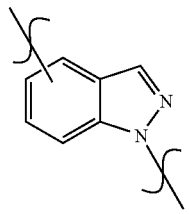

$I_E^{10}$
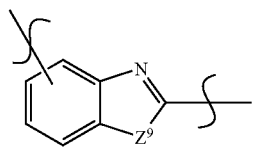

$I_E^{11}$
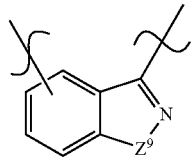

where the incorporation of the radicals can take place in both orientations. Aliphatic hydrocarbons are understood as meaning, for example, saturated and unsaturated hydrocarbons.

$Z^6$ and $Z^7$ are independently of one another CH or nitrogen.
$Z^8$ is oxygen, sulfur or NH,
$Z^9$ is oxygen, sulfur or $NR_E^{20}$.
r1, r2, r3 and t are independently of one another 0, 1, 2 or 3.
s and u are independently of one another 0, 1 or 2.
Particularly preferably, XE and QE independently of one another are optionally substituted phenylene, a radical

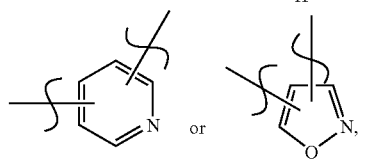

and their substituted or fused derivatives, or radicals of the formulae $I_E^1$, $I_E^2$, $I_E^3$, $I_E^4$ and $I_E^7$, where the incorporation of the radicals can take place in both orientations.

$R_E^{18}$ and $R_E^{19}$ are independently of one another hydrogen, —$NO_2$, —$NH_2$, —CN, —COOH, a hydroxyl group, halogen, a branched or unbranched, optionally substituted $C_1$-$C_6$-alkyl, $C_1$-$C_4$-alkoxy, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, as in each case described above.

$R^{E20}$ is, independently of one another, hydrogen, a branched or unbranched, optionally substituted $C_1$-$C_6$-alkyl, $C_1$-$C_6$-alkoxyalkyl, $C_3$-$C_{12}$-alkynyl, CO—$C_1$-$C_6$-alkyl, C0-O—$C_1$-$C_6$-alkyl or $SO_2$—$C_1$-$C_6$-alkyl radical or an optionally substituted $C_3$-$C_7$-cycloalkyl, aryl, arylalkyl, CO—O-alkylenearyl, CO-alkylenearyl, CO-aryl, $SO_2$-aryl, hetaryl, CO-hetaryl or $SO_2$-alkylenearyl radical, preferably hydrogen or a branched or unbranched, optionally substituted $C_1$-$C_6$-alkyl radical.

$Y_E$ and $Z_E$ are independently of one another CO, CO—$NR_E^{12}$, $NR_E^{12}$-CO, sulfur, SO, $SO_2$, $SO_2$—$NR_E^{12}$, $NR_E^{12}$-$SO_2$, CS, CS—$NR_E^{12}$, $NR_E^{12}$-CS, CS—O, O—CS, CO—O,O—CO, oxygen, ethynylene, $CR_E^{13}$-O—$CR_E^{14}$, $C(=CR_E^{13}R_E^{14})$, $CR_E^{13}=CR_E^{14}$, —$CR_E^{13}(OR_E^{15})$—$CHR_E^{14}$— or —$CHR_E^{13}$-$CR_E^{14}(OR_E^{15})$-, preferably CO, $SO_2$ and oxygen.

$R_E^{12}$ is hydrogen, a branched or unbranched, optionally substituted $C_1$-$C_6$-alkyl, $C_2$-$C_6$-alkenyl or $C_2$-$C_8$-alkynyl radical or an optionally substituted $C_3$-$C_7$-cycloalkyl, hetaryl, arylalkyl or hetarylalkyl radical, such as correspondingly described above for $R_G^7$ or a radical CO—$R_E^{16}$, $COOR^{E16}$ or $SO_2$—$R_E^{16}$, preferably hydrogen, methyl, allyl, propargyl and cyclopropyl.

A branched or unbranched, optionally substituted $C_1$-$C_6$-alkyl, $C_2$-$C_6$-alkenyl or $C_2$-$C_6$-alkynyl radical or an optionally substituted $C_3$-$C_7$-cycloalkyl, aryl, arylalkyl, hetaryl or hetarylalkyl radical for $R_E^{13}$, $R_E^{14}$ or $R_E^{15}$ independently of one another is understood as meaning, for example, the corresponding radicals described above for $R_G^7$.

A branched or unbranched, optionally substituted $C_1$-$C_4$-alkoxy radical for $R_E^{13}$ or $R_E^{14}$ independently of one another is understood as meaning, for example, the $C_1$-$C_4$-alkoxy radicals described above for $R_A^{14}$.

Preferred alkylenecycloalkyl radicals for $R_E^{13}$, $R_E^{14}$ or $R^{E15}$ independently of one another are, for example, the $C_1$-$C_4$-alkylene-$C_3$-$C_7$-cycloalkyl radicals described above for $R_G^7$.

A branched or unbranched, optionally substituted $C_1$-$C_6$-alkyl, $C_2$-$C_6$-alkenyl, $C_2$-$C_6$-alkynyl or $C_1$-$C_5$-alkylene-$C_1$-$C_4$-alkoxy radical, or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkylene-$C_3$-$C_7$-heterocycloalkyl, $C_1$-$C_4$-alkylene-$C_3$-$C_7$-heterocycloalkenyl or hetarylalkyl radical for $R_E^{16}$ is understood as meaning, for example, the corresponding radicals described above for $R_G^{11}$.

A branched or unbranched, optionally substituted $C_1$-$C_6$-alkyl, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical for $R_E^1$, $R_E^2$, $R_E^3$, $R_E^4$, $R_E^5$, $R_E^6$, $R_E^7$, $R_E^8$, $R_E^9$ or $R_E^{10}$ independently of one another is understood as meaning, for example, the corresponding radicals mentioned above for $R_G^7$.

Further, two radicals $R_E^3$ and $R_E^4$ or $R_E^5$ and $R_E^6$ or $R_E^7$ and $R_E^8$ or $R_E^9$ and $R_E^{10}$ can in each case independently of one another together form a 3- to 7-membered, optionally substituted, saturated or unsaturated carbo- or heterocycle which can contain up to three heteroatoms from the group consisting of O, N and S.

The radical —$(CH2)_x$—$(W_E)_z$-$R_E^{17}$ is composed of a CO—$C_4$-alkylene radical, optionally a bonding element WE selected from the group —CO—, —CO—N($R^2$)—, —N($R^{12}$)—CO—, —N($R_W^2$)—CO—N($R_W^{2*}$)—, —N($R^2$)—O—O—, —O—, —S—, —$SO_2$—, —$SO_2$—N($R_W^2$)—, —$SO_2$—O—, —CO—O—, —O—CO—O—, CO—N($R_W^2$)—, —N($R_W^2$)— or —N($R_W^2$)—$SO_2$—, preferably selected from the group —CO—N($R_W^2$)—, —N($R_W^2$)—CO—, —O—, —$SO_2$—N($R_W^2$)—, —N($R_W^2$)— or —N($R_W^2$)—$SO_2$—, and the radical $R_E^{17}$, where $R_W^2$ and $R_W^{2*}$ independently of one another are hydrogen, a branched or unbranched, optionally substituted $C_1$-$C_6$-alkyl, $C_2$-$C_6$-alkenyl, $C_2$-$C_8$-alkynyl, CO—$C_1$-$C_6$-alkyl, CO—O—$C_1$-$C_6$-alkyl or $SO_2$—$C_1$-$C_6$-alkyl radical or an optionally substituted hetaryl, hetarylalkyl, arylalkyl, $C_3$-$C_7$-cycloalkyl, CO—O-alkylenearyl, CO-alkylenearyl, CO-aryl, $SO_2$-aryl, CO-hetaryl or $SO_2$-alkylenearyl radical, preferably independently of one another are hydrogen, methyl, cyclopropyl, allyl, propargyl, and $R_E^{17}$ is hydrogen, a hydroxyl group, CN, halogen, a branched or unbranched, optionally substituted $C_1$-$C_6$-alkyl radical, an optionally substituted $C_3$-$C_7$-cycloalkyl, aryl, hetaryl or arylalkyl radical, a $C_2C_6$alkynyl or $C_2$-$C_6$-alkenyl radical optionally substituted by $C_1$-$C_4$alkyl or aryl, an optionally substituted $C_6$-$C_{12}$-bicycloalkyl, $C_1$-$C_6$-alkylene-$C_6$-$C_{12}$-bicycloalkyl, $C_7$-$C_{20}$-tricycloalkyl or $C_1$-$C_6$-alkylene-$C_7$-$C_{20}$-tricycloalkyl radical, or a 3- to 8-membered, saturated or unsaturated heterocycle which is substituted by up to three identical or different radicals and can contain up to three different or identical heteroatoms O, N, S, where two radicals together can be a fused, saturated, unsaturated or aromatic carbocycle or heterocycle which can contain up to three different or identical heteroatoms O, N, S, and the cycle can be optionally substituted or a further, optionally substituted, saturated, unsaturated or aromatic cycle can be fused to this cycle, such as optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4-thiadiazolyl), 2-(1,3,4)-oxadiazolyl, 3-isoxazolyl, 4-isoxazolyl, 5-isoxazolyl or triazinyl.

Further, $R_E^{17}$ and $R_W^2$ or $R_W^{2*}$ can together form a saturated or unsaturated $C_3$-$C_7$-heterocycle which can optionally contain up to two further heteroatoms selected from the group consisting of O, S and N.

Preferably, the radicals $R_E^{17}$ and $R_W^2$ or $R_W^{2*}$ together form a cyclic amine as the $C_3$-$C_7$-heterocycle in the case where the radicals are bonded to the same nitrogen atom, such as N-pyrrolidinyl, N-piperidinyl, N-hexahydroazepinyl, N-morpholinyl or N-piperazinyl where in heterocycles which carry free amine protons, such as N-piperazinyl, the free amine protons can be replaced by customary amine protective groups, such as methyl, benzyl, Boc (tert-butoxycarbonyl), Z (benzyloxycarbonyl), tosyl, —$SO_2$—$C_1$-$C_4$-alkyl, —$SO_2$-phenyl or —$SO_2$-benzyl.

Preferred radicals for $R_E^1$, $R_E^2$, $R_E^3$, $R_E^4$, $R_E^5$, $R_E^6$, $R_E^7$, $R_E^8$, $R_E^9$ or $R_E^{10}$ are independently of one another hydrogen, halogen, a branched or unbranched, optionally substituted $C_1$-$C_6$-alkyl radical, optionally substituted aryl or the radical —$(CH_2)_x$—$(W_E)_z$—$R_E^{17}$.

Particularly preferred radicals for $R_E^1$, $R_E^2$, $R_E^3$, $R_E^4$, $R_E^5$, $R_E^6$, $R_E^7$, $R_E^8$, $R_E^9$ or $R_E^{10}$ are independently of one another hydrogen, F, a branched or unbranched, optionally substituted $C_1$-$C_4$-alkyl radical, in particular methyl.

A branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl or arylalkyl radical or an optionally substituted aryl, hetaryl or $C_3$-$C_7$-cycloalkyl for $R_E^{11}$ and $R_E^{11*}$ in structural element E independently of one another is understood as meaning, for example, the corresponding radicals described above for $R_G^7$.

The branched or unbranched, optionally substituted radicals CO—$C_1$-$C_6$-alkyl, CO—O—$C_1$-$C_6$-alkyl, CO—NH—$C_1$-$C_6$-alkoxalkyl, CO—NH—$C_1$-$C_6$-alkyl or $SO_2$—$C_1$-$C_6$-alkyl radical or the optionally substituted radicals CO—O-alkylenearyl, CO—NH-alkylenearyl, CO-alkylenearyl, CO-aryl, CO—NH-aryl, $SO_2$-aryl, CO-hetaryl, $SO_2$-alkylenearyl, $SO_2$-hetaryl or $SO_2$-alkylenehetaryl for $R_E^{11}$ and $R^{E11*}$ independently of one another are composed, for example, of the corresponding groups CO, COO, CONH or $SO_2$ and the corresponding radicals mentioned above.

Preferred radicals for $R_E^{11}$ or $R_E^{11*}$ are independently of one another hydrogen, a branched or unbranched, optionally substituted $C_1$-$C_6$-alkyl, $C_1$-$C_6$-alkoxy, $C_2$-$C_6$-alkenyl, $C_2$-$C_{12}$-alkynyl or arylalkyl radical, or an optionally substituted hetaryl or $C_3$-$C_7$-cycloalkyl radical.

Particularly preferred radicals for $R_E^{11}$ or $R_E^{11*}$ are hydrogen, methyl, cyclopropyl, allyl or propargyl.

In a particularly preferred embodiment of structural element $E_1$, structural element $E_1$ is a radical —$CH_2$—$CH_2$—CO—, —$CH_2$—$CH_2$—$CH_2$—CO— or a $C_1$-$C_5$-alkylene radical.

In a particularly preferred embodiment of structural element E, the spacer structural element E used is a structural element of the formula $I_{E1E2}$ $$-E_2-E_1- \qquad I_{E1E2}$$

where the structural elements $E_2$ and $E_1$ have the meanings described above.

Preferred structural elements E are composed of at least one preferred radical of the radicals belonging to structural element E, while the remaining radicals are widely variable.

Particularly preferred structural elements E are composed of the preferred radicals of structural element E.

Preferred structural elements B are composed either of the preferred structural element A, while E is widely variable or of the preferred structural element E, while A is widely variable.

The compounds of the formula I, and also the intermediates for their preparation, can have one or more asymmetric substituted carbon atoms. The compounds can be present as pure enantiomers or pure diastereomers or as a mixture thereof. The use of an enantiomerically pure compound as the active compound is preferred.

The compounds of the formula I can also be present in other tautomeric forms.

The compounds of the formula I can also be present in the form of physiologically tolerable salts.

The compounds of the formula I can also be present as prodrugs in a form in which the compounds of the formula I are liberated under physiological conditions. By way of example, reference may be made here to the group T in structural element L, which in some cases contains groups which are hydrolyzable to the free carboxylic acid group under physiological conditions. Derivatized structural elements B or A are also suitable which liberate the structural element B or A respectively under physiological conditions.

In preferred compounds of the formula I, in each case one of the three structural elements B, G or L has the preferred range, while the remaining structural elements are widely variable.

In particularly preferred compounds of the formula I, in each case two of the three structural elements B, G or L have the preferred range, while the remaining structural elements are widely variable.

In very particularly preferred compounds of the formula I, in each case all three structural elements B, G or L have the preferred range, while the remaining structural element is widely variable.

Preferred compounds of the formula I contain, for example, the preferred structural element G, while the structural elements B and L are widely variable.

In particularly preferred compounds of the formula I, for example, B is replaced by the structural element A-E- and the compounds contain, for example, the preferred structural element G and the preferred structural element A, while the structural elements E and L are widely variable.

Further particularly preferred compounds of the formula I contain, for example, the preferred structural element G and the preferred structural element A, while the structural elements E and L are widely variable.

Very particularly preferred compounds of the formula I in which A-E- is B- are listed below, the number before the text block being the number of an individualized compound of the formula I, and in the text block A-E-G-L the abbreviations being separated by a bonding dash in each case for an individual structural element A, E, G or L and the meaning of the abbreviations of the structural elements being explained after the table.

No. A-E-G-L
1 bhs-dibema2-mmophec-es
2 gua-mepipe2-phec-es
3 gua-35thima2-4phaz-es
4 bhs-apma2-pclphec-es
5 gua-a23thima2-4bec-es
6 bim-dibema2-4bec-es
8 bim-bam2-mmphec-es
9 2py-a23thima2-thec-es
10 gua-pipa2-4pec-es
11 dhim-35thima2-thec-es
12 gua-a24thima2-amaz-es
13 bim-pyma2-phec-es
14 gua-a24thima2-3bzlaz-es
15 bhs-inda2-thec-es
16 2py-a24thima2-3bec-nes
17 gua-a24thima2-phaz-es
18 gua-bam2-pymaz-es
19 gua-me35thima2-phec-es
2py-dibema2-4pec-es
21 bhs-35thima2-thec-gs
22 bhs-aaf-3bec-es
23 im-35thima2-thec-es
24 bhs-a23thima2-3ipec-es
25 bim-pipa2-4pec-es
26 bhs-mea2-thec-es
27 gua-dibema2-7 cmc-es
28 2py-apma2-phaz-es
29 bhs-apma2-7 cmc-es
30 thpym-bam2-4pec-es
31 bim-me35thima2-4pec-es
32 bim-a24thima2-3bec-es
33 bhs-me42thiaz2-phaz-es
34 2py-42thiaz2-thec-es
35 2py-pipa2-cpec-es
36 bim-35thima2-pymaz-es
37 bhs-a23thima2-3bec-es
38 2py-apma2-ppec-es
39 bhs-35thima2-pclphec-es 40 2py-buta-3bec-es
41 bim-a23thima2-7 cmc-gs
42 bhs-hexa-thec-es
43 bim-a23thima2-4pec-f2es
44 2py-35thima2-7 cmc-es
45 gua-chex2-4pec-es
46 bhs-edia2-thec-es
47 bhs-bam2-phaz-es
48 amim-35thima2-3bec-es
49 clim-apma2-3bec-es
50 gua-pipa2-phec-mals
51 am2py-a24thima2-thec-es
52 bhs-apma2-phaz-gs
53 2py-inda2-thec-es
54 bim-35thima2-mmophec-es
55 2py-inda2-3bec-es
56 2py-mepipe2-thec-es
57 bim-bam2-thec-es
58 bim-bam2-4phaz-es
59 2py-apma2-3bec-es
60 bhs-a24thima2-pmophec-es
61 bim-dibema2-thec-es
62 mam2py-a24thima2-phaz-es
63 2py-mea2-3bec-es
64 bim-penta-4pec-es
65 gua-prodia2-7 cmc-es
66 bhs-dibema2-cpec-es
67 2py-hexa-phaz-es
68 gua-apma2-3ipec-es
69 bim-apma2-phec-ms
70 gua-35thima2-phec-ps
71 bim-pipa2-3bec-es
72 gua-a23thima2-phec-es
73 2py-42thiaz2-phaz-es
74 bim-me35thima2-7 cmc-es
75 bhs-bam2-mpphec-es
76 gua-dibema2-thec-es
77 clim-bam2-thec-es
78 dimethpym-a23thima2-thec-es
79 gua-dibema2-4pec-es
80 bhs-apma2-3bzlaz-es
81 gua-a24thima2-4pec-es
82 bhs-pyma2-phaz-es
83 gua-apma2-7 cmc-es
84 bhs-a23thima2-4phaz-es
85 bhs-penta-3bec-es
86 gua-aof-7 cmc-es
87 2py-a23thima2-phaz-ms
88 bim-dibema2-phaz-es
89 bim-35thima2-phec-as
90 bim-apma2-cpec-es
91 bhs-pipa2-3bec-nes
92 2py-pipa2-mmophec-es
93 bhs-35thima2-3bec-es
94 bhs-dibema2-phaz-es
95 gua-pipa2-3bec-es
96 bim-pipa2-phec-es
97 gua-42thiaz-phec-es
98 pippy-a24thima2-4pec-es
99 2py-35thima2-thec-es
100 2py-bam2-7 cmc-es
101 2py-35thima2-pmophec-es
102 bhs-dibema2-thec-es
103 bim-aof-4pec-es
104 bim-hexa-phec-es
105 2py-a24thima2-7 cmc-es
106 gua-a24thima2-phec-gs
107 gua-me25thima2-7 cmc-es
108 clim-a24thima2-7 cmc-es
109 gua-apma2-4pec-es
110 bim-35thima2-cpec-es
111 2py-me35thima2-thec-es
112 bhs-a24thima2-dbc-es
113 bim-bam2-4pec-es
114 amim-a24thima2-4pec-es
115 2py-dibema2-amec-es
116 2py-a23thima2-dbc-es
117 bim-bam2-4pec-ps
118 2py-ba m2-mmophec-es
119 bim-apma2-3bec-es
120 bhs-pdagk-thec-es
121 gua-42thiaz2-7 cmc-es
122 gua-a23thima2-thec-es
123 bim-apma2-4pec-es
124 thpym-35thima2-phec-es
125 bim-bam2-7 cmc-es
126 mam2py-bam2-4pec-es
127 bhs-edia2-3bec-es
128 bhs-a23thima2-amec-es
129 gua-dibema2-3bec-es
130 bim-me42thiaz2-7 cmc-es
131 bhs-a23thima2-phec-es
132 bim-dibema2-mpphec-es
133 2py-prodia2-thec-es
134 bhs-bam2-mophaz-es
135 bhs-a24thima2-7 cmc-es
136 im-dibema2-4pec-es
137 imhs-a24thima2-thec-es
138 bhs-a24thima2-dmaphec-es
139 2py-pipa2-dmaphec-es
140 2py-a24thima2-4pec-es
141 2py-dibema2-7 cmc-es
142 bhs-apma2-phaz-es
143 gua-pipa2-mophaz-es
144 dhim-dibema2-4pec-es
145 gua-pipa2-mpphec-es
146 bim-a23thima2-4pec-es
147 2py-dibema2-4phaz-es
148 bim-42thiaz2-4pec-es
149 am2py-dibema2-3bec-es
150 bim-pipa2-7 cmc-es
151 gua-bam2-dmaphec-es
152 bhs-pipa2-amec-es
153 2py-apma2-mpphec-es
154 2py-hexa-3bec-es
155 bim-apma2-7 cmc-es
156 bim-a23thima2-pclphec-es
157 gua-a24thima2-pclphec-es
158 bim-a23thima2-phec-es
159 bim-a24thima2-4pec-es
160 bhs-a23thima2-7 cmc-es
161 dimethpym-dibema2-phaz-es
162 2py-me25thima2-3bec-es
163 bhs-aof-thec-es
164 gua-dibema2-phec-f2es
165 amim-a23thima2-phec-es
166 2py-bam2-pclphec-es
167 bhs-pyma2-thec-es
168 2py-a24thima2-3bec-es
169 bim-bam2-phec-es
170 bim-35thima2-7 cmc-es
171 bhs-35thima2-pipmaz-es
172 bim-prodia2-phec-es
173 bim-35thima2-phec-es 174 gua-edia3-4pec-es
175 gua-a23thima2-ppec-es
176 gua-pipeme2-phec-es
177 gua-dibema2-phaz-es
178 2py-bam2-3bec-es
179 bhs-bam2-3bec-mals
180 mam2py-apma2-7 cmc-es
181 bhs-bam2-pmophec-es
182 gua-bam2-7 cmc-es
183 gua-buta-phec-es
184 bim-pyma2-7 cmc-es
185 2py-pipa2-thec-ms
186 bhs-dibema2-dmaphec-es
187 bim-a24thima2-ppec-es
188 am2py-bam2-7 cmc-es
189 bim-buta-7 cmc-es
190 im pipa2-phec-es
191 gua-dibema2-4pec-gs
192 2py-buta-thec-es
193 2py-pipa2-7 cmc-es
194 2py-apma2-phec-es
195 bim-pipa2-phec-gs
196 bim-me25thima2-phec-es
197 2py-pyma2-3bec-es
198 gua-bam2-pmophec-es
199 gua-35thima2-4pec-es
200 2py-pipeme2-thec-es
201 bhs-35thima2-phaz-f2es
202 bhs-edia3-phaz-es
203 2py-apma2-thec-pms
204 im apma2-phaz-es
205 bim-chex2-phec-es
206 bhs-35thima2-4pec-es
207 gua-a23thima2-phaz-es
208 2py-me25thima2-phaz-es
209 2py-a23thima2-pmophec-es
210 bhs-chex2-3bec-es
211 2py-dibema2-3ipec-es
212 2py-bam2-phec-es
213 bhs-dibema2-phec-es
214 bim-a24thima2-thec-es
215 bim-pipa2-thec-es
216 bhs-buta-phaz-es
217 bhs-mepipe2-phaz-es
218 gua-buta-4pec-es
219 am2py-a23thima2-phaz-es
220 gua-bam2-thec-es
221 gua-pdagk-4pec-es
222 bim-pdagk-phec-es
223 2py-35thima2-phec-es
224 gua-35thima2-7 cmc-es
225 gua-bam2-3bec-es
226 bhs-bam2-3bec-es
227 gua-a23thima2-7 cmc-es
228 bhs-aepi2-thec-es
229 clim-pipa2-7 cmc-es
230 2py-a23thima2-3bec-es
231 bim-a23thima2-3bzlaz-es
232 bhs-pipa2-3bec-es
233 bim-pipa2-mmphec-es
234 clim-dibema2-phec-es
235 bhs-aepi2-3bec-es
236 2py-apma2-4pec-es
237 dhim-a23thima2-7 cmc-es
238 bim-pipa2-pclphec-es
239 gua-mepipe2-7 cmc-es
240 gua-35thima2-3ipec-es
241 bhs-chex2-thec-es
242 bim-inda2-7 cmc-es
243 bhs-pipa2-phaz-es
244 imhs-pipa2-thec-es
245 gua-apma2-4phaz-es
246 gua-me25thima2-4pec-es
247 gua-35thima2-phec-es
248 bim-pipa2-amaz-es
249 2py-a24thima2-4phaz-es
250 2py-me42thiaz2-3bec-es
251 imhs-apma2-phec-es
252 bhs-pipeme2-thec-es
253 dhim-a24thima2-phec-es
254 2py-a23thima2-7 cmc-es
255 2py-pipa2-pymaz-es
256 2py-me35thima2-3bec-es
257 bim-apma2-7 cmc-as
258 bhs-35thima2-amaz-es
259 mam2py-dibema2-thec-es
260 dimethpym-apma2-4pec-es
261 bhs-bam2-4bec-es
262 2py-a23thima2-cpec-es
263 mam2py-35thima2-phec-es
264 am2py-apma2-phec-es
265 gua-a23thima2-4pec-es
266 bim-a24thima2-phec-es
267 2py-pipa2-thec-es
268 2py-dibema2-thec-es
269 pippy-pipa2-4pec-es
270 bim-dibema2-7 cmc-es
271 bim-dibema2-phec-es
272 gua-pdagk-7 cmc-es
273 bhs-35thima2-thec-es
274 bhs-a23thima2-mmphec-es
275 bhs-a23thima2-thec-nes
276 bim-me25thima2-7 cmc-es
277 2py-a24thima2-phec-es
278 gua-bam2-dbc-es
279 amim-dibema2-7 cmc-es
280 2py-a23thima2-4pec-es
281 thpym-dibema2-thec-es
282 2py-pipa2-phec-es
283 bhs-a24thima2-pymaz-es
284 gua-dibema2-amaz-es
285 dhim-bam2-3bec-es
286 gua-bam2-7 cmc-ms
287 bhs-edia3-thec-es
288 bim-a24thima2-phec-mals
289 bim-a24thima2-mophaz-es
290 gua-dibema2-phec-es
291 bhs-pipa2-4pec-es
292 bhs-apma2-pipmaz-es
293 gua-dibema2-pipmaz-es
294 gua-aepi2-4pec-es
295 gua-pipa2-ppec-es
296 bim-mea2-7 cmc-es
297 gua-pipa2-pmophec-es
298 imhs-bam2-7 cmc-es
299 gua-a24thima2-7 cmc-f2es
300 thpym-a23thima2-3bec-es
301 bim-mepipe2-7 cmc-es
302 thpym-pipa2-phaz-es
303 bim-aaf-7 cmc-es
304 bim-edia3-phec-es
305 2py-a24thima2-thec-es
306 bim-pipa2-phaz-es
307 dimethpym-bam2-phec-es 308 bim-a24thima2-phaz-es
309 bhs-bam2-phaz-pms
310 2py-35thima2-3bec-es
311 2py-35thima2-mophaz-es
312 gua-apma2-phaz-es
313 bim-apma2-phaz-es
314 gua-35thima2-7 cmc-nes
315 bhs-pipa2-phec-es
316 bhs-mepipe2-3bec-es
317 gua-pipa2-phaz-es
318 2py-a23thima2-phec-es
319 2py-pipa2-4pec-es
320 gua-apma2-mmphec-es
321 2py-apma2-7 cmc-es
322 bhs-a24thima2-phec-es
323 bhs-a23thima2-4pec-es
324 bim-35thima2-phaz-es
325 bim-pipeme2-7 cmc-es
326 bhs-42thiaz2-3bec-es
327 pippy-a23thima2-phec-es
328 2py-aof-thec-es
329 2py-pdagk-phaz-es
330 gua-aepi2-7 cmc-es
331 dimethpym-pipa2-3bec-es
332 gua-35thima2-amec-es
333 bhs-inda2-phaz-es
334 2py-pipeme2-3bec-es
335 gua-apma2-4pec-nes
336 gua-edia2-4pec-es
337 gua-a24thima2-phec-es
338 gua-apma2-3bec-es
339 gua-aaf-phec-es
340 gua-apma2-thec-es
341 bim-apma2-pymaz-es
342 im a24thima2-phec-es
343 2py-a24thima2-amec-es
344 bim-pdagk-7 cmc-es
345 bim-pipa2-3bzlaz-es
346 2py-mea2-phaz-es
347 amim-bam2-phaz-es
348 2py-pipa2-3bec-es
349 dhim-apma2-phaz-es
350 2py-35thima2-4pec-es
351 bhs-aof-3bec-es
352 2py-dibema2-phaz-nes
353 gua-a24thima2-3bec-es
354 bhs-dibema2-pymaz-es
355 bim-a24thima2-4bec-es
356 bhs-bam2-4pec-es
357 bim-35thima2-thec-es
358 gua-penta-phec-es
359 bim-buta-4pec-es
360 bhs-apma2-amaz-es
361 dimethpym-a24thima2-3bec-es
362 gua-a2-3thima2-7 cmc-mals
363 gua-dibema2-3bzlaz-es
364 2py-edia2-3bec-es
365 2py-aaf-thec-es
366 gua-a24thima2-7 cmc-es
367 2py-dibema2-mmphec-es
368 bhs-apma2-3bec-es
369 bim-dibema2-ppec-es
370 gua-35thima2-phaz-es
371 2py-me42thiaz2-thec-es
372 bim-35thima2-dbc-es
373 bhs-prodia2-3bec-es
374 gua-35thima2-mmphec-es
375 bhs-hexa-3bec-es
376 bhs-penta-phaz-es
377 dhim-pipa2-phec-es
378 gua-bam2-phec-es
379 2py-apma2-phaz-mals
380 bim-apma2-dbc-es
381 gua-inda2-phec-es
382 2py-bam2-thec-es
383 gua-pipa2-4bec-es
384 am2py-35thima2-4pec-es
385 bim-a24thima2-mpphec-es
386 2py-35thima2-4bec-es
387 bhs-pipa2-7 cmc-es
388 amim-pipa2-4pec-es
389 bhs-apma2-4pec-es
390 gua-a23thima2-phec-pms
391 bim-35thima2-4pec-es
392 bhs-a24thima2-thec-es
393 thpym-a24thima2-phaz-es
394 bim-mea2-phec-es
395 bim-a23thima2-thec-es
396 pippy-apma2-thec-es
397 2py-35thima2-ppec-es
398 im a23thima2-7 cmc-es
399 gua-mea2-4pec-es
400 gua-edia2-7 cmc-es
401 mam2py-pipa2-phaz-es
402 bhs-apma2-3bec-f2es
403 bim-aepi2-phec-es
404 2py-aepi2-phaz-es
405 2py-35thima2-thec-mals
406 2py-bam2-phaz-es
407 am2py-pipa2-thec-es
408 bhs-bam2-ppec-es
409 2py-dibema2-thec-ps
410 gua-pipa2-7 cmc-es
411 gua-bam2-4pec-as
412 bhs-apma2-thec-es
413 clim-35thima2-phaz-es
414 2py-bam2-amaz-es
415 bhs-pipa2-phaz-ps
416 gua-bam2-phaz-es
417 bhs-apma2-mmophec-es
418 gua-a24thima2-thec-es
419 gua-chex2-7 cmc-es
420 2py-penta-thec-es
421 2py-edia2-phaz-es
422 gua-pipa2-phec-es
423 bim-chex2-4pec-es
424 gua-dibema2-mmophec-es
425 2py-35thima2-phaz-es
426 bim-dibema2-mophaz-es
427 bim-me42thiaz2-4pec-es
428 2py-pyma2-phaz-es
429 bhs-a24thima2-3bec-es
430 2py-penta-phaz-es
431 bim-dibema2-pmophec-es
432 gua-pipa2-4pec-pms 433 bim-a23thima2-mmophec-es
434 2py-dibema2-phec-es
435 gua-a24thima2-pipmaz-es
436 bim-apma2-phec-es
437 bhs-pipa2-mpphec-es
438 gua-a23thima2-3bec-es
439 bim-a23thima2-amaz-es
440 bhs-dibema2-4pec-es
441 imhs-35thima2-4pec-es
442 imhs-a23thima2-phaz-es
443 bim-bam2-phec-nes
444 bhs-dibema2-3bec-es
445 bhs-a24thima2-phaz-es
446 gua-apma2-7 cmc-ps
447 amim-apma2-thec-es
448 bim-edia3-7 cmc-es
449 gua-bam2-cpec-es
450 gua-inda2-4pec-es
451 gua-edia3-phec-es
452 2py-pipa2-dbc-es
453 2py-a24thima2-mmphec-es
454 bim-pipa2-pipmaz-es
455 2py-a23thima2-dmaphec-es
456 bim-a23thima2-3bec-es
457 2py-pdagk-3bec-es
458 bim-dibema2-3bec-es
459 bim-apma2-thec-es
460 2py-bam2-4pec-es
461 bhs-me35thima2-3bec-es
462 gua-35thima2-3bec-es
463 pippy-35thima2-3bec-es
464 2py-bam2-3bec-gs
465 2py-bam2-3bzlaz-es
466 bhs-pipeme2-phaz-es
467 bim-mepipe2-4pec-es
468 bhs-dibema2-thec-as
469 2py-apma2-thec-es
470 bim-35thima2-3bec-es
471 bhs-me35thima2-phaz-es
472 bim-prodia2-4pec-es
473 bhs-mea2-phaz-es
474 gua-a24thima2-mmophec-es
475 gua-pipeme2-4pec-es
476 bim-a23thima2-phaz-es
477 gua-prodia2-phec-es
478 gua-dibema2-pclphec-es
479 bhs-aaf-phaz-es
480 2py-chex2-phaz-es
481 bim-35thima2-dmaphec-es
482 imhs-dibema2-3bec-es
483 2py-bam2-thec-f2es
484 bhs-35thima2-phec-es
485 bim-a23thima2-7 cmc-es
486 bhs-apma2-phec-es
487 bim-apma2-pmophec-es
488 bim-dibema2-7 cmc-pms
489 gua-35thima2-thec-es
490 bhs-pipa2-4phaz-es
491 2py-dibema2-phaz-es
492 bim-apma2-dmaphec-es
493 bim-edia2-phec-es
494 2py-dibema2-3bec-es
495 bhs-35thima2-mmphec-es
496 gua-apma2-phec-es
497 bim-bam2-amec-es
498 gua-apma2-amec-es
499 bhs-35thima2-7 cmc-es
500 bhs-me25thima2-thec-es
501 bhs-dibema2-7 cmc-es
502 gua-hexa-4pec-es
503 bim-bam2-3bec-es
504 bhs-pipa2-3ipec-es
505 2py-apma2-4bec-es
506 dimethpym-35thima2-7 cmc-es
507 bhs-bam2-phec-es
508 bhs-dibema2-3bec-ms
509 bhs-35thima2-3bzlaz-es
510 gua-penta-7 cmc-es
511 bhs-a23thima2-thec-es
512 clim-a23thima2-4pec-es
513 bhs-me42thiaz2-3bec-es
514 bhs-35thima2-phaz-es
515 bhs-a24thima2-4pec-es
516 bhs-a23thima2-phaz-es
517 bhs-bam2-thec-es
518 2py-35thima2-mpphec-es
519 bhs-dibema2-dbc-es
520 2py-35thima2-3bec-pms
521 2py-a24thima2-phaz-es
522 gua-aaf-7 cmc-es
523 gua-me42thiaz2-phec-es
524 bim-a23thima2-pipmaz-es
525 bim-a24thima2-7 cmc-es
526 im-bam2-3bec-es
527 bhs-a24thima2-cpec-es
528 bim-bam2-phaz-es
529 2py-apma2-mophaz-es
530 bim-pipa2-7 cmc-[2es
531 gua-a23thima2-mpphec-es
532 2py-a23thima2-3bec-as
533 gua-pyma2-4pec-es
534 2py-pipa2-phaz-es
535 2py-edia3-3bec-es
536 mam2py-a23thima2-3bec-es
537 2py-a24thima2-3ipec-es
538 2py-aof-phaz-es
539 gua-hexa-7 cmc-es
540 bhs-a23thima2-3bec-ps
541 bim-a24thima2-4pec-pms
542 bim-aaf-4pec-es
543 bhs-pipa2-thec-es
544 pippy-dibema2-7 cmc-es
545 gua-pipa2-thec-es
546 bhs-bam2-7 cmc-es
547 gua-bam2-4pec-es
548 bim-aepi2-4pec-es
549 2py-prodia2-phaz-es
550 2py-a23thima2-phaz-es
551 bim-35thima2-4pec-ms
552 bim-dibema2-4pec-mals
553 bhs-a24thima2-thec-ms
554 bim-42thiaz2-phec-es
555 2py-a24thima2-phaz-ps
556 bim-aof-phec-es
557 2py-a23thima2-pymaz-es
558 gua-a23thima2-mophaz-es
559 thpym-apma2-7 cmc-es
560 bim-bam2-3ipec-es
561 pippy-bam2-phaz-es
562 bim-dibema2-4pec-es In the above list, the following abbreviations are used for the structural units A, E, G and L.
| A = | Abbreviation |
|---|---|
| 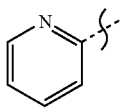 | 2py |
| 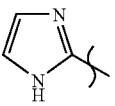 | dhim |
| 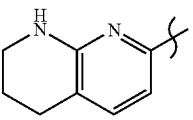 | bim |
| 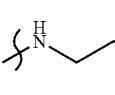 | imhs |
| 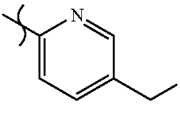 | dimethpym |
| 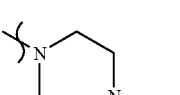 | mam2py |
|  | am2py |
| 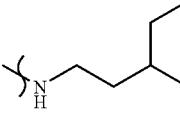 | thpym |
| 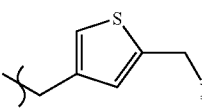 | bhs |
| 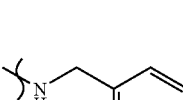 | gua |
|  | amim |
| 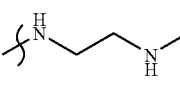 | clim |
| 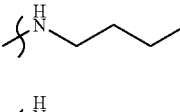 | im |
|  | pippy |
| E = | Abbreviation |
|---|---|
|  | edia2 |
|  | pyma2 |
|  | pipa2 |
|  | aepi2 |
|  | me35thima2 |
|  | dibema2 |
|  | edia3 |
|  | buta |
|  | aaf |

-continued

| Structure | Abbreviation |
|---|---|
| (thiazole-CH2-NH-C(=O)-) | 42thiaz2 |
| (cyclohexyl-NH-C(=O)-) | chex2 |
| (phenyl-CH2-NH-C(=O)-) | bam2 |
| (NH-phenyl-CH2-NH-C(=O)-) | apma2 |
| (NH-propyl-O-propyl-) | pdagk |
| (NH-CH2-piperidine-C(=O)-) | mepipe2 |
| (NH-propyl-NH-C(=O)-) | prodia2 |
| (isoindoline-CH2-NH-C(=O)-) | inda2 |
| (thiophene-CH2-NH-C(=O)-) | 35thima2 |
| (methyl-thiophene-CH2-NH-C(=O)-) | me25thima2 |
| (NH-pentyl-) | penta |
| (NH-ethyl-O-ethyl-) | aof |
| (NH-hexyl-) | hexa |
| (CH2-NH-C(=O)-) | mea2 |
| (piperidine-CH2-NH-C(=O)-) | pipeme2 |
| (methyl-thiazole-CH2-NH-C(=O)-) | me42thiaz2 |
| (NH-thiazole-CH2-NH-C(=O)-) | a23thima2 |
| (NH-thiazole-CH2-NH-C(=O)-) | a24thima2 |

The bond from structural element G to structural unit L should be understood as meaning a double bond in the compound where L=as.

| G = | Abbreviation |
|---|---|
| (phenyl-diazepinone) | 4phaz |
| (benzyl-diazepinone) | 3bzlaz |

-continued
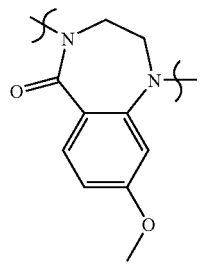 mophaz
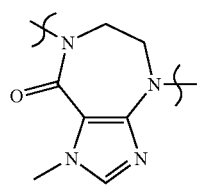 pipmaz
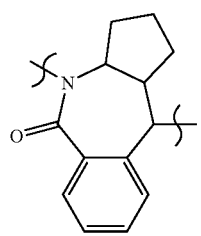 cpec
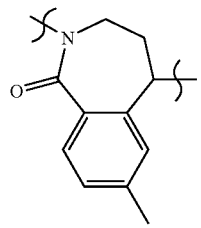 mpphec
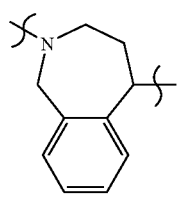 amec
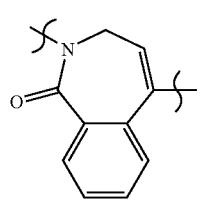 dbc
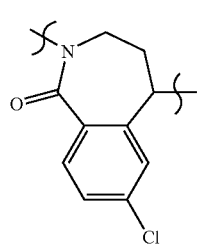 pclphec
-continued
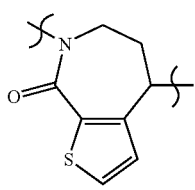 thec
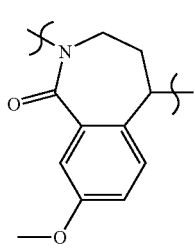 mmophec
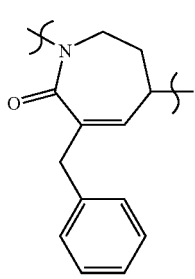 3bec
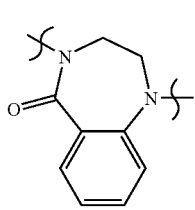 phaz
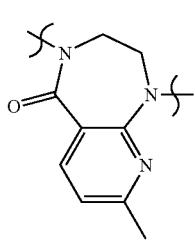 pymaz
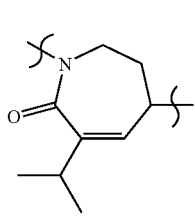 3ipec
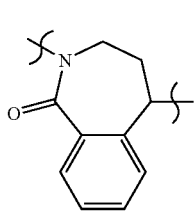 phec -continued
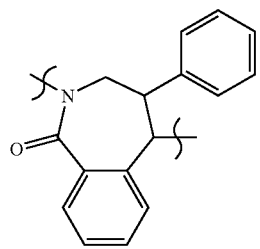 ppec
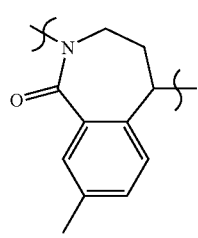 mmphec
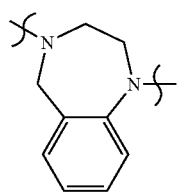 amaz
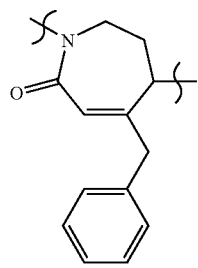 4bec
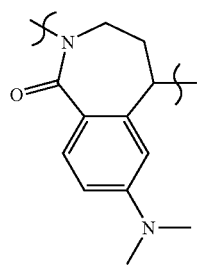 dmaphec
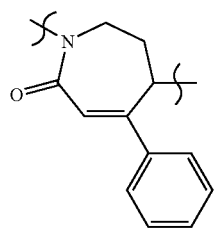 4pec
-continued
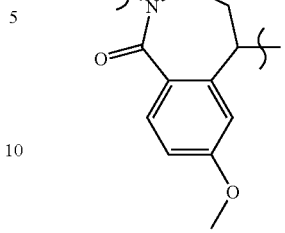 pmophec
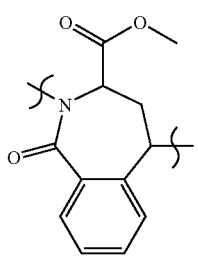 7cmc
| L = | Abbreviation |
|---|---|
| 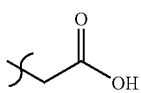 | es |
| 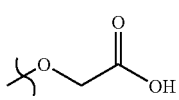 | gs |
| 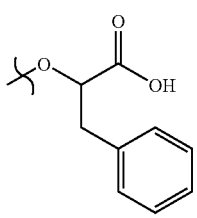 | pms |
| 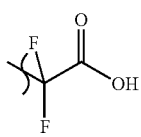 | f2es |
| 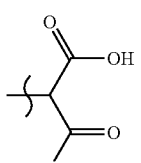 | mals |
| 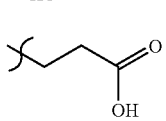 | ps |
| 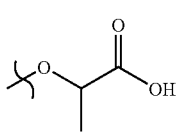 | ms |

-continued

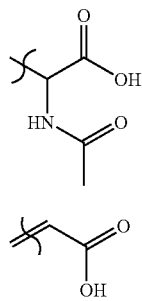

nes as

The compounds of the formula I and the starting substances used for their preparation can generally be prepared by methods of organic chemistry known to the person skilled in the art, such as are described in standard works such as Houben-Weyl (ed.), "*Methoden der Organischen Chemie*" [Methods of Organic Chemistry], Thieme-Verlag, Stuttgart, Taylor (ed.), "The Chemistry of Heterocyclic Compounds", Wiley & Sons, New York, or March "*Advanced Organic Chemistry*", $4^{th}$ Edition, Wiley & Sons. Further methods of preparing specific functional groups are also described in R. Larock, "Comprehensive Organic Transformations", Weinheim 1989, in particular the preparation of alkenes, alkynes, halides, amines, ethers, alcohols, phenols, aldehydes, ketones, nitrites, carboxylic acids, esters, amides and acid chlorides.

Generally, syntheses of the compounds of the formula I are possible in very different ways (Scheme 1). The linkage of the individual units A', E', G' or L', which are appropriately activated or modified compared with the structural elements A, E, G or L, can be carried out in any desired sequence (equations 1a+b). The linkage of subunits according to equation 2 is also possible, so that the synthesis of the molecules can also take place between parts of a structural element, for example between $E_I$ and $E_{II}$. The symbol """ in a unit or subunit stands for an activated unit or subunit or for a structural element which is synthesized, or contains a unit of the substructural elements which are removed again in the synthesis of the compounds of the formula I, such as leaving groups.

Scheme 1

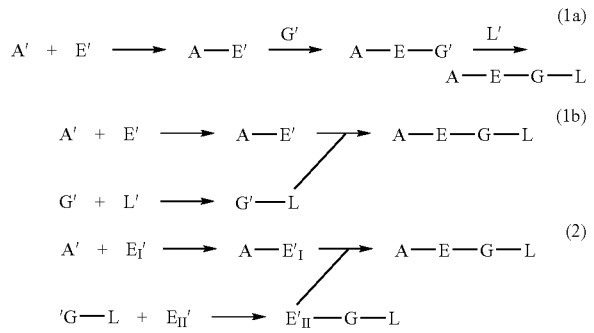

In these reactions, it is to be taken into account that protective groups possibly present in the subunits can be necessary, which have previously had to be introduced into the molecule and removed after the critical steps. A general survey of the protective groups, their introduction, stability and removal is given in Th. Greenes "Protective Groups in Organic Synthesis", Wiley & Sons, New York 1991. As a rule, the activation of the units in the sense of the desired reaction is possible by a number of reagents.

If not stated otherwise, all starting materials and reagents are commercially available, or can be prepared from commercially obtainable precursors according to customary or specific methods known from the literature (Beilstein).

Solvents which can be used are all customary inert solvents, such as hydrocarbons such as hexane, heptane, petroleum ether, toluene, benzene or xylene; chlorinated hydrocarbons such as trichloroethylene, 1,2-dichloroethane, carbon tetrachloride, chloroform, dichloromethane; alcohols such as methanol, ethanol, isopropanol, n-propanol, n-butanol or tert-butanol; ethers such as diethyl ether, methyl tert-butyl ether, diisopropyl ether, tetrahydrofuran, dioxane; glycol ethers such as ethylene glycol monomethyl ether or monoethyl ether, ethylene glycol dimethyl ether; ketones such as acetone, butanone; amides such as dimethylformamide (DMF), dimethylacetamide or acetamide; sulfoxides such as dimethyl sulfoxide, sulfolane; pyridine, N-methylpyrrolidone, 1,3-dimethyltetrahydro-2(1H)-pyrimidinone (DMPU), 1,3-dimethyl-2-imidazolidinone; nitriles such as acetonitrile or propionitrile; water, mixtures of the solvent mentioned or related mixtures such as organofluorine phases in combination with abovementioned solvents.

The synthesis of compounds of the formula I can either be carried out by the "classical" method in solution or on a polymer support, in each case reaction conditions being used such as are known and are suitable for the respective reactions. Use can also be made in this case of variants which are known per se, but not mentioned here.

Syntheses of the units G' can be found, for example, in "The Chemistry of Heterocyclic Compounds", Volume 50, "Bicyclic Diazepines" or Volume 43, "Azepines", Wiley & Sons, New York 1991. In order to demonstrate the breadth of possible application, exemplary literature syntheses of various substituted, aromatic and heteroaromatic azepinones and diazepinones are listed below:

J. Med. Chem. 39 (1996) 3539; Chem. Pharm. Bull 35 (1987) 3182; J. Heterocycl. Chem. 8 (1971) 231; J. Org. Chem. 29 (1964) 1998; J. Org. Chem. 30 (1965) 2100; Synth. Comm. 23 (1993) 895; Heterocycles 42 (1996) 83; J. Chem. Soc. Chem. Commun. 1980, 435; Aust. J. Chem. 43 (1990) 355; Chem. Ber. 87 (1954) 1811; Farmaco Ed. Sci. 30 (1975) 237; J. Heterocycl. Chem. 16 (1979) 213; Tetrahedron Lett. 32 (1991) 2469; Chem. Het. Compd. 26 (1990) 956; Arch. Pharm. 324 (1991) 141; Tetrahedron Lett. 1973, 1193; J. Am. Chem. Soc. 96 (1974) 4719; J. Org. Chem. 50 (1985) 1426; Liebigs Ann. 1985, 1099; J. Org. Chem. 64 (1999) 4411; Tetrahedron Lett. 29 (1988) 1071; Tetrahedron Lett. 1965, 1071; Tetrahedron 22 (1966) 1201

In Scheme 2, the use of such fragments in the case of the benzodiazepinones is shown. These can be doubly alkylated, for example, using esters of bromoacetic acid (J. Org. Chem. 1949, 14, 1099,; J. Am. Chem. Soc. 1952, 74, 1010), orthogonally cleavable diesters being accessible as in ST-7. These can be cleaved bilaterally and reacted with fragments A-$E_I$', as is shown here for one example. After the removal of possible protective groups, compounds according to the general formula I (here: ST-9) are obtained. It is demonstrated with ST-7 how the incorporation of the element G can take place in both orientations, in that alternatively both carboxylic acids are employed for the lengthening. In Scheme 2, it is also demonstrated how after introduction of a protective group SG₁ the selective alkylation of the amide nitrogen takes place to give compounds of the type ST-7a, which after removal of the protective group SG₁ opens up the possibility of synthesizing the compounds of the formula I using suitable fragments $R^4$—$X_{1g}$ (inter alia halides, alkoxysulfonic acid esters, carboxylic acids in activated form, sulfonic acid chlorides, isocyanates, chloroformic acid esters, where $X_{1g}$=leaving group) (ST-8).

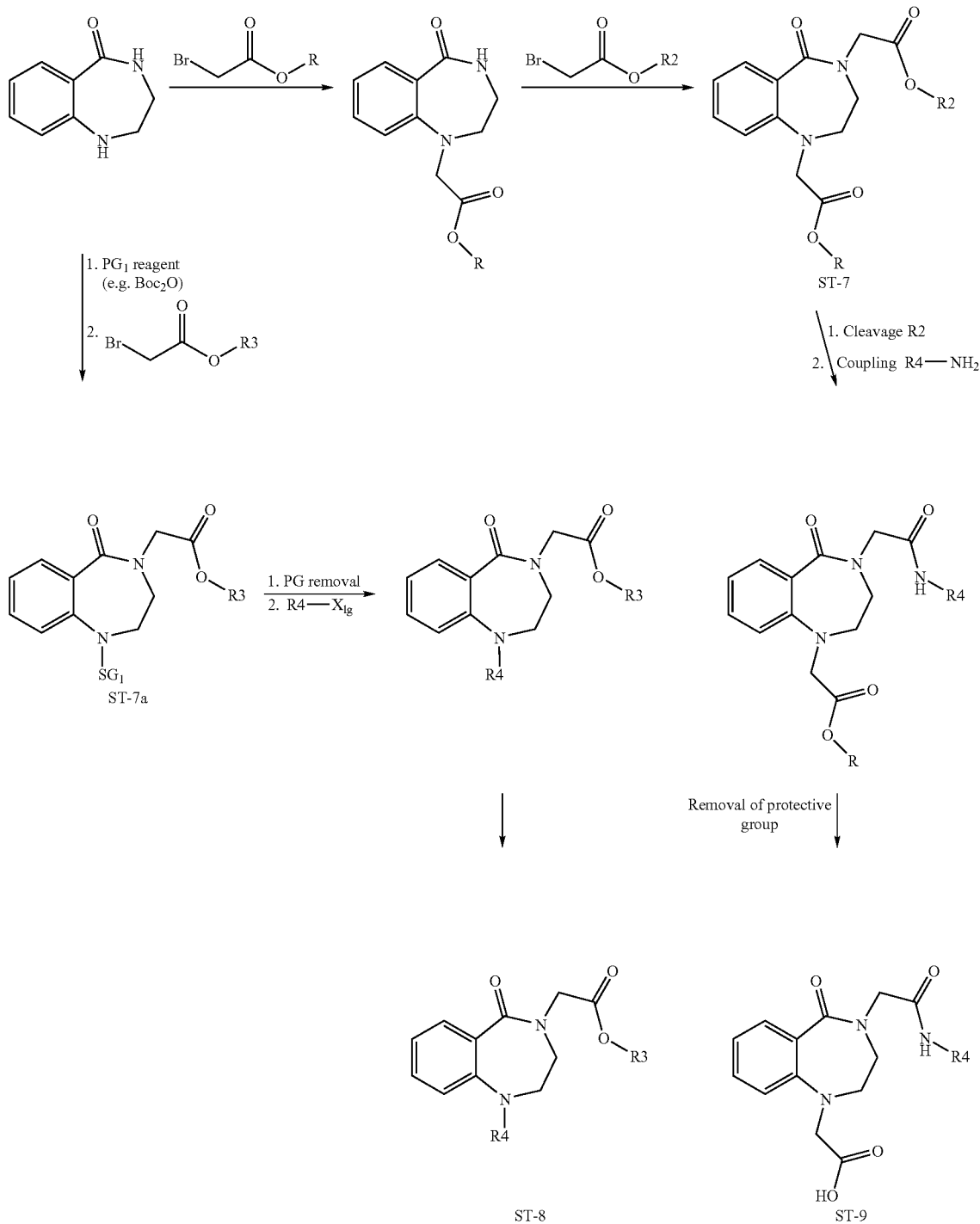

$X_{lg}$ = Leaving group

R4 = A—E′ fragment, possibly protected

The linkage of the units G to the adjacent fragments can also be carried out, for example, by Wittig/Horner reactions (starting from ketones). Structures of the type $W_G=I_{WG}^2$ to $I_{WG}^4$ are accessible thereby (Scheme 3, ST-10a-c). Synthesis of ethers is made possible by reduction of the ketone, for example with NaBH$_4$ (H. O. House, "Modern synthetic Reactions", Benjamin, N.Y. 1972, p. 42) and alkylation of the alcohol with suitable electrophiles (ST-11). Carrying out the reductive amination of the ketone, for example with NaBH$_3$(CN) or NaBH(OAc)$_3$ (J. Am. Chem. Soc. 1986, 108, 1039) leads to amines (ST-12).

roles; Vol. E7: Quinolines, pyridines, Vol. E8: Isoxazoles, oxazoles, thiazoles, pyrazoles, imidazoles and their benzo-fused representatives, and also oxadiazole, thiadiazoles and triazoles; Vol. E9: Pyridazines, pyrimidines, triazines, azepines and their benzo-fused representatives and also purines).

The synthesis of the units and fragments A' or the linkage thereof with the elements R-E' (where R is alternatively a part or the entire radical of the molecule corresponding to the general formula I) in some cases necessitates carrying out methods which are not generally known but which are

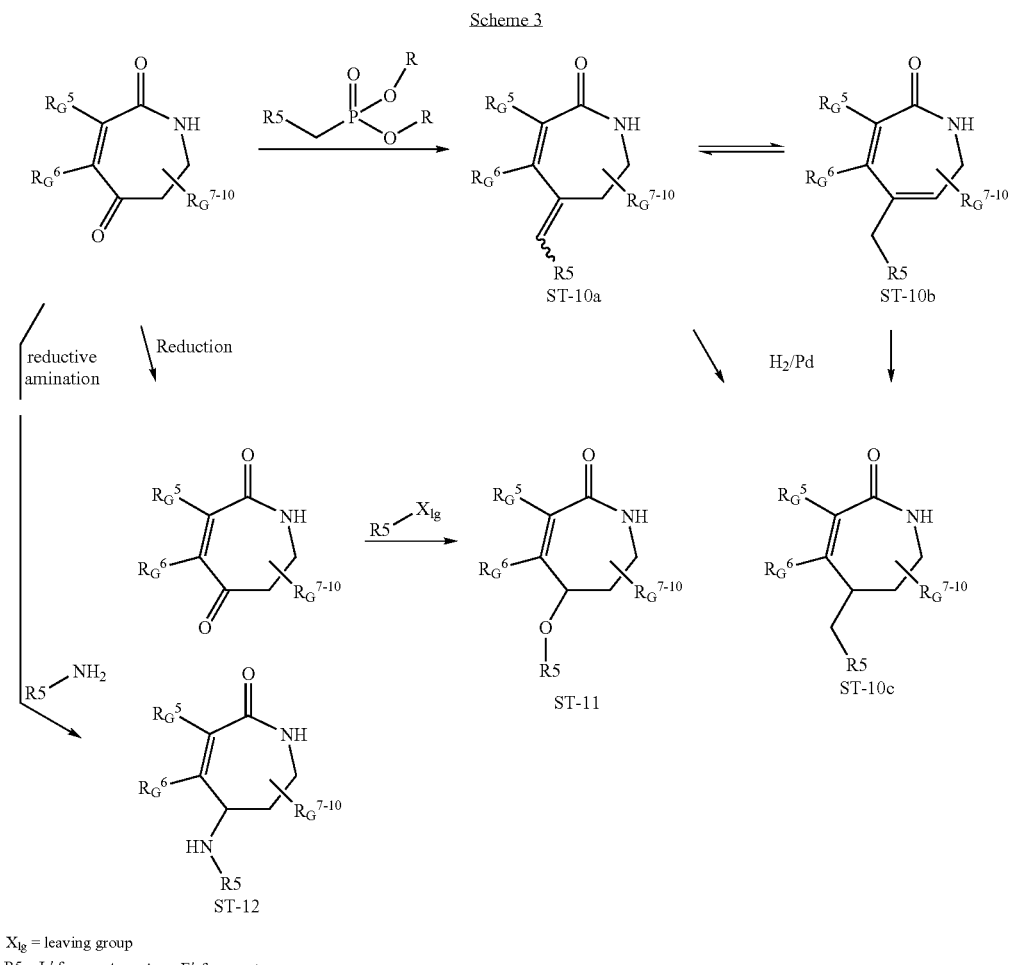

The synthesis of the units or fragments L' or E' needed is carried out by the already mentioned general methods of organic chemistry. The synthesis of some of these units is described by way of example in the experimental section. In the case in which the fragments $Q_E$ and $X_E$ are a hetaryl radical, the units used are either commercially available or accessible by methods known to the person skilled in the art. A large number of preparation methods are described in detail in Houben-Weyl's "Methoden der organischen Chemie" [Methods of organic chemistry] (Vol. E6: Furans, thiophenes, pyrroles, indoles, benzothiophenes, furans, -pyrdescribed in the literature, which should therefore be mentioned here. Some methods are also mentioned, for example, in the patent application WO 9708145. At the same time, use can also be made of variants known per se, but not mentioned here.

For the synthesis and linkage of the fragments A' to the fragments E' or $E_I'$, fragments or subfragments E' or $E_I'$, E'-G' or $E_I'$-G' or E'-G-L or $E_I'$-G-L of the general structure ST-13a-b can be used (Scheme 4). The nitrile in ST-13b is used here, for example, as a precursor for amines, imines, amidines, amides, carboxylic acids or N-containing heterocycles. Preferably, the nitrile is employed in the synthesis as an amine, amidine or heterocyclic precursor. Starting from the amines (ST-13a) and products of the nitrile reduction of ST-13b), it is possible to prepare, for example, aminoheteroaromatics, especially aminopyridines; aminopyrimidines; aminoazatetrahydroquinolines; aminoimidazoles, -benzimidazoles and also azabenzimidazoles; ureas; thioureas or guanidines.

Scheme 4

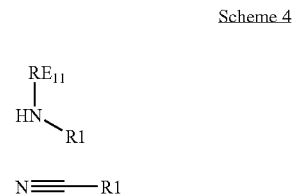

R1 = Fragment or subfragment E', E'—G', or E'—G—L

Scheme 5 shows examples of the reaction of the amines ST-13a (Blakemoore et al. *Eur. J. Med. Chem.* 1987 (22) 2, 91-100, Misra et al. *Bioorg. Med. Chem. Lett.* 1994 4 (18), 2165-2170).

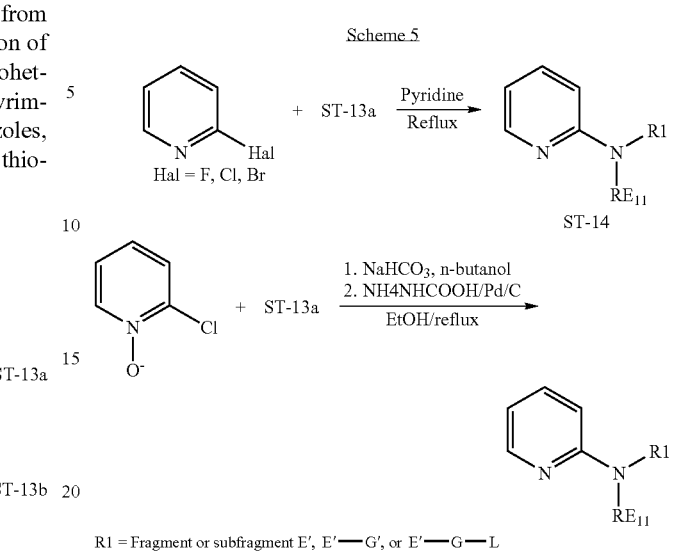

R1 = Fragment or subfragment E', E'—G', or E'—G—L

Various guanidine and amidine derivatives can be prepared by the methods shown in Scheme 6 by way of the example of the reactions of ST-13a (Synlett 1990, 745, *J. Org. Chem.* 1992, 57, 2497, *Bioorg. Med. Chem.* 1996, 6, 1185-1208; *Bioorg. Med. Chem.* 1998, 1185, oder *Synth. Comm.* 1998, 28, 741-746, *Tetrahedron Lett.* 1999, 40, 1103-1106, Applications US 3202660, Wo 9708145)

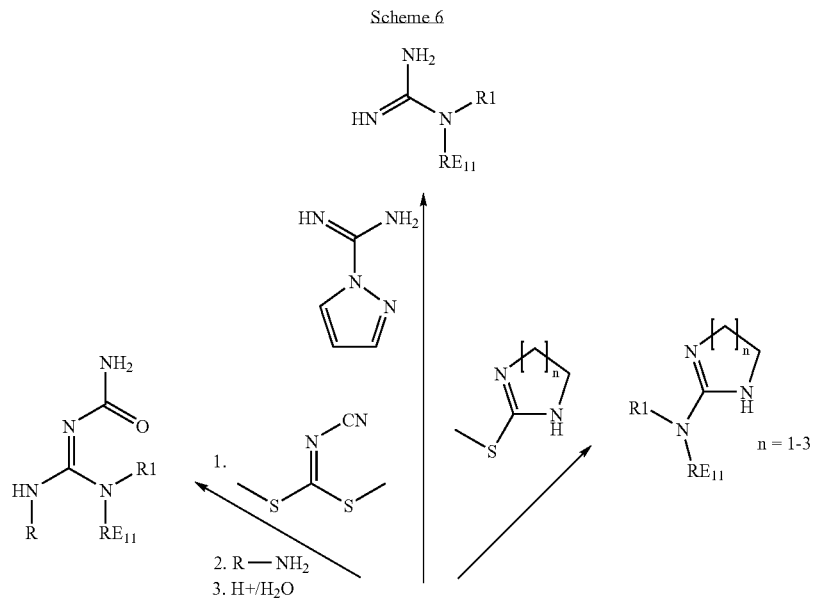

-continued

ST-13a

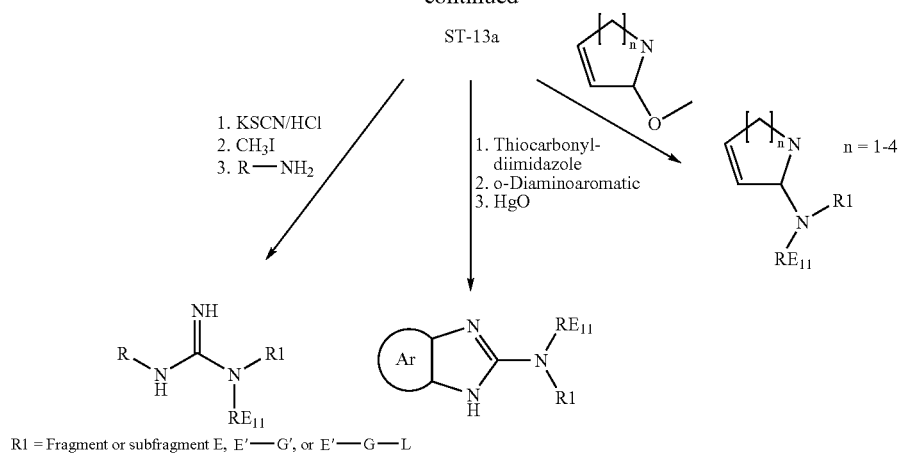

R1 = Fragment or subfragment E, E'—G', or E'—G—L

The following groups and subfragments A' or A'-R1 can be prepared, for example, by methods known from the literatur: ST-15 (*Phosphorus Sulfur Silicon Relat. Elem.* 1991, 63, 283-293), ST-16 (*Heterocycles* 1998, 15 N'-1, Spec. Issue, 341-344; WO 9736859), ST-17 (Synthesis 1981, 963-965, Synth. Comm. 1997, 27 (15), 2701-2707), ST-18 (J. Org. Chem. 1991, 56 (6), 2260-2262) (Scheme 7).

Scheme 7

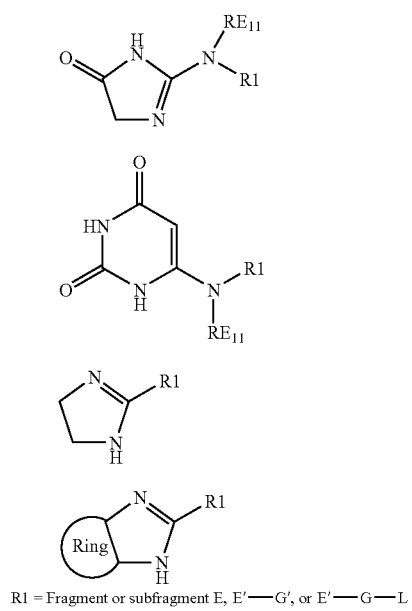

R1 = Fragment or subfragment E, E'—G', or E'—G—L

The invention further relates to the use of the structural element of the formula $I_{GL}$

-G-L          $I_{GL}$ for the preparation of compounds which bind to integrin receptors.

The invention further relates to drugs comprising the structural element of the formula $I_{GL}$.

The invention further relates to pharmaceutical preparations, comprising at least one compound of the formula I in addition to the customary pharmaceutical excipients.

The compounds according to the invention can be administered orally or parenterally (subcutaneously, intravenously, intramuscularly, intraperitoneally) in the customary manner. Administration can also be carried out through the nasopharynx using vapors or sprays. Further, the compounds according to the invention can be introduced by direct contact with the affected tissue.

The dose depends on the age, condition and weight of the patient and on the manner of administration. As a rule, the daily dose of active compound is between approximately 0.5 and 50 mg/kg of body weight in the case of oral administration and between approximately 0.1 and 10 mg/kg of body weight in the case of parenteral administration.

The novel compounds can be administered in solid or liquid form in the customary pharmaceutical administration forms, e.g. as tablets, film-coated tablet, capsules, powders, granules, coated tablets, suppositories, solutions, ointments, creams or sprays. These are prepared in a customary manner. The active compounds can in this case be processed using the customary pharmaceutical excipients such as tablet binders, fillers, preservatives, tablet disintegrants, flow regulators, plasticizers, wetting agents, dispersants, emulsifiers, solvents, release-delaying agents, antioxidants and/or propellants (cf. H. Sucker et al.: Pharmazeutische Technologie, Thieme-Verlag, Stuttgart, 1991). The administration forms thus obtained normally contain the active compound in an amount from 0.1 to 90% by weight.

The invention further relates to the use of compounds of the formula I for the production of drugs for treating illnesses. The compounds of the formula I can be used for treating human and animal illnesses. The compounds of the formula I bind integrin receptors. They are therefore preferably suitable as integrin receptor ligands and for the production of drugs for treating illnesses in which an integrin receptor is involved, in particular for the treatment of illnesses in which the interaction between integrins and their natural ligands is dysregulated, i.e. excessive or reduced.

Integrin receptor ligands are understood as meaning agonists and antagonists.

An excessive or decreased interaction is understood as meaning both an excessive or decreased expression of the natural ligand and/or of the integrin receptor and thus an excessive or decreased amount of natural ligand and/or integrin receptor or an increased or decreased affinity of the natural ligand for the integrin receptor.

The interaction between integrins and their natural ligands is dysregulated compared with the normal state, i.e. excessive or decreased, if this dysregulation does not correspond to the physiological state. An increased or decreased interaction can lead to pathophysiological situations.

The level of dysregulation which leads to a pathophysiological situation is dependent on the individual organism and on the site and nature of the disorder.

Preferred integrin receptors for which the compounds of the formula I according to the invention can be used are the $\alpha_5\beta_1$, $\alpha_4\beta_1$, $gp_{IIb}\beta_3$, $\alpha_v\beta_5$ and $\alpha_v\beta_3$ integrin receptors.

The compounds of the formula I particularly preferably bind to the $\alpha_v\beta_3$ integrin receptor and can thus be particularly preferably used as ligands of the $\alpha_v\beta_3$ integrin receptor and for the treatment of illnesses in which the interaction between $\alpha_v\beta_3$ integrin receptor and its natural ligand is excessive or reduced.

The compounds of the formula I are preferably used for the treatment of the following illnesses:
cardiovascular disorders-such as atherosclerosis, restenosis after vascular injury or stent implantation, and angioplasty (neointima formation, smooth muscle cell migration and proliferation),
acute kidney failure,
angiogenesis-associated microangiopathies such as diabetic angiopathies or retinopathy or rheumatoid arthritis,
blood platelet-mediated vascular occlusion, arterial thrombosis,
stroke, reperfusion damage after myocardial infarct or stroke,
carcinomatous disorders, such as in tumor metastasis or in tumor growth (tumor-induced angiogenesis),
osteoporosis (bone resorption after chemotaxis and adhesion of osteoclasts to the bone matrix),
high blood pressure, psoriasis, hyperparathyroidism, Paget's disease, malignant hypercalcemia, metastatic osteolytic lesions, inflammation, wound healing, cardiac insufficiency, congestive heart failure CHF, as well as in
antiviral, antimycotic, antiparasitic or antibacterial therapy and prophylaxis (adhesion and internalization).

Advantageously, the compounds of the formula I can be administered in combination with at least one further compound in order to achieve an improved curative action in a number of indications. These further compounds can have the same or a different mechanism of action as/from the compounds of the formula I.

In addition to the compounds of the formula I and the customary pharmaceutical incipients, the pharmaceutical preparations can therefore contain at least one further compound, depending on the indication, in each case selected from one of the 10 groups below.

Group 1:
inhibitors of blood platelelet adhesion, activation or aggregation, such as acetylsalicylic acid, lysine acetylsalicylate, piracetam, dipyridamol, abciximab, thromboxane antagonists, fibrinogen antagonists, such as tirofiban, or inhibitors of ADP-induced aggregation such as ticlopidine or clopidogrel,
anticoagulants which prevent thrombin activity or formation, such as inhibitors of IIa, Xa, XIa, IXa or VIIa,
antagonists of blood platelet-activating compounds and selectin antagonists
for the treatment of blood platelet-mediated vascular occlusion or thrombosis, or Group 2:
inhibitors of blood platelet activation or aggregation, such as GPIIb/IIIa antagonists, thrombin or factor Xa inhibitors or ADP receptor antagonists,
serine protease inhibitors,
fibrinogen-lowering compounds,
selectin antagonists,
antagonists of ICAM-1 or VCAM-1 inhibitors of leukocyte adhesion
inhibitors of vascular wall transmigration,
fibrinolysis-modulating compounds, such as streptokinase, tPA,
plasminogen-activating stimulants, TAFI inhibitors, XIa inhibitors or PAI-1 antagonists,
inhibitors of complement factors,
endothelin receptor antagonists,
tyrosine kinase inhibitors,
antioxidants and
interleukin 8 antagonists
for the treatment of myocardial infarct or stroke, or Group 3:
endothelin antagonists,
ACE inhibitors,
angiotensin receptor antagonists,
endopeptidase inhibitors,
beta-blockers,
calcium channel antagonists,
phosphodiesterase inhibitors and
caspase inhibitors
for the treatment of congestive heart failure, or Group 4:
thrombin inhibitors,
inhibitors of factor Xa,
inhibitors of the coagulation pathway which leads to thrombin formation, such as heparin or low-molecular weight heparins, inhibitors of blood platelet adhesion, activation or aggregation, such as GPIIb-IIIa antagonists or antagonists of the blood platelet adhesion and activation mediated by vWF or GPIb,
endothelin receptor antagonists,
nitrogen oxide synthase inhibitors,
CD44 antagonists,
selectin antagonists,
MCP-1 antagonists,
inhibitors of signal transduction in proliferating cells, antagonists of the cell response mediated by EGF, PDGF, VEGF or bFGF and
antioxidants
for the treatment of restenosis after vascular injury or stent implantation, or Group 5:
antagonists of the cell response mediated by EGF, PDGF, VEGF or bFGF,
heparin or low-molecular weight heparins or further GAGs,
inhibitors of MMPs,
selectin antagonists,
endothelin antagonists,
ACE inhibitors,
angiotensin receptor antagonists and
glycosylation inhibitors or AGE formation inhibitors or AGE breakers and antagonists of their receptors, such as RAGE,
for the treatment of diabetic angiopathies or Group 6:
lipid-lowering compounds,
selectin antagonists,
antagonists of ICAM-1 or VCAM-1
heparin or low-molecular weight heparins or further GAGs,
inhibitors of MMPs,
endothelin antagonists,
apolipoprotein A1 antagonists,
cholesterol antagonists,
HMG CoA reductase inhibitors,
ACAT inhibitors,
ACE inhibitors,
angiotensin receptor antagonists,
tyrosine kinase inhibitors,
protein kinase C inhibitors,
calcium channel antagonists,
LDL receptor function stimulants,
antioxidants
LCAT mimetics and
free radical scavengers
for the treatment of atherosclerosis or Group 7:
cytostatic or antineoplastic compounds,
compounds which inhibit proliferation, such as kinase inhibitors and
heparin or low-molecular weight heparins or further GAGs
for the treatment of cancer, preferably for the inhibition of tumor growth or metastasis, or Group 8:
compounds for antiresorptive therapy,
compounds for hormone exchange therapy, such as estrogen or
progesterone antagonists,
recombinant human growth hormone,
bisphosphonates, such as alendronates
compounds for calcitonin therapy,
calcitonin stimulants,
calcium channel antagonists,
bone formation stimulants, such as growth factor agonists,
interleukin-6 antagonists and
Src tyrosine kinase inhibitors
for the treatment of osteoporosis or Group 9:
TNF antagonists,
antagonists of VLA-4 or VCAM-1,
antagonists of LFA-1, Mac-1 or ICAMs,
complement inhibitors,
immunosuppressants,
interleukin-1, -5 or -8 antagonists and
dihydrofolate reductase inhibitors
for the treatment of rheumatoid arthritis or Group 10:
collagenase,
PDGF antagonists and
MMPs
for improved wound healing.

A pharmaceutical preparation comprising at least one compound of the formula I, if appropriate pharmaceutical excipients and at least one further compound, depending on the indication, in each case selected from one of the above groups, is understood as meaning a combined administration of at least one of the compounds of the formula I with at least one further compound in each case selected from one of the groups described above and, if appropriate, pharmaceutical excipients.

Combined administration can be carried out by means of a substance mixture comprising at least one compound of the formula I, if appropriate pharmaceutical excipients and at least one further compound, depending on the indication, in each case selected from one of the above groups, but also spatially and/or chronologically separate.

In the case of the spatially and/or chronologically separate administration, the administration of the components of the pharmaceutical preparation, the compounds of the formula I and the compounds selected from one of the abovementioned groups takes place spatially and/or chronologically separately.

For the treatment of restenosis after vascular injury or stenting, the administrations of the compounds of the formula I can be carried out locally at the affected sites, on their own or in combination with at least one compound selected from group 4. It may also be advantageous to coat the stents with these compounds.

For the treatment of osteoporosis, it may be advantageous to carry out the administration of the compounds of the formula I in combination with an antiresorptive or hormone exchange therapy.

The invention accordingly relates to the use of the abovementioned pharmaceutical preparations for the production of drugs for treating illnesses.

In a preferred embodiment, the invention relates to the use of the abovementioned combined pharmaceutical preparations for the production of drugs for treating
blood platelet-mediated vascular occlusion or thrombosis
when using compounds of group 1,
myocardial infarct or stroke
when using compounds of group 2,
congestive heart failure
when using compounds of group 3,
restenosis after vascular injury or stent implantation
when using compounds of group 4,
diabetic angiopathies
when using compounds of group 5,
atherosclerosis
when using compounds of group 6,
cancer
when using compounds of group 7,
osteoporosis
when using compounds of group 8,
rheumatoid arthritis
when using compounds of group 9,
wound healing
when using compounds of group 10.

The following examples illustrate the invention, the selection of these examples being non-limiting.

I. SYNTHESIS EXAMPLES

I. A Precursors

Example 1 tert-Butyl (2E/Z)-(1-oxo-1,2,3,4-tetrahydro-5H-2-benzazepin-5-ylidene)ethanoate (1)

A solution of 8.8 g (35 mmol) of t-butyl diethylphosphonate in 12 ml of DME was added dropwise at 0° C. to a suspension of 1.4 g of NaH (50%, deoiled) in 12 ml of DMF and the mixture was stirred until the appearance of a clear yellow solution. Subsequently 25 ml of a DMF solution of 5.2 g (29.7 mmol) of 3,4-dihydro-1H-2-benzazepin-1,5

(2H)-dione (Tetrahedron Lett. 1993, 34, 5855) were added dropwise at 0-5° C. and the mixture was stirred for 3.5 h, the reaction solution being allowed to rise to room temperature. For work-up, it was poured into 300 ml of cold 5% strength NaCl solution, the deposited product was extracted 4 times and with ethyl acetate, and the combined ethyl acetate phases were washed with 5% strength $Na_2CO_3$ and sodium chloride solution, dried over $Na_2SO_4$ and concentrated in vacuo to give a viscous yellow oil residue. The E/Z mixture was employed in the subsequent hydrogenation without further purification.

Example 2 tert-Butyl (1-oxo-2,3,4,5-tetrahydro-1H-2-benzazepin-5-yl)-acetate (2)

A suspension of 2.5 g of 10% strength Pd/C in 30 ml of ethanol was prehydrogenated, then a solution of compound 1 in 80 ml of ethanol was added and the mixture was hydrogenated under normal conditions until the completion of hydrogen absorption. After filtering off with suction and washing the catalyst with ethanol, the filtrate was concentrated in vacuo, the oily residue was dissolved in diethyl ether and the crystallization which began was completed by addition of n-hexane. After filtering off the precipitate with suction and washing it with n-hexane, 6.8 g (83.4%, stages 1 and 2) of white crystals, m.p. 126-127° C., FAB-MS [M–H$^+$]: 276, were isolated.

Example 3

[5-(2-tert-Butoxy-2-oxoethyl)-1-oxo-1,3,4,5-tetrahydro-2H-2-benzazepin-2-yl]acetic acid (3)

A solution of 6.28 g (22.8 mmol) of compound 2 in 25 ml of DMF was added dropwise at 0-3° C. to a suspension of 0.96 g of NaH (60%, deoiled) in 12 ml of DMF and the mixture was stirred until the appearance of a clear yellowish solution. 3.7 g (23.1 mmol) of methyl bromoacetate were then added at 5-10° C. and the mixture was stirred for 40 min, the reaction solution being allowed to rise to room temperature. The reaction solution was poured into cold 5% strength NaCl solution, extracted 3 times with 100 ml of ether each time, and the combined ether extracts were washed with 5% strength $K_2CO_3$ and sodium chloride solution, dried over $Na_2SO_4$ and concentrated to dryness. The viscous yellow oil residue was employed directly in the subsequent hydrolysis.

Compound 3a was dissolved in 35 ml of dioxane and 23 ml of 1 N NaOH were added dropwise at room temperature with stirring. After 1 h, the reaction solution was adjusted to pH 7, the dioxane was largely distilled off in vacuo, the residue was diluted with water, and the mixture was brought to pH 9 using 1 N NaOH and extracted repeatedly with ether. The aqueous phase was rendered acidic (pH 2.5) with 1 N $KHSO_4$ solution, the depositing acid was extracted with an ether/ethyl acetate mixture (4/1), the organic phase was washed with 0.5% strength $KHSO_4$ and NaCl solution and dried over $Na_2SO_4$, and the solvent was stripped off. The viscous, oily residue was dissolved in a $CH_2Cl_2$/ether mixture (1/1), the solution was concentrated in vacuo and the residue was crystallized by addition of water-saturated n-hexane. After filtering off with suction and washing with n-hexane, 5.2 g (68%, based on stages 3a) and b)) of white crystals remained; m.p. 135-137° C., FAB-MS [M–H$^+$]: 334.

Example 4

N-[4-(Aminomethyl)phenyl]-1H-benzimidazol-2-amine(hydrochloride) (4)

a) 20 g of tert-butyl 4-aminobenzyl carbamate (89.97 mmol)—dissolved in 100 ml of $CH_3CN$— were added dropwise at 0° C. to a solution of 24.5 g of thiocarbonyldiimidazole and 1.56 g of imidazole in 600 ml of $CH_3CN$ and the mixture was stirred at RT overnight. 19.5 g of 1,2-phenylenediamine were then added and the mixture was again stirred at RT for 2 h. For work-up, the reaction mixture was evaporated in vacuo, the residue was taken up in $CH_2Cl_2$, and the solution was washed 7× with 10% citric acid solution and 2× with satd. NaCl solution, dried over $Na_2SO_4$, filtered and concentrated. Th crude product thus obtained (31.78 g; brown foam) was reacted directly without further purification; ESI-MS [M+H$^+$] =373.15.

$^1$H-NMR (360 MHz, DMSO) δ ppm: 9.5 and 9.05 (each s, 1H), 7.45 (d, 2H), 7.35 (m, 1H), 7.20 (d, 1H), 7.15, 6.95, 6.75, 6.60 (each m, 1H), 4.85 (s, 2H), 4.10 (d, 2H), 1.35 (s, 9H).

b) Crude product 4a was dissolved in 750 ml of ethanol together with 36.7 g of HgO (yellow) and 0.4 g of sulfur and heated to reflux for 2 h. The reaction mixture was then filtered twice through Celite and evaporated to dryness; 20.7 g, ESI-MS [M+H$^+$]=339.15.

c) 7 g of the crude product 4b were introduced into 70 ml of $CH_2Cl_2$, 35 ml of HCl in diethyl ether (satd. at 0° C.) were added and the mixture was stirred at RT for 2 h. The resulting precipitate was filtered off with suction, washed with $CH_2Cl_2$ and dried.

6.7 g of brown amorphous solid; ESI-MS [M+H$^+$] =239.15. 1H-NMR (360 MHz, DMSO) δ ppm: 11.6 (s broad, 1H), 8.4 (s broad, 3H), 8.25 (s broad, 1H), 7.65 and 7.55 (each d, 2H), 7.45 and 7.3 (each m, 2H), 4.19 (m, 2H).

Example 5

25 N-[4-(Aminomethyl)phenyl]-N'-benzylurea (5)

a) 4-Aminobenzylamine (10.0 g, 81.85 mmol) in 150 ml $CH_2Cl_2$ was treated with triethylamine (6.8 g, 67.12 mmol) and then treated at 0° C. with di-t-butyl dicarbonate (18.6 g, 85.0 mmol). The mixture was stirred at 0° C. for 1 h and then at RT for 2 h. For work-up, 150 ml of a 1% aqueous citric acid solution were added, the phases were separated and the aqueous phase was reextracted times with $CH_2Cl_2$ (150 ml). Fresh washing with $H_2O$, drying of the combined organic phases using $Na_2SO_4$ and evaporation afforded a solid, which was washed with stirring with a little diisopropyl ether, filtered off with suction and dried.

13.0 g; ESI-MS [M+H+-tBu]=167.05. $^1$H-NMR (360 MHz, CDCl$_3$) 6 (ppm): 7.04 (2H, d), 6.61 (2H, d), 4.78 (1H, s br.), 4.17 (2H, d), 3.67 (2H, s br.), 1.46 (9H, s).

b) Benzyl isocyanate (2.40 g, 18.0 mmol) was added with ice-cooling to a solution of the protected amine 5a (4.0 g, 17.99 mmol) and triethylamine (1.82 g, 18.0 mmol) in 220 ml of toluene/DMF 10:1. The reaction mixture was stirred at RT overnight. Some of the urea formed was filtered off directly as a precipitate and dried. The filtrate was washed 2×mit $H_2O$, with diluted tartaric acid to pH 3 and again 2 times with $H_2O$ to pH 5, and the organic phase was then dried and evaporat d. Altogether, 6.0 g were thus obtained; ESI-MS [M+H$^+$-$^t$Bu]=300.15.

c) The urea 5b thus obtained was introduced in 90 ml of $CH_2Cl_2$, and TFA (2.24 g, 196.25 mmol)—dissolved in 90 ml of $CH_2Cl_2$—was added dropwise at 0° C. After 3 h, 1 ml of TFA was added again, then the mixture was stirred at RT overnight. After fresh addition of 1 ml of TFA, the mixture was stirred for a further 5 h, then poured onto ice water and extracted with ethyl acetate (2×50 ml). The water phase was rendered basic with 2N NaOH solution and extracted with $CH_2Cl_2$ (2×50 ml). The insoluble portion between the phases was filtered off and dried. 4 g; ESI-MS [2M+H$^+$]=511.35.

1H-NMR (200 MHz, DMSO) δ (ppm): 8.52 (1H, s), 7.39-7.07 (9H, m), 6.62 (1H, t), 4.27 (2H, d), 3.61 (2H, s).

Example 6 trans-N-[(4-Aminocyclohexyl)methyl]-1H-benzimidazole-2-amine (dihydrochloride) (6)

Preparation was carried out analogously to compound 4 starting from 5.4 g of tert-butyl 4-(aminomethyl)cyclohexylcarbamate (WO 9603374; Bioorg. Med. Chem. Lett. 1997, 7(1), 67). After removal of the Boc group, 3.3 g of white dihydrochloride were isolated; FAB-MS [M+H$^+$]: 245.

Example 7 trans-N-[4-(Aminomethyl)cyclohexyl]-1H-benzimidazole-2-amine (dihydrochloride) (7)

Preparation was carried out analogously to compound 4 starting from 10 g of benzyl {4-[(tert-butoxycarbonyl)amino]cyclohexyl}methylcarbamate (EP 669317) by removal of the Boc group using 4N HCl in dioxane, synthesis of the benzimidazole and subsequent hydrolysis. 3.6 g of white dihydrochloride were isolated; FAB-MS [M+H$^+$]: 245.

Example 8

$N^1$-(1H-Benzimidazol-2-yl)pentane-1,5-diamine (hydrochloride) (8)

Preparation was carried out analogously to the preparation of compound 4 starting from 7 g of N-Boc-1,5-diaminopentane hydrochloride (J. Chem. Res., Synop. 1996, 8, 366; J. Med. Chem. 1999, 42, 4380; 29.3 mmol). After reaction analogously to 4a, 10.3 g of N-Boc 5-{[(2-aminoanilino)carbothioyl]amino}pentane-1-amine were obtained; ESI-MS [M+H$^+$]: 353.25. Cyclodesulfurization and subsequent removal of the Boc group using TFA afforded an oily crude product, which was taken up in $CH_3OH$ and coverted into the corresponding hydrochloride using 250 ml of ethereal HCl (saturated at 0° C.). Stirring the solid obtained with a mixture of $CH_3OH$/methyl t-butyl ether afforded 1.8 g of a reddish amorphous solid; $^1$H-NMR (360 MHz, DMSO) δ ppm: 9.30 (t, 1H), 8.15 (s broad, 3H), 7.40 and 7.25 (each m, 2H), 3.35 (m, 2H superimposed with $H_2O$ peak), 2.80 (m, 2H), 1.65 (m, 4H), 1.45 (m, 2H).

Example 9

$N^1$-(1H-Benzimidazol-2-yl)butane-1,4-diamine(trifluoroacetate) (9)

Preparation was carried out analogously to the preparation of compound 4 starting from 9.87 g of N-Boc-1,4-diaminobutane (52.3 mmol). After reaction analogously to 4a, 17.08 g of N-Boc 4-{[(2-aminoanilino)carbothioyl]amino}butane-1-amine were obtained; ESI-MS [M+H$^+$]: 338.99. Cyclodesulfurization and subsequent removal of the Boc group using TFA afforded a brown solid, which was stirred a number of times with n-pentane and then recrystallized from a mixture of $CH_3OH$/methyl t-butyl ether; 14.35 g, ESI-MS [M+H$^+$]: 205.15.

$^1$H-NMR (360 MHz, DMSO) δ ppm: 9.20 (t, 1H), 7.80 (s broad, 3H), 7.35 and 7.20 (each m, 2H), 3.40 (m, 2H partly superimposed with $H_2O$ peak), 2.80 (m, 2H), 1.65 (m, 4H).

Example 10

$N^1$-(1H-Benzimidazol-2-yl)propane-1,3-diamine (10)

Carrying out analogously to compound 4 starting from N-Boc-diaminopropane (4.99 g, 28.64 mmol), reaction with thiocarbonyldiimidazole and subsequently 1,2-phenylenediamine afforded 8.4 g of tert-butyl 3-{[(2-aminoanilino)carbothioyl]amino}propylcarbamate (ESI-MS; [M+H$^+$]: 325.15), which was then converted with HgO/cat. S into the corresponding aminobenzimidazole (6.4 g; ESI-MS; [M+H$^+$]: 291.15). After removal of the Boc group using TFA, the crude product obtained was boiled in $CH_3OH$ with addition of active carbon, filtered, evaporated and crystallized from $CH_3OH$/methyl t-butyl ether; 6 g of beige solid; ESI-MS; [M+H$^+$]: 191.1.

I.B Compounds of the Formula I

Example I tert-Butyl [2-(2-{[4-(1H-benzimidazol-2-ylamino)benzyl]amino}-2-oxoethyl)-1-oxo-2,3,4,5-tetrahydro-1H-2-benzazepin-5-yl]-acetate (I)

0.52 g (5.2 mmol) of N-methylmorpholine was added dropwise at 0° C. to 0.87 g (2.6 mmol) of compound 3 and 0.73 g (2.6 mmol) of N-[4-aminomethyl)phenyl]-1H-benzimidazol-2-amine hydrochloride 4 in 12 ml of DMF, then 0.85 g (2.6 mmol) of TOTU was introduced in portions in the course of 20 min and the mixture was stirred at 0° C. for 1 h. The brown reaction solution was poured into ice water, the brownish amorphous precipitate was filtered off with suction, washed with water and dissolved in 70 ml of ethyl acetate, and the solution was washed 4 times with 5% strength $K_2CO_3$ solution and finally with NaCl solution, dried over $Na_2SO_4$ and concentrated in vacuo to a brown, amorphous residue. After purification by column chromatography (eluent: $CH_2Cl_2$/MeOH, 9/1), 0.54 g (38%) of amorphous powder remained; FAB-MS [M−H+]: 554.

Example II

[2-(2-{[4-(1H-Benzimidazol-2-ylamino)benzyl]amino}-2-oxoethyl)-1-oxo-2,3,4,5-tetrahydro-1H-2-benzazepin-5-yl]acetic acid (II)

0.53 g (10 mmol) of the t-butyl ester from Example I was dissolved in a mixture of 10 ml of $CH_2Cl_2$, 5 ml of glacial acetic acid and 0.25 ml of water, and the solution was treated with 7 ml of 4 N HCl in dioxane and stirred at room temperature overnight. Toward the end, the solvent was distilled off in vacuo with addition of toluene and the residue was purified by column chromatography (eluent: $CH_2Cl_2$/MeOH/50% strength acetic acid, 45/5/1). After stripping off the solvent and digesting with ether, 0.42 g (84%) of amorphous powder remained; FAB-MS [M−$^{H+}$]: 498.

Example III tert-Butyl (2-{2-[(4-{[(benzylamino)carbonyl]amino}benzyl)-amino]-2-oxoethyl}-1-oxo-2,3,4,5-tetrahydro-1H-2-benzazepin-5-yl)acetate (III)

130 mg (0.39 mmol) of the acid 3 are dissolved in 30 ml of $CH_2Cl_2$ and 0.07 ml of HUnig base and 77 mg of EDC (0.4 mmol) are added at 0° C. After 1 h, 100 mg of amine 5 dissolved in 10 ml of DMF are added dropwise and the mixture is stirred for a further 1 h. It is stirred at room temp. for 16 h, the solution is then concentrated, the residue is taken up in $CH_2Cl_2$/water and the mixture is washed with 1% citric acid, 5% $NaHCO_3$ solution and water. The organic phase is dried and concentrated (92 mg).
ESI-MS [M+H$^+$]=571.

Example IV (2-{2-[(4-{[(Benzylamino)carbonyl]amino}benzyl)amino]-2-oxoethyl}-1-oxo-2,3,4,5-tetrahydro-1H-2-benzazepin-5-yl)acetic Acid 40 mg (0.07 mmol) of Example III are dissolved in 3 ml of trifluoroacetic acid and the mixture is stirred at 0° C. for 2 h and at room temp. for 16 h. It is concentrated, and the residue is codistilled repeatedly with $CH_2Cl_2$ and dried (31.8 mg). ESI-MS [M+H$^+$]=515.

Example V tert-Butyl {2-[2-({4-[(1H-benzimidazol-2-ylamino)methyl]-cyclohexyl}amino)-2-oxoethyl]-1-oxo-2,3,4,5-tetrahydro-1H-2-benzazepin-5-yl}acetate (V)

0.6 g (1.8 mmol) of compound 3 and 0.57 g (1.8 mmol) of compound 6 were reacted analogously to Example I and the reaction product was purified by means of preparative thick-layer chromatography (eluent: $CH_2Cl_2$/MeOH/ammonia, 45/5/0.2); 0.45 g of white amorphous powder; ESI-MS [M+H$^+$]: 560.

Example VI 2-({[4-({[5-(Carboxymethyl)-1-oxo-1,3,4,5-tetrahydro-2H-2-benzazepin-2-yl]acetyl}amino)cyclohexyl]methyl}amino)-1H-benzimidazole hydrochloride (VI)

Analogously to Example II, the t-butyl ester (Example V) in glacial acetic acid was cleaved using 4N HCl in dioxane. After freeze-drying, 0.45 g of white amorphous hydrochloride remained; ESI-MS [M+H$^+$]: 504.

Example VII tert-Butyl {2-[2-({[4-(1H-benzimidazol-2-ylamino)cyclohexyl]methyl}amino)-2-oxoethyl]-1-oxo-2,3,4,5-tetrahydro-1H-2-benzazepin-5-yl}acetate (VII)

Analogously to Example V, compound 3 was reacted with 0.57 g (1.8 mmol) of compound 7 and the mixture was purified; 0.5 g of white amorphous powder; ESI-MS [M+H$^+$]: 560.

Example VIII 2-({[4-({[5-(Carboxymethyl)-1-oxo-1,3,4,5-tetrahydro-2H-2-benzazepin-2-yl]acetyl}amino)methyl]cyclohexyl}amino)-1H-benzimidazole hydrochloride (VIII)

Analogously to Example VI, the t-butyl ester (Example VII) was cleaved and lyophilized; 0.35 g of white amorphous residue; ESI-MS [M+H$^+$]: 504.

Example IX tert-Butyl [2-(2-{[3-(1H-benzimidazol-2-ylamino)propyl]amino}-2-oxoethyl)-1-oxo-2,3,4,5-tetrahydro-1H-2-benzazepin-5-yl]acetate (IX)

0.87 g (2.6 mmol) of compound 3 and 0.95 g (3.1 mmol) of compound 4510 were reacted analogously to Example I and the reaction product was purified by column chromatography (eluent: diethyl ether/MeOH/ammonia, 40/10/2.5); 0.8 g of white amorphous powder; ESI-MS [M+H$^+$]: 506.

Example X

2-{[3-({[5-(Carboxymethyl)-1-oxo-1,3,4,5-tetrahydro-2H-2-benzazepin-2-yl]acetyl}amino)propyl]amino)-1H-benzimidazole hydrochloride (X)

Analogously to Example II, the tert-butyl ester (Example IX) in glacial acetic acid was cleaved using 4N HCl in dioxane. After stripping off the solvent, the residue was dissolved in water, clarified with active carbon and then lyophilized; 0.72 g of white amorphous residue; ESI-MS [M+H$^+$]: 450.

Example XI tert-Butyl [2-(2-{[4-(1H-benzimidazol-2-ylamino)butyl]amino}-2-oxoethyl)-1-oxo-2,3,4,5-tetrahydro-1H-2-benzazepin-5-yl]acetate (XI)

Analogously to Example IX, compound 3 was reacted with 1.0 g (3.1 mmol) of compound 9 and the reaction product was purified by column chromatography (eluent: diethyl ether/MeOH/ammonia, 40/10/2.5), 0.78 g of white amorphous powder; ESI-MS [M+H$^+$]: 520.

Example XII

2-{[4-({[5-(Carboxymethyl)-1-oxo-1,3,4,5-tetrahydro-2H-2-benzazepin-2-yl]acetyl}amino)butyl]amino)-1H-benzimidazole hydrochloride (XII)

Analogously to Example X, the tert-butyl ester (Example XI) was cleaved and lyophilized. 0.65 g of white amorphous residue; ESI-MS [M+H$^+$]: 464.

Example XIII tert-Butyl [2-(2-{[5-(1H-benzimidazol-2-ylamino)pentyl]amino}-2-oxoethyl)-1-oxo-2,3,4,5-tetrahydro-1H-2-benzazepin-5-yl]acetate (XIII)

0.87 g (2.6 mmol) of compound 3 and 0.79 g (3.1 mmol) of compound 8 were reacted analogously to Example I and the reaction product was purified by column chromatography (eluent: $CH_2Cl_2$/MeOH/ammonia, 43/7/0.1); 0.74 g of white amorphous powder; ESI-MS [M+H$^+$]: 534.

Example XIV

2-{[5-({(5-(Carboxymethyl)-1-oxo-1,3,4,5-tetrahydro-2H-2-benzazepin-2-yl]acetyl}amino)pentyl]amino)-1H-benzimidazol-1-ium chloride (XIV)

Analagously to Example II, the tert-butyl ester (Example XIII) in glacial acetic acid was cleaved using 4N HCl in dioxane. After stripping off the solvent, the residue was dissolved in water, clarified using active carbon and then lyophilized; 0.67 g of white amorphous residue; ESI-MS [M+H$^+$]: 478.

II. Biological Examples

Example 1

Integrin $\alpha_v\beta_3$ Assay

For the identification and assessment of integrin $\alpha_v\beta_3$ ligands, a test system was used which was based on competition between the natural integrin $\alpha_v\beta_3$ ligand vitronectin and the test substance for binding to solid phase-bound integrin $\alpha_v\beta_3$.

Procedure

Microtiter plates coated with 250 ng/ml of integrin $\alpha_v\beta_3$ in 0.05 M $NaHCO_3$ pH 9.2; 0.1 ml/well;

saturation with 1% powdered milk/assay buffer; 0.3 ml/well; 0.5 h/RT

3× washing with 0.05% Tween 20/assay buffer test substance in 0.1% powdered milk/assay buffer, 50 μl/well 0 μg/ml or 2 μl/ml of human vitronectin (Boehringer Ingelheim T007) in 0.1% powdered milk/assay buffer, 50 μl/well; 1 h/RT 3× washing with 0.05% Tween 20/assay buffer 1 μg/ml of anti human vitronectin antibody coupled to peroxidase (Kordia SAVN-APHRP) in 0.1% powdered milk/assay buffer; 0.1 ml/well; 1 h/RT 3× washing with 0.05% Tween 20/assay buffer 0.1 ml/well of peroxidase substrate stop reaction with 0.1 ml/well of 2 M $H_2SO_4$ measurement of the absorption at 450 nm Integrin $\alpha_v\beta_3$: Human placenta is solubilized with Nonidet and integrin $\alpha_v\beta_3$ affinity-purified on a GRGDSPK matrix (elution with EDTA). Impurities due to integrin $\alpha_{IIb}\beta_3$ and human serum albumin, and the detergent and EDTA are removed by anion-exchange chromatography.

Assay buffer: 50 mM tris pH 7.5; 100 mM NaCl; 1 mM $CaCl_2$; 1 mM $MgCl_2$; 10 μM $MnCl_2$ Peroxidase substrate: mix 0.1 ml of TMB solution (42 mM TMB in DMSO) and 10 ml of substrate buffer (0.1 M sodium acetate pH 4.9), then add 14.7 μl of 3% $H_2O_2$.

Various dilutions of the test substances are employed in the assay and the $IC_{50}$ values are determined (concentration of the ligand at which 50% of the ligand is displaced). The compound from Example II showed the best result here.

Example 2

Integrin $\alpha_{IIb}\beta_3$ assay

The assay is based on competition between the natural integrin $\alpha_{IIb}\beta_3$ ligand fibrinogen and the test substance for binding to integrin $\alpha_{IIb}\beta_3$.

Procedure

Coat microtiter plates with 10 μg/ml of fibrinogen (Calbiochem 341578) in 0.05 M $NaHCO_3$ pH 9.2; 0.1 ml/well;

saturate with 1% BSA/PBS; 0.3 ml/well; 30 min/RT b 3× washing with 0.05% Tween 20/PBS test substance in 0.1% BSA/PBS; 50 μl/well+200 μg/ml of integrin $\alpha_{IIb}\beta_3$ (Kordia) in 0.1% BSA/PBS; 50 μl/well; 2 to 4 h/RT 3× washing as above biotinylated anti integrin $\alpha_{IIb}\beta_3$ antibody (Dianova CBL 130 B); 1:1000 in 0.1% BSA/PBS; 0.1 ml/well; 2 to 4 h/RT 3× washing as above streptavidin-peroxidase complex (B.M. 1089153) 1:10000 in 0.1% BSA/PBS; 0.1 ml/well; 30 min/RT 3× washing as above 0.1 ml/well of peroxidase substrate stop reaction using 0.1 ml/well of 2 M $H_2SO_4$ measurement of the absorption at 450 nm Peroxidase substrate: mix 0.1 ml of TMB solution (42 mM TMB in DMSO) and 10 ml of substrate buffer (0.1 M Na acetate pH 4.9), then add 14.7 μl of 3% $H_2O_2$ Various dilutions of the test substances are employed in the assay and the $IC_{50}$ values are determined (concentration of the antagonists at which 50% of the ligand is displaced). By comparison of the $IC_{50}$ values in the integrin $\alpha_{IIb}\beta_3$ and integrin $\alpha_v\beta_3$ assay, the selectivity of the substances can be determined.

Example 3

CAM Assay

The CAM (chorioallantoic membrane) assay serves as a generally recognized model for the assessment of the in vivo activity of integrin $\alpha_v\beta_3$ antagonists. It is based on the inhibition of angiogenesis and neovascularization of tumor tissue (Am. J. Pathol. 1975, 79, 597-618; Cancer Res. 1980, 40, 2300-2309; Nature 1987, 329, 630). The procedure is carried out analogously to the prior art. The growth of the chicken embryo blood vessels and of the transplanted tumor tissue can be readily monitored and assessed.

Example 4

Rabbit Eye Assay

In this in vivo model, the inhibition of angiogenesis and neovascularization in the presence of integrin $\alpha_v\beta_3$ antagonists can be monitored and assessed analogously to Example 3. The model is generally recognized and is based on the growth of rabbit blood vessels starting from the edge in the cornea of the eye (Proc. Natl. Acad. Sci. USA. 1994, 91, 4082-4085; Science 1976, 193, 70-72). The procedure is carried out analogously to the prior art.

We claim:
1. A compound of the formula I

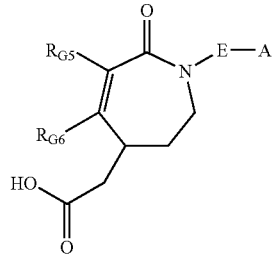

(I)

and the physiologically tolerable salts, and the enantiomerically pure or diastereomerically pure and tautomeric forms thereof, where $R_{G5}$ and $R_{G6}$ independently of one another are hydrogen, a branched or unbranched, optionally substituted $C_1$-$C_6$-alkyl or $C_1$-$C_4$-alkoxy radical, an optionally substituted aryl or arylalkyl radical or both radicals $R_{G5}$ and $R_{G6}$ together are an optionally substituted, fused, unsaturated or aromatic 3- to 10-membered carbocycle or heterocycle, which can contain up to three different or identical heteroatoms O, N, S, where said fused, unsaturated or aromatic 3- to 10-membered carbocycle or heterocycle is optionally substituted by, independently of one another up to four substituents from the group consisting of hydroxyl, halogen or a branched or unbranched, optionally halogen-substituted $C_1$-$C_4$-alkoxy, $C_1$-$C_4$-thioalkyl or $C_1$-$C_4$-alkyl radical or an optionally halogen-substituted aryl, hetaryl or $C_3$-$C_7$-cycloalkyl radical or an optionally halogen-substituted —$SO_2$-$C_1$-$C_4$-alkyl, —SO—$C_1$-$C_4$-alkyl, —$SO_2$-$C_1$-$C_4$-alkylenearyl, —SO—$C_1$-$C_4$-alkylenearyl, —$SO_2$-aryl and —SO-aryl;

A is a structural element selected from the group of structural elements of the formulae $I_A^1$ to $I_A^{18}$,

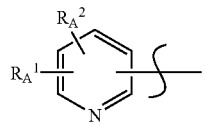

$I_A^1$

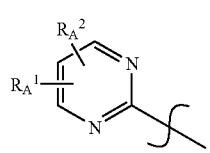

$I_A^2$

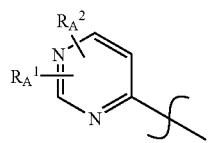

$I_A^3$

-continued

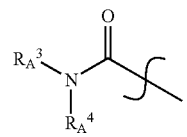

$I_A^4$

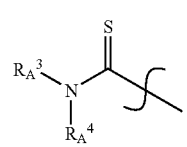

$I_A^5$

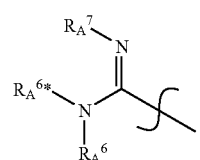

$I_A^6$

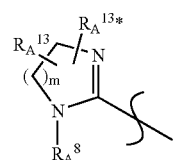

$I_A^7$

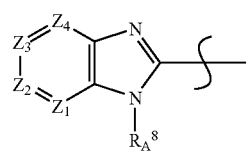

$I_A^8$

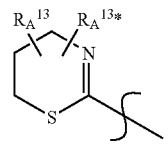

$I_A^9$

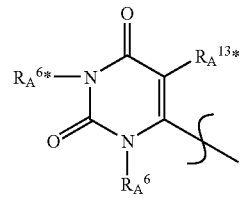

$I_A^{10}$

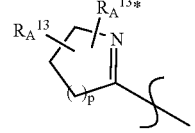

$I_A^{11}$

-continued

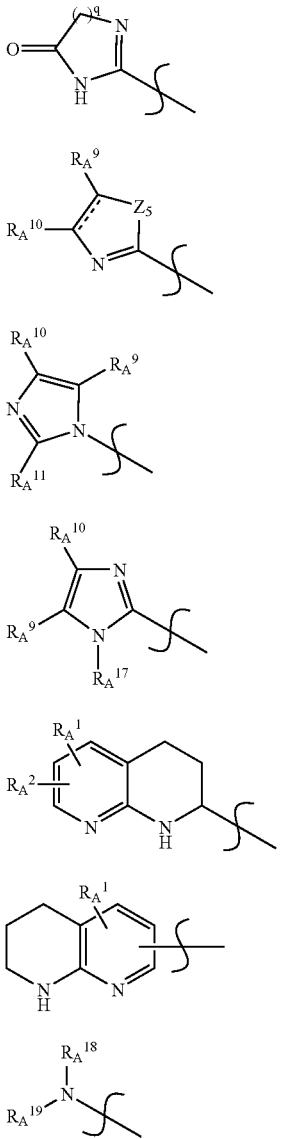

where
m, p and q
independently of one another are 1, 2 or 3,
$R_{A1}$ and $R_{A2}$
independently of one another are hydrogen, CN, halogen, a branched or unbranched, optionally substituted $C_1$-$C_6$-alkyl or CO—$C_1$-$C_6$-alkyl radical or an optionally substituted aryl, arylalkyl, hetaryl, hetarylalkyl or $C_3$-$C_7$-cycloalkyl radical or a radical CO—O—$R_{A14}$, O—$RA_{14}$, S—$R_{A14}$, $NR_{A15}R_{A16}$, CO—$NR_{A15}R_{A16}$ or $SO_2NR_{A15}R_{A16}$ or both radicals $R_{A1}$ and $R_{A2}$ together are a fused, optionally substituted, 5- or 6-membered, unsaturated or aromatic carbocycle or heterocycle which can contain up to three heteroatoms selected from the group O, N, and S,
$R_{A13}$ and $R_{A13*}$
independently of one another are hydrogen, CN, halogen, a branched or unbranched, optionally substituted $C_1$-$C_6$-alkyl or an optionally substituted aryl, arylalkyl, hetaryl, hetarylalkyl or $C_3$-$C_7$-cycloalkyl radical or a radical CO—O—$R_{A14}$, O—$R_{A14}$, S—$R_{A14}$, $NR_{A15}R_{A16}$, $SO_2NR_{A15}R_{A16}$ or CO—$NR_{A15}R_{A16}$
where
$R_{A14}$ is hydrogen, a branched or unbranched, optionally substituted $C_1$-$C_6$-alkyl, alkylene-$C_1$-$C_4$-alkoxy, $C_2$-$C_6$-alkenyl, $C_2$-$C_6$-alkynyl or $C_1$-$C_6$-alkylene-$C_3$-$C_7$-cycloalkyl radical or an optionally substituted $C_3$-$C_7$-cycloalkyl, aryl, arylalkyl, hetaryl or hetarylalkyl radical, $R_{A15}$ and $R_{A16}$,
independently of one another are hydrogen, a branched or unbranched, optionally substituted $C_1$-$C_6$-alkyl, CO—$C_1$-$C_6$-alkyl, $SO_2$—$C_1$-$C_6$-alkyl, COO—$C_1$-$C_6$-alkyl, CO—NH—$C_1$-$C_6$-alkyl, arylalkyl COO-alkylenearyl, $SO_2$-alkylenearyl, CO—NH-alkylenearyl, CO—NH-alkylenehetaryl or hetarylalkyl radical or an optionally substituted $C_3$-$C_7$-cycloalkyl, aryl, CO-aryl, CO—NH-aryl, $SO_2$-aryl, hetaryl, CO—NH-hetaryl or CO-hetaryl radical,
$R_{A3}$ and $R_{A4}$
independently of one another are hydrogen, —(CH$_2$)n—(X$_A$)$_j$—$R_{A12}$, both radicals together are a 3- to 8-membered, saturated, unsaturated or aromatic N-heterocycle which can additionally contain two further, identical or different heteroatoms O, N or 5, where the cycle is optionally substituted or a further, optionally substituted, saturated, unsaturated or aromatic cycle can be fused to this cycle,
where
n is 1,
j is 0 or 1,
$X_A$ is —CO—, —CO—N($R_{x1}$)—, —N($R_{x1}$)—CO—, —N($R_{x1}$)—CO—N($R_{x1*}$)—, —N($R_{x1}$)—CO—O—, —O—, —S—, —SO$_2$—, —SO$_2$—N($R_{x1}$)—, —SO$_2$—O—, —CO—O—, —O—CO—, —O—CO—N($R_{x1}$)—, —N($R_{x1}$)—or —N($R_{x1}$)—SO$_2$,
$R_{A12}$ is hydrogen, a branched or unbranched, optionally substituted $C_1$-$C_6$-alkyl radical, an optionally $C_1$-$C_4$-alkyl- or aryl-substituted $C_2$-$C_6$-alkynyl or $C_2$-$C_6$-alkenyl radical or a 3- to 6-membered, saturated or unsaturated heterocycle, substituted by up to three identical or different radicals, which can contain up to three different or identical heteroatoms O, N, S, a $C_3$-$C_7$-cycloalkyl, aryl or hetaryl radical, where both radicals together can be a fused, saturated, unsaturated or aromatic carbocycle or heterocycle which can contain up to three different or identical heteroatoms O, N, S and the cycle can optionally be substituted or a further, optionally substituted, saturated, unsaturated or aromatic cycle can be fused to this cycle, or the radical $R_{A12}$, together with $R_{x1}$ or $R_{x1*}$ forms a saturated or unsaturated $C_3$-$C_7$-heterocycle which can optionally contain up to two further heteroatoms selected from the group O, S and N,
$R_{x1}$ and $R_{x1*}$
independently of one another are hydrogen, a branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl, CO—$C_1$-$C_6$-alkyl, CO—O—$C_1$-$C_6$-alkyl or $SO_2$—$C_1$-$C_6$-alkyl radical or an optionally substituted $C_3$-$C_7$-cycloalkyl, aryl, arylalkyl, CO—O—alkylenearyl, CO-alkylenearyl, CO-aryl, $SO_2$-aryl, hetaryl, CO-hetaryl or $SO_2$-alkylenearyl radical,
$R_{A6}$ and $R_{A6*}$
are hydrogen, a branched or unbranched, optionally substituted $C_1$-$C_4$-alkyl, —CO—O—$C_1$-$C_4$-alkyl, arylalkyl, —CO—O-alkylenearyl, —CO—O-allyl, —CO—

$C_1$-$C_4$-alkyl, —CO-alkylenearyl, $C_3$-$C_7$-cycloalkyl or —CO-allyl radical or in structural element $I_{47}$ both radicals $R_{46}$ and $R_{46*}$ together are an optionally substituted, saturated, unsaturated or aromatic heterocycle which, in addition to the ring nitrogen, can contain up to two further different or identical heteroatoms O, N, S, $R_{47}$ is hydrogen, —OH, —CN, —CONH$_2$, a branched or unbranched, optionally substituted $C_1$-$C_4$-alkyl, $C_1$-$C_4$-alkoxy, $C_3$-$C_7$-cycloalkyl or —O—CO—$C_1$-$C_4$-alkyl radical, or an optionally substituted arylalkyl, —O-alkylenearyl, —O—CO-aryl, —O—CO-alkylenearyl or —O—CO-allyl radical, or both radicals $R_{46}$ and $R_{47}$ together are an optionally substituted, unsaturated or aromatic heterocycle which, in addition to the ring nitrogen, can contain up to two further different or identical heteroatoms O, N, S, $R_4$ is hydrogen, a branched or unbranched, optionally substituted $C_1$-$C_4$-alkyl, CO—$C_1$-$C_4$-alkyl, SO$_2$-$C_1$-$C_4$-alkyl or CO—O—$C_1$-$C_4$-alkyl radical or an optionally substituted aryl, CO-aryl, SO$_2$-aryl, CO—O-aryl, CO-alkylenearyl, SO$_2$-alkylenearyl, CO—O-alkylenearyl or alkylenearyl radical, $R_{49}$ and $R_{410}$ independently of one another are hydrogen, —CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO—O—$R_{414}$, O—$R_{414}$, S—$R_{414}$, NR$_{415}$R$_{416}$, SO$_2$—NR$_{415}$R$_{416}$ or CO—NR$_{415}$R$_{416}$, or both radicals $R_{49}$ and $R_{410}$ together in structural element $I_{414}$ are a 5- to 7-membered saturated, unsaturated or aromatic carbocycle or heterocycle which can contain up to three different or identical heteroatoms O, N, S and is optionally substituted by up to three identical or different radicals, $R_{411}$ is hydrogen, —CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO—O—$R_{414}$, O—$R_{414}$, S—$R_{414}$, NR$_{415}$R$_{416}$, SO$_2$—NR$_{415}$R$_{416}$ or CO—NR$_{415}$R$_{416}$ $R_{417}$ is hydrogen or, in structural element $I_{416}$, both radicals $R_{49}$ and $R_{417}$ together are a 5- to 7-membered saturated, unsaturated or aromatic heterocycle which, in addition to the ring nitrogen, can contain up to three different or identical heteroatoms O, N, S and is optionally substituted by up to three identical or different radicals, $R_{418}$ and $R_{419}$ independently of one another are hydrogen, a branched or unbranched, optionally substituted $C_1$-$C_6$-alkyl, $C_2$-$C_5$-alkenyl, $C_2$-$C_6$-alkynyl, $C_1$-$C_5$-alkylene-$C_1$-$C_4$-alkoxy, mono- and bisalkylaminoalkylene or acylaminoalkylene radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —SO$_2$—$R_{G4}$, —CO—OR$_{G4}$, —CO—NR$_{G4}$R$_{G4*}$ or —CO—$R_{G4}$ $Z^1$, $Z^2$, $Z^3$ and $Z^4$ independently of one another are nitrogen, C—H, C-halogen or a branched or unbranched, optionally substituted C—$C_1$-$C_4$-alkyl or C—$C_1$-$C_4$-alkoxy radical, $Z^5$ is NR$_{48}$, oxygen or sulfur and wherein for each of the radicals the optional substituents are independently selected from the group consisting of —NO$_2$, —NH$_2$, —OH, —CN, —COOH, —O—CH$_2$—COOH, halogen, a branched or unbranched $C_1$-$C_4$-alkyl radical, CF$_3$, C$_2$F$_5$ or CH$_2$F, —CO—O—$C_1$-$C_4$-alkyl, $C_3$-$C_6$-cycloalkyl, $C_1$-$C_4$-alkoxy, $C_1$-$C_4$-thioalkyl, —NH—CO—O—$C_1$-$C_4$-alkyl, —O—CH$_2$—COO—$C_1$-$C_4$-alkyl, —NH—CO—$C_1$-alkyl, —CO—NH—$C_1$-$C_4$-alkyl, —NH—SO$_2$-$C_1$-$C_4$-alkyl, —SO$_2$—NH—$C_1$-$C_4$-alkyl, —N($C_1$-$C_4$-alkyl)$_2$, —NH—$C_1$-$C_4$-alkyl, or —SO$_2$-$C_1$-$C_4$-alkyl radical, an —NH—CO-aryl, —CO—NH-aryl, —NH—CO—O-aryl, —NH—CO—O-alkylenearyl, —NH—SO$_2$-aryl, —SO$_2$—NH-aryl, —CO—NH-benzyl, —NH—SO$_2$-benzyl, —SO$_2$—NH-benzyl, a radical —SO$_2$—NR$^2$R$^3$ or —CO—NR$^2$R$^3$ where the radicals R$^2$ and R$^3$ independently of one another can have the meaning hydrogen, a branched or unbranched $C_1$-$C_6$-alkyl, $C_3$-$C_7$-cycloalkyl, cycloalkyl, CO—O—$C_1C_e$-alkyl, SO$_2$—$C_1$-$C_6$-alkyl or CO—$C_1$-$C_6$-alkyl radical or a CO—O—alkylenearyl, SO$_2$-aryl, CO-aryl, SO$_2$-alkylenearyl or CO-alkylenearyl radical, or both radicals R$^2$ and R$^3$ together can be a 3- to 6-membered, saturated, unsaturated or aromatic heterocycle which, in addition to the ring nitrogen, can contain up to three further different or. identical heteroatoms O, N, S.

and

E is composed of two to four substructural elements, selected from the group E$^1$ and E$^2$, where the sequence of linkage of the substructural elements is arbitrary and E$^1$ and E$^2$ have the following meanings:

E$^1$ is a substructuralelement of the formula $I_{E1}$ $$—(CR_{E1}R_{E2})_c—(Q_E)_{k2}—(CR_{E3}R_{E4})_d— \qquad I_{E1}$$

and

E$^2$ is a substructural element of the formula $I_{E2}$ $$—(NR_{E11})_{k3}—(CR_{E5}R_{E6})_f—(Z_E)_{k4}—(CR_{E7}R_{E8})_g—(X_E)_{k5}—(CR_{E9}R_{E10})_h—(NR_{E11*})_{k6}— \qquad I_{E2}$$

where c is 1, d, f, g and h independently of one another are 0, 1 or 2, k2, k3, k4, k5 and k6 independently of one another are 0 or 1, $X_E$ and $Q_E$ independently of one another are an optionally substituted 4- to 11-membered mono- or polycyclic, aliphatic or aromatic hydrocarbon which can contain up to 6 double bonds and up to 6 identical or different heteroatoms selected from the group N, O and S, where the ring carbons and/or the ring nitrogens can optionally be substituted, $Z_E$ is CO, CO—NR$_{E12}$, NR$_{E12}$—CO, sulfur, SO, SO$_2$, SO$_2$—N R$_{E12}$, N R$_{E12}$—SO$_2$, CS, CS-NRE$^{12}$, NR$_{E12}$—CS, CS—O, O—CS, CO—O, O—CO, oxygen, ethynylene, C R$_{E13}$—O—CR$_{E14}$, C(=CR$_{E13}$R$_{E14}$), CR$_{E13}$CR$_{E14}$, —CR$_{E13}$(OR$_{E15}$)—CHR$_{E14}$—or —CHR$_{E13}$—CR$_{E14}$(OR$_{E15}$)—, R$_{E1}$, R$_{E2}$, R$_{E3}$, R$_{E4}$, R$_{E5}$, R$_{E6}$, R$_{E7}$, R$_{E8}$, R$_{E9}$ and R$_{E10}$ independently of one another are hydrogen, halogen, a hydroxyl group, a branched or unbranched, optionally substituted $C_1$-$C_6$-alkyl, $C_2$-$C_6$-alkenyl, $C_2$-$C_6$-alkynyl or alkylenecycloalkyl radical, a radical —(CH$_2$)$_x$—(W$_E$)$_z$—R$_{E17}$, an optionally substituted C$_3$-C$_7$-cycloalkyl, aryl, arylalkyl, hetaryl or hetarylalkyl radical or independently of one another in each case two radicals R$_{E1}$ and R$_{E2}$ or R$_{E3}$ and R$_{E4}$ or R$_{E5}$ and R$_{E6}$ or R$_{E7}$ and R$_{E8}$ or R$_{E9}$ and R$_{E10}$ together are a 3- to 7-membered, optionally substituted, saturated or unsaturated carbocycle or heterocycle which can contain up to three heteroatoms selected from the group O, N and S x is 0, 1, 2, 3 or 4, z is 0 or 1, W$_E$ is —CO—, —CO—N(R$_{w2}$)—, —N(R$_{w2}$)—CO—, —N(R$_{w2}$)—CO—N(R$_{w2*}$)—, —N(R$_{w2}$)—CO—O—, —O—, —S—, —SO$_2$—, —SO$_2$—N(R$_{w2}$)—, —SO$_2$—O—, —CO—O—, —O—CO—, —O—CO—N(R$_{w2}$)—, —N(R$_{w2}$)— or —N(R$_{w2}$)—SO$_2$—, R$_{w2}$ and R$_{w2*}$
independently of one another are hydrogen, a branched or unbranched, optionally substituted C$_1$-C$_6$-alkyl, C$_2$-C$_6$-alkenyl, C$_2$-C$_6$-alkynyl, CO—C$_1$-C$_6$-alkyl, CO—O—C$_1$-C$_6$-alkyl or SO$_2$-C$_1$-C$_6$-alkyl radical or an optionally substituted hetaryl, hetarylalkyl, arylalkyl, C$_3$-C$_7$-cycloalkyl, CO—O-alkylenearyl, CO-alkylenearyl, CO-aryl, SO$_2$-aryl, CO-hetaryl or SO$_2$-alkylenearyl radical, R$_{E17}$ is hydrogen, a hydroxyl group, CN, halogen, a branched or unbranched, optionally substituted C$_1$-C$_6$-alkyl radical, an optionally substituted C$_3$-C$_7$-cycloalkyl, aryl, hetaryl or arylalkyl radical, a C$_2$-C$_6$-alkynyl or C$_2$-C$_6$-alkenyl radical optionally substituted by C$_1$-C$_4$-alkyl or aryl, an optionally substituted C$_6$-C$_{12}$-bicycloalkyl, C$_1$-C$_6$-alkylene-C$_6$-C$_{12}$-bicycloalkyl, C$_7$-C$_{20}$-tricycloalkyl or C$_1$-C$_6$-alkylene-C$_7$-C$_{20}$-tricycloalkyl radical, or a 3 to 8-membered, saturated or unsaturated heterocycle substituted by up to three identical or different radicals, which can contain up to three different or identical heteroatoms O, N, S, where two radicals can together be a fused, saturated, unsaturated or aromatic carbocycle or heterocycle which can contain up to three different or identical heteroatom O, N, S and the cycle can optionally be substituted or a further, optionally substituted, saturated, unsaturated or aromatic cycle can be fused to this cycle, or the radical R$_{E17}$ forms, together with R$_{w2}$ or R$_{w2*}$, a saturated or unsaturated C$_3$-C$_7$-heterocycle which can optionally contain up to two further heteroatoms selected from the group O, S and N, R$_{E11}$ and R$_{E11*}$
independently of one another are hydrogen, a branched or unbranched, optionally substituted C$_1$-C$_6$-alkyl, C$_1$-C$_6$-alkoxyalkyl, C$_2$-C$_6$-alkenyl, C$_2$-C$_6$-alkynyl, CO—C$_1$-C$_6$-alkyl, CO—O—C$_1$-C$_6$-alkyl, CO—NH—C$_1$-C$_6$-alkoxyalkyl, CO—NH—C$_1$-C$_e$-alkyl or SO$_2$—C$_1$-C$_6$-alkyl radical or an optionally substituted hetaryl, arylalkyl, C$_3$-C$_7$-cycloalkyl, CO—O-alkylenearyl, CO—NH-alkylenearyl, CO-alkylenearyl, CO-aryl, CO—NH-aryl, SO$_2$-aryl, CO-hetaryl, SO$_2$-alkylenearyl, SO$_2$-hetaryl or SO$_2$-alkylenehetaryl radical, R$_{E12}$ is hydrogen, a branched or unbranched, optionally substituted C$_1$-C$_6$-alkyl, C$_2$-C$_6$-alkenyl, C$_2$-C$_6$-alkynyl radical, an optionally substituted C$_3$-C$_7$-cycloalkyl, hetaryl, arylalkyl or hetarylalkyl radical or a radical CO—R$_{E16}$, COOR$_{E16}$ or SO$_2$-R$_{E16}$, R$_{E13}$ and R$_{E14}$
independently of one another are hydrogen, a hydroxyl group, a branched or unbranched, optionally substituted C$_1$-C$_6$-alkyl, C$_1$-C$_4$-alkoxy, C$_2$-C$_6$-alkenyl, C$_2$-C$_6$-alkynyl or alkylenecycloalkyl radical or an optionally substituted C$_3$-C$_7$-cycloalkyl, aryl, arylalkyl, hetaryl or hetarylalkyl radical, R$_{E15}$ is hydrogen, a branched or unbranched, optionally substituted C$_1$-C$_6$-alkyl, C$_2$-C$_6$-alkenyl, C$_2$-C$_6$-alkynyl or alkylenecycloalkyl radical or an optionally substituted C$_3$-C$_7$-cycloalkyl, aryl, arylalkyl, hetaryl or hetarylalkyl radical, R$_{E16}$ is hydrogen, a hydroxyl group, a branched or unbranched, optionally substituted C$_1$-C$_6$-alkyl, C$_2$-C$_6$-alkenyl, C$_2$-C$_6$-alkynyl or C$_1$-C$_6$-alkylene-C$_1$-C$_4$-alkoxy radical, or an optionally substituted aryl, heterocycloalkyl, heterocycloalkenyl, hetaryl, C$_3$-C$_7$-cycloalkyl, C$_1$-C$_4$-alkylene-C$_3$-C$_7$-cycloalkyl, arylalkyl, C$_1$-C$_4$-alkylene-C$_3$-C$_7$-heterocycloalkyl, C$_1$-C$_4$-alkylene-C$_3$-C$_7$-heterocycloalkenyl or hetarylalkyl radical and wherein for each of the radicals the optional substituents are independently selected from the group consisting of —NO$_2$, —NH$_2$, —OH, —CN, —COOH, —O—CH$_2$—COOH, halogen, a branched or unbranched C$_1$-C$_4$-alkyl radical, CF$_3$, C$_2$F$_5$ or CH$_2$F, —CO—O—C$_1$-C$_4$-alkyl, C$_3$-C$_6$-cycloalkyl, C$_1$-C$_4$-alkoxy, C$_1$-C$_4$-thioalkyl, —NH—CO—O—C$_1$-C$_4$-alkyl, —O—CH$_2$—COO-C$_1$-C$_4$-alkyl, —NH—CO—C$_1$-C$_4$-alkyl, —CO—NH—C$_1$-C$_4$-alkyl, —NH—SO$_2$-C$_1$-C$_4$-alkyl, —SO$_2$—NH—C$_1$-C$_4$-alkyl, —N(C$_1$-C$_4$-alkyl)$_2$, —NH—C$_1$-C$_4$-alkyl, or —SO$_2$-C$_1$-C$_4$-alkyl radical, an —NH—CO-aryl, —CO—NH-aryl, —NH—CO—O-aryl, —NH—CO—O-alkylenearyl, —NH—SO$_2$-aryl, —SO$_2$—NH-aryl, —CO—NH-benzyl, —NH—SO$_2$-benzyl, —SO$_2$—NH-benzyl, a radical —SO$_2$—NR$^2$R$^3$ or —CO—NR$^2$R$^3$ where the radicals R$^2$ and R$^3$ independently of one another can have the meaning hydrogen, a branched or unbranched C$_1$-C$_6$-alkyl, C$_3$-C$_7$-cycloalkyl, CO—O—C$_1$-C$_e$-alkyl, SO$_2$—C$_1$-C$_6$-alkyl or CO—C$_1$-C$_6$-alkyl radical or a CO—O-alkylenearyl, SO$_2$-aryl, CO-aryl, SO$_2$-alkylenearyl or CO-alkylenearyl radical, or both radicals R$^2$ and R$^3$ together can be a 3- to 6-membered, saturated, unsaturated or aromatic heterocycle which, in addition to the ring nitrogen, can contain up to three further different or identical heteroatoms O, N, S.

2. A compound as claimed in claim 1, wherein the spacer structural element E is a structural element of the formula I$_{E1E2}$ $$\text{-E}^1\text{-E}^2\text{-} \qquad\qquad I_{E1E2}$$

where:

E$^1$ is a substructural element of the formula I$_{E1}$ $$-(CR_{E1}R_{E2})\text{-}(Q_E)_{k2}\text{-}(CR_{E3}R_{E4})_d- \qquad I_{E1}$$

and E$_2$ is a substructural element of the formula I$_{E2}$ $$-(NR_{E4})_{k3}-(CR_{E5}R_{E6})_f-(Z_E)_{k4}-(CR_{E7}R_{E8})_g-(X_E)_{k5}-(CR_{E9}R_{E10})_h-(NR_{E11*})_{k6}-$$

where c is 1, d, f, g and h
independently of one another are 0, 1 or 2, k1, k2, k3, k4, k5 and k6
independently of one another are 0 or 1, $X_E$ and $Q_E$
independently of one another are an optionally substituted 4- to 11-membered mono- or polycyclic, aliphatic or aromatic hydrocarbon which can contain up to 6 double bonds and up to 6 identical or different heteroatoms selected from the group N, O, and S, where the ring carbons and/or the ring nitrogens can optionally be substituted, $Z_E$
is CO, CO—$NR_{E12}$, $NR_{E12}$—CO, sulfur, SO, $SO_2$, $SO_2$—$NR_{E12}$, $HR_{E12}$—$SO_2$, CS, CS—$NR_{E12}$, $NR_{E12}$—CS, CS—O, O—CS, CO—O, O—CO, oxygen, ethynylene, $CR_{E11}$—O—$CR_{E14}$, $C(=CR_{E11}R_{E14})$, $CR_{E13}CR_{E14}$, —$CR_{E13}OR_{E14}$—$CHR_{E14}$— or —$CHR_{E13}$—$CR_{E14}COR_{E15}$—, $R_{E1}$, $R_{E2}$, $R_{E3}$, $R_{E4}$, $R_{E5}$, $R_{E6}$, $R_{E7}$, $R_{E8}$, $R_{E9}$ and $RE_{10}$
independently of one another are hydrogen, halogen, a hydroxyl group, a branched or unbranched, optionally substituted $C_1$-$C_6$-alkyl, $C_2$-$C_6$-alkenyl, $C_2$-$C_6$-alkynyl or alkylenecycloalkyl radical, a radical —$(CH_2)x$—$(W_E)_z$—$R_{E17}$, an optionally substituted $C_3$-$C_7$-cycloalkyl, aryl, arylalkyl, hetaryl or hetarylalkyl radical or independently of one another are in each case two radicals $R_{E1}$ and $R_{E2}$ or $R_{E3}$ and $R_{E4}$ or $R_{E5}$ and $R_{E6}$ or $R_{E7}$ and $R_{E8}$ or $R_{E9}$ and $RE_{10}$ together are a 3- to 7-membered, optionally substituted, saturated or unsaturated carbo- or heterocycle, which can contain up to three heteroatoms selected from the group O, N, S, x is 0, 1, 2, 3 or 4, z is 0 or 1, $W_E$ is —CO—, —CO—$N(R_{w2})$—, —$N(R_{w2})$—CO—, —$N(R_{w2})$—CO—$N(R_{w2*})$—, —$N(R_{w2})$—CO—O—, —O—, —S—, —$SO_2$—, —$SO_2$—$N(R_{w2})$—, —$SO_2$—O—, —CO—O—, —O—CO—, —O—CO—$N(R_{w2})$—, —$N(R_{w2})$— or —$N(R_{w2})$—$SO_2$—, $R_{w2}$ and $R_{2w*}$ independently of one another are hydrogen, a branched or unbranched, optionally substituted $C_1$-$C_6$-alkyl, $C_2$-$C_6$-alkenyl, $C_2$-$C_6$-alkynyl, CO—$C_1$-$C_6$-alkyl, CO—O—$C_1$-$C_6$-alkyl or $SO_2$-$C_1$-$C_6$-alkyl radical or an optionally substituted hetaryl, hetarylalkyl, arylalkyl, $C_3$-$C_7$-cycloalkyl, CO-O-alkylenearyl, CO-alkylenearyl, CO-aryl, $SO_2$-aryl, CO-hetaryl or $SO_2$-alkylenearyl radical, $R_{E17}$ is hydrogen, a hydroxyl group, CN, halogen, a branched or unbranched, optionally substituted $C_1$-$C_6$-alkyl radical, an optionally substituted $C_3$-$C_7$-cycloalkyl, aryl, hetaryl or arylalkyl radical, a $C_2$-$C_6$-alkynyl or $C_2$-$C_6$-alkenyl radical optionally substituted by $C_1$-$C_4$-alkyl or aryl, an optionally substituted $C_6$-$C_{12}$-bicycloalkyl, $C_1$-$C_6$-alkylene-$C_6$-$C_{12}$-bicycloalkyl, $C_7$-$C_{20}$-tricycloalkyl or $C_1$-$C_6$-alkylene-$C_7$-$C_{20}$-tricycloalkyl radical, or a 3- to 8-membered, saturated or unsaturated heterocycle, which is substituted by up to three identical or different radicals, which can contain up to three different or identical heteroatoms O, N, S, where two radicals together can be a fused, saturated, unsaturated or aromatic carbocycle or heterocycle which can contain up to three different or identical heteroatoms O, N, S and the cycle can optionally be substituted or a further, optionally substituted, saturated, unsaturated or aromatic cycle can be fused to this cycle, or the radical $R_{E17}$ forms together with $R_{w2}$ or $R_{w2*}$ a saturated or unsaturated $C_3$-$C_7$-heterocycle which can optionally contain up to two further heteroatoms selected from the group O, S and N, $R_{E11}$ and $R_{E11*}$
independently of one another are hydrogen, a branched or unbranched, optionally substituted $C_1$-$C_6$-alkyl, C1-$C_6$-alkoxyalkyl, $C_2$-$C_6$-alkenyl, $C_2$-$C_{12}$-alkynyl, CO—$C_1$-$C_6$-alkyl, CO—O—$C_1$-$C_6$-alkyl, CO—NH—$C_1$-$C_6$-alkoxyalkyl, CO—NH—$C_1$-$C_6$-alkyl or $SO_2$—$C_1$-$C_6$-alkyl radical or an optionally substituted hetaryl, arylalkyl, $C_3$-$C_7$-cycloalkyl, CO—O-alkylenearyl, CO—NH-alkylenearyl, CO-alkylenearyl, CO-aryl, CO—NH-aryl, $SO_2$-aryl, CO-hetaryl, $SO_2$-alkylenearyl, $SO_2$-hetaryl or $SO_2$-alkylenehetaryl radical, $R_{E12}$ is hydrogen, a branched or unbranched, optionally substituted $C_1$-$C_6$-alkyl, $C_2$-$C_6$-alkenyl, $C_2$-$C_6$-alkynyl, an optionally substituted $C_3$-$C_7$-cycloalkyl, hetaryl, arylalkyl or hetarylalkyl radical or a radical CO—$R_{E16}$, COOR$_{E16}$ or $SO_2$—$R_{E16}$, $R_{E13}$ and $R_{E14}$
independently of one another are hydrogen, a hydroxyl group, a branched or unbranched, optionally substituted $C_1$-$C_6$-alkyl, $C_1$-$C_4$-alkoxy, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, $R_{E15}$ is hydrogen, a branched or unbranched, optionally substituted $C_1$-$C_6$-alkyl, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, $R_{E16}$ is hydrogen, a hydroxyl group, a branched or unbranched optionally substituted $C_1$-$C_6$-alkyl, $C_2$-$C_6$-alkenyl, $C_2$-$C_6$-alkynyl or $C_1$-$C_5$-alkylene-$C_1$-$C_4$-alkoxy radical, or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkylene-$C_3$-$C_7$-heterocycloalkyl, $C_1$-$C_4$-alkylene-$C_3$-$C_7$ heterocycloalkenyl or hetarylalkyl radical and wherein for each of the radicals the optional substituents are independently selected from the group consisting of —$NO_2$, —$NH_2$, —OH, —CN, —COOH, —O—$CH_2$—COOH, halogen, a branched or unbranched $C_1$-$C_4$-alkyl radical, $CF_3$, $C_2F_5$ or $CH_2F$, —CO—O—$C_1$-$C_4$-alkyl, $C_3$-$C_6$-cycloalkyl, $C_1$-$C_4$-alkoxy, $C_1$-$C_4$-thioalkyl, —NH—CO—O—$C_1$-$C_4$-alkyl, —O—$CH_2$—COO—$C_1$-$C_4$-alkyl, —NH—CO—$C_1$-$C_4$-alkyl, —CO—NH—$C_1$-$C_4$-alkyl, —NH—$SO_2$—$C_1$-$C_4$-alkyl, —$SO_2$—NH—$C_1$-$C_4$-alkyl, —N($C_1$-$C_4$-alkyl)$_2$, —NH—$C_1$-$C_4$-alkyl, or —$SO_2$—$C_1$-$C_4$-alkyl radical, an —NH—CO-aryl, —CO—NH-aryl, —NH—CO—O-aryl, —NH—CO—O-alkylenearyl, —NH—$SO_2$-aryl, —$SO_2$—NH-aryl, —CO—NH-benzyl, —NH—$SO_2$-benzyl, —$SO_2$—NH-benzyl, a radical —$SO_2$—$NR^2R^3$ or —CO—$NR^2R^3$ where the radicals $R^2$ and $R^3$ independently of one another can have the meaning hydrogen, a branched or unbranched $C_1$-$C_6$-alkyl, $C_3$-$C_7$-cycloalkyl, CO—O—$C_1$-$C_e$-alkyl, $SO_2$—$C_1$-$C_6$-alkyl or CO—$C_1$-$C_6$-alkyl radical or a CO—O-alkylenearyl, $SO_2$-aryl, CO-aryl, $SO_2$-alkylenearyl or CO-alkylenearyl radical, or both radicals $R^2$ and $R^3$ together can be a 3- to 6-membered, saturated, unsaturated or aromatic heterocycle which, in addition to the ring nitrogen, can contain up to three further different or identical heteroatoms O, N and S.

3. A pharmaceutical preparation comprising at least one compound as claimed in claim 1, if appropriate pharmaceutical excipients and at least one further compound selected from the group of collagenase, PDGF antagonists and MMPS.

4. A pharmaceutical preparation comprising at least one compound as claimed in claim 1, if appropriate pharmaceutical excipients and at least one further compound selected from the group of TNF antagonists, antagonists of VLA-$_4$ or VCAM-$_1$, antagonists of LFA-$_1$, Mac-$_1$ or ICAMs, immunosuppressants, interleukin-$_1$, -$_5$ or -$_8$ antagonists and dihydrofolate reductase inhibitors.

5. A method for treating rheumatoid arthritis comprising administering an effective amount of the pharmaceutical preparation of claim 4 to a patient in need of such treatment.

6. A pharmaceutical preparation comprising at least one compound as claimed in claim 1, if appropriate pharmaceutical excipients and at least one further compound selected from the group of compounds for antiresorptive therapy, recombinant human growth hormone, bisphosphonates, compounds for calcitonin therapy, calcitonin stimulants, calcium channel antagonists, bone formation stimulants, interleukin-$_6$ antagonists and Src tyrosine kinase inhibitors.

7. A method for treating osteoporosis comprising administering an effective amount of the pharmaceutical preparation of claim 6 to a patient in need of such treatment.

8. A pharmaceutical preparation comprising at least one compound as claimed in claim 1, if appropriate pharmaceutical excipients and at least one further compound selected from the group of cytostatic or antineoplastic compounds, and heparin or low-molecular weight heparins.

9. A pharmaceutical preparation comprising at least one compound as claimed in claim 1, if appropriate pharmaceutical excipients and at least one further compound selected from the group of lipid-lowering compounds, selectin antagonists, antagonists of ICAM-$_1$ or VCAM-$_1$ heparin or low-molecular weight heparins, inhibitors of MMPs, endothelin antagonists, apolipoprotein A$_1$ antagonists, cholesterol antagonists, HMG CoA reductase inhibitors, ACAT inhibitors, ACE inhibitors, angiotensin receptor antagonists, tyrosine kinase inhibitors, protein kinase C inhibitors, calcium channel antagonists, LDL receptor function stimulants, antioxidants LCAT mimetics and free radical scavengers.

10. A pharmaceutical preparation comprising at least one compound as claimed in claim 1, if appropriate pharmaceutical excipients and at least one further compound selected from the group of antagonists of the cell response mediated by EGF, PDGF, VEGF or bFGF, heparin or low-molecular weight heparins, inhibitors of MMPs, selectin antagonists, endothelin antagonists, ACE inhibitors, angiotensin receptor antagonists, glycosylation inhibitors and AGE formation inhibitors or AGE breakers and antagonists of their receptors.

11. A pharmaceutical preparation comprising at least one compound as claimed in claim 1, if appropriate pharmaceutical excipients and at least one further compound selected from the group of thrombin inhibitors, inhibitors of factor Xa, inhibitors of blood platelet adhesion, activation or aggregation, endothelin receptor antagonists, nitrogen oxide synthase inhibitors, CD$_{44}$ antagonists, selectin antagonists, MCP-$_1$ antagonists, inhibitors of signal transduction in proliferating cells, antagonists of the cell response mediated by EGF, PDGF, VEGF or bFGF and antioxidants.

12. A pharmaceutical preparation comprising at least one compound as claimed in claim 1, if appropriate pharmaceutical excipients and at least one further compound selected from the group of endothelin antagonists, ACE inhibitors, angiotensin receptor antagonists, endopeptidase inhibitors, beta-blockers, calcium channel antagonists, phosphodiesterase inhibitors and caspase inhibitors.

13. A pharmaceutical preparation, comprising at least one compound as claimed in claim 1, if appropriate pharmaceutical excipients and at least one further compound selected from the group of inhibitors of blood platelet activation or aggregation, serine protease inhibitors, fibrinogen-lowering compounds, selectin antagonists, antagonists of ICAM-$_1$ or VCAM-$_1$ inhibitors of leukocyte adhesion inhibitors of vascular wall transmigration, fibrinolysis-modulating compounds, inhibitors of complement factors, endothelin receptor antagonists, tyrosine kinase inhibitors, antioxidants and interleukin 8 antagonists.

14. A pharmaceutical preparation, comprising at least one compound as claimed in claim 1, if appropriate pharmaceutical excipients and at least one further compound selected from the group of inhibitors of blood platelet adhesion, activation or aggregation, antagonists of blood platelet-activating compounds and selectin antagonists.

15. A method for the treatment of rheumatoid arthritis, osteoporosis, hyperparathyroidism, Paget's disease, malignant hypercalcemia or metastatic osteolytic lesions comprising administering an effective amount of a compound of claim 1 to a patient in need of such treatment.

16. A pharmaceutical preparation, comprising at lease one compound as claimed in claim 1 in addition to the customary pharmaceutical excipients.

* * * * *